(12) United States Patent
Herold et al.

(10) Patent No.: US 7,868,036 B2
(45) Date of Patent: Jan. 11, 2011

(54) ORGANIC COMPOUNDS

(75) Inventors: Peter Herold, Basel (CH); Stefan Stutz, Basel (CH); Robert Mah, Muttenz (CH); Vincenzo Tschinke, Binningen (CH); Aleksandar Stojanovic, Basel (CH); Nathalie Jotterand, Basel (CH); Michael Quirmbach, Basel (CH); Dirk Behnke, Grenzach-Wyhlen (DE); Christiane Marti, Baden (CH)

(73) Assignee: Novartis AG, Basel (CH)

( * ) Notice: Subject to any disclaimer, the term of this patent is extended or adjusted under 35 U.S.C. 154(b) by 250 days.

(21) Appl. No.: 10/593,461

(22) PCT Filed: Mar. 17, 2005

(86) PCT No.: PCT/EP2005/051241

§ 371 (c)(1), (2), (4) Date: Sep. 19, 2006

(87) PCT Pub. No.: WO2005/090304

PCT Pub. Date: Sep. 29, 2005

(65) Prior Publication Data

US 2008/0058320 A1 Mar. 6, 2008

(30) Foreign Application Priority Data

Mar. 19, 2004 (CH) ..................... 0479/04

(51) Int. Cl.
*A61K 31/405* (2006.01)
*C07D 209/04* (2006.01)

(52) U.S. Cl. ...................... 514/415; 548/509

(58) Field of Classification Search ............. 548/509; 514/415

See application file for complete search history.

(56) References Cited

U.S. PATENT DOCUMENTS

| 5,559,111 A | 9/1996 | Göschke et al. |
|---|---|---|
| 5,606,078 A | 2/1997 | Göschke et al. |
| 5,627,182 A | 5/1997 | Göschke et al. |
| 5,646,143 A | 7/1997 | Göschke et al. |
| 5,654,445 A | 8/1997 | Göschke et al. |
| 5,659,065 A | 8/1997 | Göschke |
| 5,705,658 A | 1/1998 | Göschke et al. |
| 7,312,360 B2 * | 12/2007 | TenBrink et al. ............ 564/185 |
| 2004/0044072 A1 | 3/2004 | TenBrink et al. |

FOREIGN PATENT DOCUMENTS

| EP | 0 678 503 | 10/1995 |
|---|---|---|
| WO | 02/40007 | 5/2002 |
| WO | 03/050073 | * 6/2003 |

OTHER PUBLICATIONS

Oxford et al., 1998, CAS: 108:204491.*
Jeanette M. Wood et al., "Structure-based design of aliskiren, a novel orally effective renin inhibitor", Biochemical and Biophysical Research Communications, Academic Press, Inc., vol. 308, No. 4, pp. 698-705, XP004447169, ISSN: 0006-291X, Sep. 5, 2003.

* cited by examiner

*Primary Examiner*—Rei-tsang Shiao
(74) *Attorney, Agent, or Firm*—Wenderoth, Lind & Ponack, L.L.P.

(57) ABSTRACT

The invention relates to novel amino alcohols of the general formula (I) where X, $R^1$, $R^2$, $R^3$, $R^4$, $R^5$ and $R^6$ are each as defined in detail in the description, to a process for their preparation and to the use of these compounds as medicines, in particular as renin inhibitors.

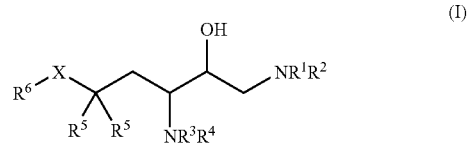

(I)

10 Claims, No Drawings

ORGANIC COMPOUNDS

The invention relates to novel amino alcohols, to processes for preparing the inventive compounds, to pharmaceutical preparations comprising them and to their use as medicament active ingredients, especially renin inhibitors.

Amino-compounds showing renin-inhibiting properties are known, for example from EP519433

The present invention firstly provides compounds of the general formula

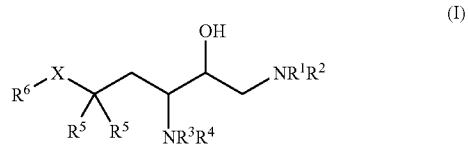

(I)

where

X is methylene or hydroxymethylene;

$R^1$ a) is hydrogen; or b) is $C_1$-$C_8$-alkyl, $C_3$-$C_8$-cycloalkyl, $C_1$-$C_8$-alkanoyl, $C_1$-$C_8$-alkoxycarbonyl, aryl-$C_0$-$C_4$-alkyl or heterocyclyl-$C_0$-$C_4$-alkyl, which radicals may be substituted by 1-4 $C_1$-$C_8$-alkyl, halogen, cyano, oxide, oxo, trifluoromethyl, $C_1$-$C_8$-alkoxy, $C_1$-$C_8$-alkoxycarbonyl, aryl or heterocyclyl;

$R^2$ a) is $C_1$-$C_8$-alkyl, $C_3$-$C_8$-cycloalkyl, $C_1$-$C_8$-alkylsulphonyl, $C_3$-$C_8$-cycloalkylsulphonyl, aryl-$C_0$-$C_8$-alkylsulphonyl, heterocyclylsulphonyl, $C_3$-$C_{12}$-cycloalkyl-$C_1$-$C_8$-alkanoyl, $C_3$-$C_{12}$-cycloalkyl-$C_3$-$C_8$-cycloalkanoyl, aryl-$C_1$-$C_8$-alkanoyl, heterocyclyl-$C_1$-$C_8$-alkanoyl, aryl-$C_3$-$C_8$-cycloalkanoyl, $C_1$-$C_8$-alkanoyl, $C_1$-$C_8$-alkoxycarbonyl, optionally N-mono or N,N-di-$C_1$-$C_8$-alkylated Carbamoyl-$C_0$-$C_8$-alkyl, aryl-$C_0$-$C_4$-alkyl or heterocyclyl-$C_0$-$C_4$-alkyl, which radicals may be substituted by 1-4 $C_1$-$C_8$-alkyl, $C_3$-$C_8$-cycloalkyl, $C_3$-$C_8$-cycloalkoxy, amino, $C_{1-6}$-alkylamino, di-$C_{1-6}$-alkylamino, $C_0$-$C_6$-alkylcarbonylamino, halogen, cyano, hydroxyl, oxide, oxo, trifluoromethyl, $C_1$-$C_8$-alkoxy, optionally N-mono or N,N-di-$C_1$-$C_8$-alkylated carbamoyl, $C_1$-$C_8$-alkoxycarbonyl, $C_{1-6}$-alkylenedioxy, aryl or heterocyclyl; or b) together with $R_1$ and the nitrogen atom to which they are bonded, is a saturated or partly unsaturated 4-8-membered heterocyclic ring which may contain an additional nitrogen, oxygen or sulphur atom or an —SO- or —SO2-group, and the additional nitrogen atom may optionally be substituted by $C_1$-$C_8$-alkyl, $C_1$-$C_8$-alkanoyl, $C_1$-$C_8$-alkoxycarbonyl, aryl or heterocyclyl radicals, in which case this heterocyclic ring may be part of a bicyclic or tricyclic ring system having a total of up to 16 members and the second ring may also contain a nitrogen, oxygen or sulphur atom or an —SO- or —SO2-group, and the nitrogen atom of the second ring may optionally be substituted by $C_1$-$C_8$-alkyl, $C_1$-$C_8$-alkanoyl, $C_1$-$C_8$-alkoxycarbonyl, aryl or heterocyclyl radicals, and all ring systems mentioned may be substituted by 1-4 $C_1$-$C_8$-alkyl, halogen, hydroxyl, oxide, oxo, trifluoromethyl, $C_1$-$C_8$-alkoxy, $C_1$-$C_8$-alkoxy-$C_1$-$C_8$-alkyl, $C_1$-$C_8$-alkoxy-$C_1$-$C_8$-alkoxy, $C_1$-$C_8$-alkoxycarbonylamino, $C_1$-$C_8$-alkylcarbonylamino, $C_1$-$C_8$-alkylamino, N,N-di-$C_1$-$C_8$-alkylamino, aryl-$C_0$-$C_4$-alkyl, aryloxy-$C_0$-$C_4$-alkyl, aryl-$C_0$-$C_4$-alkyl-$C_1$-$C_8$-alkoxy, aryloxy-$C_0$-$C_4$-alkyl-$C_1$-$C_8$-alkoxy, heterocyclyl-$C_0$-$C_4$-alkyl, heterocyclyloxy-$C_0$-$C_4$-alkyl, heterocyclyl-$C_0$-$C_4$-alkyl-$C_1$-$C_8$-alkoxy or heterocyclyloxy-$C_0$-$C_4$-alkyl-$C_1$-$C_8$-alkoxy;

$R^3$ is hydrogen, $C_1$-$C_4$-alkyl, $C_1$-$C_8$-alkoxycarbonyl or $C_1$-$C_8$-alkanoyl;

$R^4$ is hydrogen, $C_1$-$C_4$-alkyl, $C_1$-$C_8$-alkoxycarbonyl or $C_1$-$C_8$-alkanoyl;

$R^5$ are each independently hydrogen, $C_1$-$C_8$-alkyl or, together with the carbon atom to which they are bonded, are a $C_3$-$C_8$-cycloalkylidene radical;

(A) $R^6$ is a heterocyclyl radical or a polycyclic, unsaturated hydrocarbon radical which is substituted by from one to four radicals selected from $C_1$-$C_6$-alkyl, $C_{3-8}$-cycloalkyl, $C_{3-8}$-cycloalkoxy, $C_{3-8}$-cycloalkoxy-$C_{1-6}$-alkyl, $C_{3-8}$-cycloalkoxy-$C_{1-6}$-alkoxy, $C_1$-$C_6$-alkylamino, di-$C_1$-$C_6$-alkylamino, amino-$C_{1-6}$-alkyl, amino-$C_{2-7}$-alkoxy, polyhalo-$C_{1-6}$-alkyl, polyhalo-$C_{2-7}$-alkoxy, nitro, amino, $C_2$-$C_6$-alkenyl, $C_1$-$C_6$-alkoxy, $C_1$-$C_6$-alkanoyloxy, hydroxyl, halogen, oxide, oxo, cyano, carbamoyl, carboxy, $C_1$-$C_6$-alkylenedioxy, phenyl, phenoxy, phenylthio, phenyl-$C_1$-$C_6$-alkyl or phenyl-$C_1$-$C_6$-alkoxy, each of which are optionally substituted by halogen, $C_1$-$C_6$-alkyl, $C_{1-6}$-alkoxy, hydroxyl, $C_1$-$C_6$-alkylamino, di-$C_1$-$C_6$-alkylamino, $C_{1-6}$-alkoxycarbonyl, hydroxy-$C_{1-6}$-alkyl or trifluoromethyl, pyridylcarbonylamino-$C_{1-6}$-alkyl, $C_{2-7}$-alkenyloxy, $C_{1-6}$-alkoxy-$C_{1-6}$-alkoxy, $C_{1-6}$-alkoxy-$C_{1-6}$-alkoxy-$C_{1-6}$-alkyl, methoxybenzyloxy, hydroxybenzyloxy, methylenedioxybenzyloxy, dioxolanyl-$C_{1-6}$-alkoxy, $C_{3-8}$-cycloalkyl-$C_{1-6}$-alkyl, $C_{3-8}$-cycloalkyl-$C_{1-6}$-alkoxy, hydroxy-$C_{2-7}$-alkoxy, carbamoyloxy-$C_{2-7}$-alkoxy, pyridylcarbamoyloxy-$C_{2-7}$-alkoxy, benzoyloxy-$C_{2-7}$-alkoxy, $C_{1-6}$-alkoxycarbonyl, $C_{1-6}$-alkylcarbonylamino, $C_{1-6}$-alkylcarbonylamino-$C_{1-6}$-alkyl, $C_{1-6}$-alkylcarbonylamino-$C_{2-7}$-alkoxy, (N—$C_{1-6}$-alkyl)-$C_{1-6}$-alkylcarbonylamino-$C_{1-6}$-alkyl, (N—$C_{1-6}$-alkyl)-$C_{1-6}$-alkylcarbonylamino-$C_{2-7}$-alkoxy, $C_{3-8}$-cycloalkylcarbonylamino-$C_{1-6}$-alkyl, $C_{3-8}$-cycloalkylcarbonylamino-$C_{2-7}$-alkoxy, $C_{1-6}$-alkoxy-$C_{1-6}$-alkyl, hydroxy-$C_{1-6}$-alkyl, hydroxy-$C_{2-7}$-alkoxy-$C_{1-6}$-alkyl, hydroxy-$C_{2-7}$-alkoxy-$C_{1-6}$-alkoxy, $C_{1-6}$-alkoxycarbonylamino-$C_{1-6}$-alkyl, $C_{1-6}$-alkoxycarbonylamino-$C_{2-7}$-alkoxy, $C_{1-6}$-alkylaminocarbonylamino-$C_{1-6}$-alkyl, $C_{1-6}$-alkylaminocarbonylamino-$C_{2-7}$-alkoxy, $C_{1-6}$-alkylaminocarbonyl-$C_{1-6}$-alkyl, $C_{1-6}$-alkylaminocarbonyl-$C_{1-6}$-alkoxy, $C_{1-8}$-alkylaminocarbonyl-$C_{1-6}$-alkoxy-$C_{1-6}$-alkyl, di-$C_{1-6}$-alkylaminocarbonyl-$C_{1-6}$-alkyl, di-$C_{1-6}$-alkylaminocarbonyl-$C_{1-6}$-alkoxy, $C_{1-6}$-alkylcarbonyloxy-$C_{1-6}$-alkyl, $C_{1-6}$-alkylcarbonyloxy-$C_{2-6}$-alkoxy, cyano-$C_{1-6}$-alkyl, cyano-$C_{1-6}$-alkoxy, 2-oxooxazolidinyl-$C_{1-6}$-alkyl, 2-oxooxazolidinyl-$C_{1-6}$-alkoxy, $C_{1-6}$-alkoxycarbonyl-$C_{1-6}$-alkyl, $C_{1-6}$-alkoxycarbonyl-$C_{1-6}$-alkoxy, $C_{1-6}$-alkylsulphonylamino-$C_{1-6}$-alkyl, $C_{1-6}$-alkylsulphonylamino-$C_{2-7}$-alkoxy, (N—$C_{1-6}$-alkyl)-$C_{1-6}$-alkylsulphonylamino-$C_{1-6}$-alkyl, (N—$C_{1-6}$-alkyl)-$C_{1-6}$-alkylsulphonylamino-$C_{2-7}$-alkoxy, $C_{1-6}$-alkylamino-$C_{1-6}$-alkyl, $C_{1-6}$-alkylamino-$C_{2-7}$-alkoxy, di-$C_{1-6}$-alkylamino-$C_{1-6}$-alkyl, di-$C_{1-6}$-alkylamino-$C_{2-7}$-alkoxy, $C_{1-6}$-alkylsulphonyl-$C_{1-6}$-alkyl, $C_{1-6}$-alkylsulphonyl-$C_{1-6}$-alkoxy, carboxy-$C_{1-6}$-alkyl, carboxy-$C_{1-6}$-alkoxy, carboxy-$C_{1-6}$-alkoxy-$C_{1-6}$-alkyl, $C_{1-6}$-alkoxy-$C_{1-6}$-alkylcarbonyl, acyl-$C_{1-6}$-alkoxy-$C_{1-6}$-alkyl, (N—$C_{1-6}$-alkyl)-$C_{1-6}$-alkoxycarbonylamino, (N-hydroxy)-$C_{1-6}$-alkylaminocarbonyl-$C_{1-6}$-alkyl, (N-hydroxy)-$C_{1-6}$-alkylaminocarbonyl-$C_{1-6}$-alkoxy, (N-hydroxy)aminocarbonyl-$C_{1-6}$-alkyl, (N-hydroxy)aminocarbonyl-$C_{1-6}$-alkoxy, $C_{1-6}$-alkoxyaminocarbonyl-$C_{1-6}$-alkyl, 6-alkoxyaminocarbonyl-$C_{1-6}$-alkoxy, (N—$C_{1-6}$-alkoxy)-

$C_{1-6}$-alkylaminocarbonyl-$C_{1-6}$-alkyl, (N—$C_{1-6}$-alkoxy)-$C_{1-6}$-alkylaminocarbonyl-$C_{1-6}$-alkoxy, (N-acyl)-$C_{1-6}$-alkoxy-$C_{1-6}$-alkylamino, $C_{1-6}$-alkoxy-$C_{1-6}$-alkylcarbamoyl, (N—$C_{1-6}$-alkyl)-$C_{1-6}$-alkoxy-$C_{1-6}$-alkylcarbamoyl, $C_{1-6}$-alkoxy-$C_{1-6}$-alkylcarbonyl, $C_{1-6}$-alkoxy-$C_{1-6}$-alkylcarbonylamino, (N—$C_{1-6}$-alkyl)-$C_{1-6}$-alkoxy-$C_{1-6}$-alkylcarbonylamino, 1-$C_{1-6}$-alkoxy-$C_{1-6}$-alkylimidazol-2-yl, 1-$C_{1-6}$-alkoxy-$C_{1-6}$-alkyltetrazol-5-yl, 5-$C_{1-6}$-alkoxy-$C_{1-6}$-alkyltetrazol-1-yl, 2-$C_{1-6}$-alkoxy-$C_{1-6}$-alkyl-4-oxoimidazol-1-yl, carbamoyl-$C_{1-6}$-alkyl, carbamoyl-$C_{1-6}$-alkoxy, $C_{1-6}$-alkylcarbamoyl, di-$C_{1-6}$-alkylcarbamoyl, $C_{1-6}$-alkylsulphonyl, $C_{1-6}$-alkylamidinyl, acetamidinyl-$C_{1-6}$-alkyl, O-methyloximyl-$C_{1-6}$-alkyl, O,N-dimethylhydroxylamino-$C_{1-6}$-alkyl, $C_{3-6}$-cycloalkyl-$C_{1-6}$-alkanoyl, aryl-$C_{1-6}$-alkanoyl or heterocyclyl-$C_{1-6}$-alkanoyl, or else pyridyl, pyridyloxy, pyridylthio, pyridylamino, pyridyl-$C_{1-6}$-alkyl, pyridyl-$C_{1-6}$-alkoxy, pyrimidinyl, pyrimidinyloxy, pyrimidinylthio, pyrimidinylamino, pyrimidinyl-$C_{1-6}$-alkyl, pyrimidinyl-$C_{1-6}$-alkoxy, thienyl, thienyl-$C_{1-6}$-alkyl, thienyl-$C_{1-6}$-alkoxy, furyl, furyl-$C_{1-6}$-alkyl or furyl-$C_{1-6}$-alkoxy, each of which is optionally substituted by halogen, $C_{1-6}$-alkyl, $C_{1-6}$-alkoxy or dihydroxy-$C_{1-6}$-alkylaminocarbonyl, piperidinoalkyl, piperidinoalkoxy, piperidinoalkoxyalkyl, morpholinoalkyl, morpholinoalkoxy, morpholinoalkoxyalkyl, piperazinoalkyl, piperazinoalkoxy, piperazinoalkoxyalkyl, [1,2,4]-triazol-1-ylalkyl, [1,2,4]-triazol-1-ylalkoxy, [1,2,4]-triazol-4-ylalkyl, [1,2,4]-triazol-4-ylalkoxy, [1,2,4]-oxadiazol-5-ylalkyl, [1,2,4]-oxadiazol-5-ylalkoxy, 3-methyl-[1,2,4]-oxadiazol-5-ylalkyl, 3-methyl-[1,2,4]-oxadiazol-5-ylalkoxy, 5-methyl-[1,2,4]-oxadiazol-3-ylalkyl, 5-methyl-[1,2,4]-oxadiazol-3-ylalkoxy, tetrazol-1-ylalkyl, tetrazol-1-ylalkoxy, tetrazol-2-ylalkyl, tetrazol-2-ylalkoxy, tetrazol-5-ylalkyl, tetrazol-5-ylalkoxy, 5-methyl-tetrazol-1-ylalkyl, 5-methyl-tetrazol-1-ylalkoxy, thiazol-4-ylalkyl, thiazol-4-ylalkoxy, oxazol-4-ylalkyl, oxazol-4-ylalkoxy, 2-oxo-pyrrolidinylalkyl, 2-oxopyrrolidinylalkoxy, imidazolylalkyl, imidazolylalkoxy, 2-methyl-imidazolylalkyl, 2-methyl-imidazolylalkoxy or N-methylpiperazinoalkyl, N-methylpiperazinoalkoxy, N-methylpiperazinoalkoxyalkyl, dioxolanyl, dioxanyl, dithiolanyl, dithianyl, pyrrolidinyl, piperidinyl, piperazinyl, pyrrolyl, 4-methylpiperazinyl, morpholinyl, thiomorpholinyl, 2-hydroxymethylpyrrolidinyl, 3-hydroxypyrrolidinyl, 3,4-dihydroxypyrrolidinyl, 3-acetamidomethylpyrrolidinyl, 3-$C_{1-6}$-alkoxy-$C_{1-6}$-alkylpyrrolidinyl, 4-hydroxypiperidinyl, 4-oxopiperidinyl, 3,5-dimethylmorpholinyl, 4,4-dioxothiomorpholinyl, 4-oxothiomorpholinyl, 2,6-dimethylmorpholinyl, 2-oxoimidazolidinyl, 2-oxooxazolidinyl, 2-oxopyrrolidinyl, 2-oxo-[1,3]oxazinyl, 2-oxotetrahydropyrimidinyl and the —O—$CH_2CH(OH)CH_2NR_x$ radical where $NR_x$ is a mono- or di-$C_{1-6}$-alkylamino, piperidino, morpholino, piperazino or N-methylpiperazino radical; or (B) $R^6$ is a polycyclic, unsaturated hydrocarbon radical, phenyl substituted by $C_1$-$C_6$-alkylenedioxy, furyl, thienyl, pyridyl, pyrimidyl, indolyl, quinolinyl, pyrazinyl, triazolyl, imidazolyl, benzothiazolyl, pyranyl, tetrahydropyranyl, azetidinyl, morpholinyl, tetrahydroquinolinyl, tetrahydroisoquinolinyl quinazolinyl, quinoxalinyl, isoquinolyl, benzo[b]thienyl, isobenzofuranyl, benzoimidazolyl, 2-oxobenzoimidazolyl, oxazolyl, thiazolyl, pyrrolyl, pyrazolyl, triazinyl, dihydrobenzofuranyl, 2-oxodihydrobenzo[d][1,3]oxazinyl, 4-oxodihydroimidazolyl, 5-oxo-4H[1,2,4]triazinyl, 3-oxo-4H-benzo [1,4]thiazinyl, tetrahydroquinoxalinyl, 1,1,3-trioxodihydro-2H-1$\lambda^6$-benzo[1,4]thiazinyl, 1-oxopyridyl, dihydro-3H-benzo[1,4]oxazinyl, 3,4-dihydro-2H-benzo[1,4]oxazinyl, 2-oxotetrahydrobenzo[e][1,4]diazepinyl, 2-oxodihydrobenzo [e][1,4]diazepinyl, 1H-pyrrolizinyl, phthalazinyl, 1-oxo-3H-isobenzofuranyl, 4-oxo-3H-thieno[2,3-d]pyrimidinyl, 3-oxo-4H-benzo[1,4]oxazinyl, [1,5]naphthyridyl, dihydro-2H-benzo [1,4]thiazinyl, 1,1-dioxodihydro-2H-benzo [1,4]thiazinyl, 2-oxo-1H-pyrido[2,3b][1,4]oxazinyl, dihydro-1H-pyrido[2,3-b][1,4]oxazinyl, 1H-pyrrolo[2,3-b] pyridyl, benzo[1,3]dioxolyl, benzoxazolyl, 2-oxobenzooxazolyl, 2-oxo-1,3-dihydroindolyl, 2,3-dihydroindolyl, indazolyl, benzofuranyl, dioxolanyl, dioxanyl, dithiolanyl, dithianyl, pyrrolidinyl, piperidinyl, piperazinyl, 4-methylpiperazinyl, morpholinyl, thiomorpholinyl, 2-hydroxymethylpyrrolidinyl, 3-hydroxypyrrolidinyl, 3,4-dihydroxypyrrolidinyl, 4-hydroxypiperidinyl, 4-oxopiperidinyl, 3,5-dimethylmorpholinyl, 4,4-dioxothiomorpholinyl, 4-oxothiomorpholinyl, 2,6-dimethylmorpholinyl, tetrahydropyranyl, 2-oxoimidazolidinyl, 2-oxooxazolidinyl, 2-oxopiperidinyl, 2-oxopyrrolidinyl, 2-oxo[1,3]oxazinyl, 2-oxoazepanyl, or 2-oxotetrahydropyrimidinyl;

and salts thereof, preferably pharmaceutically usable salts thereof.

Aryl, and aryl in aryl-$C_0$-$C_4$-alkyl, aryloxy-$C_0$-$C_4$-alkyl, aryl-$C_0$-$C_4$-alkyl-$C_1$-$C_8$-alkoxy and aryloxy-$C_0$-$C_4$-alkyl-$C_1$-$C_8$-alkoxy, contains generally 1-14, preferably 6-10, carbon atoms, and is, for example, phenyl, indenyl, e.g. 2- or 4-indenyl, or naphthyl, e.g. 1- or 2-naphthyl. Preference is given to aryl having 6-10 carbon atoms, in particular phenyl or 1- or 2-naphthyl. The radicals mentioned may be unsubstituted or, for example, mono- or polysubstituted, for example mono- or disubstituted, by $C_1$-$C_8$-alkyl, cyano, halogen, oxo, trifluoromethyl, $C_1$-$C_8$-alkoxy, $C_1$-$C_8$-alkoxy-$C_1$-$C_8$-alkoxy, $C_1$-$C_8$-alkoxy-$C_1$-$C_8$-alkyl, $C_1$-$C_8$-alkoxycarbonyl, aryl or heteroaryl, and the substituent may be in any position, for example in the o-, m- or p-position of the phenyl radical, or in the 3- or 4-position of the 1- or 2-naphthyl radical, and a plurality of identical or different substituents may also be present.

Aryl-$C_0$-$C_4$-alkyl is, for example, phenyl, naphthyl or benzyl.

Examples of substituents on $R^6$ in the definition of heterocyclyl radicals and polycyclic, unsaturated hydrocarbon radicals are $C_1$-$C_6$-alkyl, $C_{3-8}$-cycloalkyl, $C_{3-8}$-cycloalkoxy, $C_{3-8}$-cycloalkoxy-$C_{1-6}$-alkyl, $C_{3-8}$-cycloalkoxy-$C_{1-6}$-alkoxy, $C_1$-$C_6$-alkylamino, di-$C_1$-$C_6$-alkylamino, amino-$C_{1-6}$-alkyl, amino-$C_{2-7}$-alkoxy, polyhalo-$C_{1-6}$-alkyl, especially trifluoromethyl, polyhalo-$C_{2-7}$-alkoxy, nitro, amino, $C_2$-$C_6$-alkenyl, $C_1$-$C_6$-alkoxy, $C_1$-$C_6$-alkanoyloxy, hydroxyl, halogen, oxide, oxo, cyano, carbamoyl, carboxy, $C_1$-$C_6$-alkylenedioxy, phenyl, phenoxy, phenylthio, phenyl-$C_1$-$C_6$-alkyl or phenyl-$C_1$-$C_6$-alkoxy, each of which is optionally substituted by halogen, $C_1$-$C_6$-alkyl, $C_{1-6}$-alkoxy, hydroxyl, $C_1$-$C_6$-alkylamino, di-$C_1$-$C_6$-alkylamino, $C_{1-6}$-alkoxycarbonyl, hydroxy-$C_{1-6}$-alkyl or trifluoromethyl, $C_{1-6}$-alkoxycarbonylphenyl, hydroxy-$C_{1-6}$-alkylphenyl, benzyloxy, pyridylcarbonylamino-$C_{1-6}$-alkyl, $C_{2-6}$-alkenyloxy, $C_{1-6}$-alkoxy-$C_{1-6}$-alkoxy, $C_{1-6}$-alkoxy-$C_{1-6}$-alkoxy-$C_{1-6}$-alkyl, methoxybenzyloxy, hydroxybenzyloxy, phenethyloxy, methylenedioxybenzyloxy, dioxolanyl-$C_{1-6}$-alkoxy, cyclopropyl-$C_{1-6}$-alkyl, cyclopropyl-$C_{1-6}$-alkoxy, hydroxy-$C_{2-7}$-alkoxy, carbamoyloxy-$C_{1-6}$-alkoxy, pyridylcarbamoyloxy-$C_{1-6}$-alkoxy, benzoyloxy-$C_{1-6}$-alkoxy, $C_{1-6}$-alkoxycarbonyl, $C_{1-6}$-alkylcarbonylamino, $C_{1-6}$-alkylcarbonylamino-$C_{1-6}$-alkyl, $C_{1-6}$-alkylcarbonylamino-$C_{2-7}$-alkoxy, (N—$C_{1-6}$-alkyl)-$C_{1-6}$-alkylcarbonylamino-$C_{1-6}$-alkyl, (N—$C_{1-6}$-alkyl)-$C_{1-6}$- alkylcarbonylamino-$C_{2-7}$-alkoxy, $C_{3-8}$-cycloalkylcarbonylamino-$C_{1-6}$-alkyl, $C_{3-8}$-cycloalkylcarbonylamino-$C_{2-7}$-alkoxy, $C_{1-6}$-alkoxy-$C_{1-6}$-alkyl, hydroxy-$C_{1-6}$-alkyl, hydroxy-$C_{2-7}$-alkoxy-$C_{1-6}$-alkyl, hydroxy-$C_{2-7}$-alkoxy-$C_{1-6}$-alkoxy, $C_{1-6}$-alkoxycarbonylamino-$C_{1-6}$-alkyl, $C_{1-6}$-alkoxycarbonylamino-$C_{2-7}$-alkoxy, $C_{1-6}$-alkylaminocarbonylamino-$C_{1-6}$-alkyl, $C_{1-6}$-alkylaminocarbonylamino-$C_{2-7}$-alkoxy, $C_{1-6}$-alkylaminocarbonyl-$C_{1-6}$-alkyl, $C_{1-6}$-alkylaminocarbonyl-$C_{1-6}$-alkoxy, $C_{1-6}$-alkylaminocarbonyl-$C_{1-6}$-alkoxy-$C_{1-6}$-alkyl, di-$C_{1-6}$-alkylaminocarbonyl-$C_{1-6}$-alkyl, di-$C_{1-6}$-alkylaminocarbonyl-$C_{1-6}$-alkoxy, $C_{1-6}$-alkylcarbonyloxy-$C_{1-6}$-alkyl, $C_{1-6}$-alkylcarbonyloxy-$C_{1-6}$-alkoxy, cyano-$C_{1-6}$-alkyl, cyano-$C_{1-6}$-alkoxy, 2-oxooxazolidinyl-$C_{1-6}$-alkyl, 2-oxooxazolidinyl-$C_{1-6}$-alkoxy, $C_{1-6}$-alkoxycarbonyl-$C_{1-6}$-alkyl, $C_{1-6}$-alkoxycarbonyl-$C_{1-6}$-alkoxy, $C_{1-6}$-alkylsulphonylamino-$C_{1-6}$-alkyl, $C_{1-6}$-alkylsulphonylamino-$C_{2-7}$-alkoxy, (N—$C_{1-6}$-alkyl)-$C_{1-6}$-alkylsulphonylamino-$C_{1-6}$-alkyl, (N—$C_{1-6}$-alkyl)-$C_{1-6}$-alkylsulphonylamino-$C_{2-7}$-alkoxy, $C_{1-6}$-alkylamino-$C_{1-6}$-alkyl, $C_{1-6}$-alkylamino-$C_{2-7}$-alkoxy, di-$C_{1-6}$-alkylamino-$C_{1-6}$-alkyl, di-$C_{1-6}$-alkylamino-$C_{2-7}$-alkoxy, $C_{1-6}$-alkylsulphonyl-$C_{1-6}$-alkyl, $C_{1-6}$-alkylsulphonyl-$C_{1-6}$-alkoxy, carboxy-$C_{1-6}$-alkyl, carboxy-$C_{1-6}$-alkoxy, carboxy-$C_{1-6}$-alkoxy-$C_{1-6}$-alkyl, $C_{1-6}$-alkoxy-$C_{1-6}$-alkylcarbonyl, acyl-$C_{1-6}$-alkoxy-$C_{1-6}$-alkyl, (N—$C_{1-6}$-alkyl)-$C_{1-6}$-alkoxycarbonylamino, (N-hydroxy)-$C_{1-6}$-alkylaminocarbonyl-$C_{1-6}$-alkyl, (N-hydroxy)-$C_{1-6}$-alkylaminocarbonyl-$C_{1-6}$-alkoxy, (N-hydroxy)aminocarbonyl-$C_{1-6}$-alkyl, (N-hydroxy)aminocarbonyl-$C_{1-6}$-alkoxy, $C_{1-6}$-alkoxyaminocarbonyl-$C_{1-6}$-alkyl, 6-alkoxy-aminocarbonyl-$C_{1-6}$-alkoxy, (N—$C_{1-6}$-alkoxy)-$C_{1-6}$-alkylaminocarbonyl-$C_{1-6}$-alkyl, (N—$C_{1-6}$-alkoxy)-$C_{1-6}$-alkylaminocarbonyl-$C_{1-6}$-alkoxy, (N-acyl)-$C_{1-6}$-alkoxy-$C_{1-6}$-alkylamino, $C_{1-6}$-alkoxy-$C_{1-6}$-alkylcarbamoyl, (N—$C_{1-6}$-alkyl)-$C_{1-6}$-alkoxy-$C_{1-6}$-alkylcarbamoyl, $C_{1-6}$-alkoxy-$C_{1-6}$-alkylcarbonyl, $C_{1-6}$-alkoxy-$C_{1-6}$-alkylcarbonylamino, (N—$C_{1-6}$-alkyl)-$C_{1-6}$-alkoxy-$C_{1-6}$-alkylcarbonylamino, 1-$C_{1-6}$-alkoxy-$C_{1-6}$-alkylimidazol-2-yl, 1-$C_{1-6}$-alkoxy-$C_{1-6}$-alkyltetrazol-5-yl, 5-$C_{1-6}$-alkoxy-$C_{1-6}$-alkyltetrazol-1-yl, 2-$C_{1-6}$-alkoxy-$C_{1-6}$-alkyl-4-oxoimidazol-1-yl, carbamoyl-$C_{1-6}$-alkyl, carbamoyl-$C_{1-6}$-alkoxy, $C_{1-6}$-alkylcarbamoyl, di-$C_{1-6}$-alkylcarbamoyl, $C_{1-6}$-alkylsulphonyl, $C_{1-6}$-alkylamidinyl, acetamidinyl-$C_{1-6}$-alkyl, O-methyloximyl-$C_{1-6}$-alkyl, O,N-dimethylhydroxylamino-$C_{1-6}$-alkyl, $C_{3-6}$-cycloalkyl-$C_{1-6}$-alkanoyl, aryl-$C_{1-6}$-alkanoyl or heterocyclyl-$C_{1-6}$-alkanoyl; or else pyridyl, pyridyloxy, pyridylthio, pyridylamino, pyridyl-$C_{1-6}$-alkyl, pyridyl-$C_{1-6}$-alkoxy, pyrimidinyl, pyrimidinyloxy, pyrimidinylthio, pyrimidinylamino, pyrimidinyl-$C_{1-6}$-alkyl, pyrimidinyl-$C_{1-6}$-alkoxy, thienyl, thienyl-$C_{1-6}$-alkyl, thienyl-$C_{1-6}$-alkoxy, furyl, furyl-$C_{1-6}$-alkyl or furyl-$C_{1-6}$-alkoxy, each of which is optionally substituted by halogen, $C_{1-6}$-alkyl, $C_{1-6}$-alkoxy or dihydroxy-$C_{1-6}$-alkylaminocarbonyl.

The term polycyclic, unsaturated hydrocarbon radical denotes radicals such as naphthyl, cyclohexenophenyl, indanyl and acenaphthyl, for example.

The term heterocyclyl denotes mono- or bicyclic, saturated and unsaturated heterocyclic radicals which have from 1 to 4 nitrogen and/or 1 or 2 sulphur or oxygen atoms and may be mono- or polysubstituted, especially mono-, di- or trisubstituted. In addition, the term encompasses the above oxo-substituted radicals. Examples of heterocyclyl radicals are phenyl substituted by $C_1$-$C_6$-alkylenedioxy, pyridyl, thienyl, pyrazinyl, triazolyl, imidazolyl, benzothiazolyl, furyl, pyranyl, pyrimidinyl, quinazolinyl, quinolyl, quinoxalinyl, isoquinolyl, benzo[b]thienyl, isobenzofuranyl, benzoimidazolyl, 2-oxobenzoimidazolyl, oxazolyl, thiazolyl, indolyl, pyrrolyl, pyrazolyl, triazinyl, dihydrobenzofuranyl, 2-oxodihydrobenzo[d][1,3]oxazinyl, 4-oxodihydroimidazolyl, 5-oxo-4H-[1,2,4]triazinyl, 3-oxo-4H-benzo[1,4]thiazinyl, tetrahydroquinoxalinyl, tetrahydroquinolinyl, tetrahydroisoquinolinyl 1,1,3-trioxodihydro-2H-1$\lambda^6$-benzo[1,4]thiazinyl, 1-oxopyridyl, dihydro-3H-benzo[1,4]oxazinyl, 2-oxotetrahydrobenzo [e][1,4]diazepinyl, 2-oxodihydrobenzo[e][1,4]diazepinyl, 1H-pyrrolizinyl, phthalazinyl, 1-oxo-3H-isobenzofuranyl, 4-oxo-3H-thieno[2,3-d]pyrimidinyl, 3,4-dihydro-2H-benzo[1,4]oxazinyl, 3-oxo-4H-benzo[1,4]oxazinyl, [1,5]naphthyridyl, dihydro-2H-benzo[1,4]thiazinyl, 1,1-dioxodihydro-2H-benzo[1,4]thiazinyl, 2-oxo-1H-pyrido[2,3-b][1,4]oxazinyl, dihydro-1H-pyrido [2,3-b][1,4]oxazinyl, 1H-pyrrolo[2,3-b]pyridyl, benzo[1,3]dioxolyl, benzooxazolyl, 2-oxobenzooxazolyl, 2-oxo-1,3-dihydroindolyl, 2,3-dihydroindolyl, indazolyl, pyrrolo [3,2-c]pyridinyl, pyrrolo[2,3-c]pyridinyl, pyrrolo[3,2-b]pyridinyl, [1,2,3]triazolo[1,5-a]pyridinyl, [1,2,4]triazolo[4,3-a]pyridinyl, imidazo[1,2-a]pyrimidinyl, imidazo[1,5-a]pyridinyl or benzofuranyl. Examples of saturated heterocyclyl radicals are azepanyl, azetidinyl, aziridinyl, dioxolanyl, dioxanyl, dithiolanyl, dithianyl, oxepanyl, pyrrolidinyl, 1-methylpiperidinyl, 1-methylpyrrolidinyl, piperidinyl, piperazinyl, 4-methylpiperazinyl, morpholinyl, thiomorpholinyl, 2-hydroxymethylpyrrolidinyl, 3-hydroxypyrrolidinyl, 3,4-dihydroxypyrrolidinyl, 4-hydroxypiperidinyl, 4-oxopiperidinyl, 3,5-dimethylmorpholinyl, 4,4-dioxothiomorpholinyl, 4-oxothiomorpholinyl, 2,6-dimethylmorpholinyl, tetrahydrofuranyl, tetrahydropyranyl, tetrahydrothiophenyl, tetrahydrothiopyranyl, 2-oxoimidazolidinyl, 2-oxooxazolidinyl, 2-oxopiperidinyl, 2-oxopyrrolidinyl, 2-oxo[1,3]oxazinyl, 2oxoazepanyl or 2-oxotetrahydropyrimidinyl.

In the case of $R^6$, the heterocyclyl radicals may additionally also be substituted by heterocyclylalkyl, heterocyclylalkoxy, heterocyclylalkoxyalkyl or heterocyclyl, for example piperidinoalkyl, piperidinoalkoxy, piperidinoalkoxyalkyl, morpholinoalkyl, morpholinoalkoxy, morpholinoalkoxyalkyl, piperazinoalkyl, piperazinoalkoxy, piperazinoalkoxyalkyl, [1,2,4]-triazol-1-ylalkyl, [1,2,4]-triazol-1-ylalkoxy, [1,2,4]-triazol-4-ylalkyl, [1,2,4]-triazol-4-ylalkoxy, [1,2,4]-oxadiazol-5-ylalkyl, [1,2,4]-oxadiazol-5-ylalkoxy, 3-methyl [1,2,4]oxadiazol-5-ylalkyl, 3-methyl[1,2,4]oxadiazol-5-ylalkoxy, 5-methyl[1,2,4]oxadiazol-3-ylalkyl, 5-methyl[1,2,4]oxadiazol-3-ylalkoxy, tetrazol-1-ylalkyl, tetrazol-1-ylalkoxy, tetrazol-2-ylalkyl, tetrazol-2-ylalkoxy, tetrazol-5-ylalkyl, tetrazol-5-ylalkoxy, 5-methyltetrazol-1-ylalkyl, 5-methyltetrazol-1-ylalkoxy, thiazol-4-ylalkyl, thiazol-4-ylalkoxy, oxazol-4-ylalkyl, oxazol-4-ylalkoxy, 2-oxopyrrolidinylalkyl, 2-oxopyrrolidinylalkoxy, imidazolylalkyl, imidazolylalkoxy, 2-methylimidazolylalkyl, 2-methylimidazolylalkoxy or N-methylpiperazinoalkyl, N-methylpiperazinoalkoxy, N-methylpiperazinoalkoxyalkyl, dioxolanyl, dioxanyl, dithiolanyl, dithianyl, pyrrolidinyl, piperidinyl, piperazinyl, pyrrolyl, 4-methylpiperazinyl, morpholinyl, thiomorpholinyl, 2-hydroxymethylpyrrolidinyl, 3-hydroxypyrrolidinyl, 3,4-dihydroxypyrrolidinyl, 3-acetamidomethylpyrrolidinyl, 3-$C_{1-6}$-alkoxy-$C_{1-6}$-alkylpyrrolidinyl, 4-hydroxypiperidinyl, 4-oxopiperidinyl, 3,5-dimethylmorpholinyl, 4,4-dioxothiomorpholinyl, 4-oxothiomorpholinyl, 2,6-dimethylmorpholinyl, 2-oxoimidazolidinyl, 2-oxooxazolidinyl, 2-oxopyrrolidinyl, 2-oxo[1,3]oxazinyl, 2-oxotetrahydropyrimidinyl or by the —O—$CH_2CH(OH)CH_2NR_x$ radical where $NR_x$ is a mono- or di-$C_{1-6}$-alkylamino, piperidino, morpholino, piperazino or N-methylpiperazino radical.

The term polyhydroxyalkyl denotes $C_1$-$C_7$-alkyl radicals which may be substituted by 2-6 hydroxyl groups, for example glyceryl, arabityl, sorbityl, etc.

Heterocyclyl and heterocyclyloxy in heterocyclyl-$C_0$-$C_4$-alkyl, heterocyclyloxy-$C_0$-$C_4$-alkyl, heterocyclyl-$C_0$-$C_4$-alkyl-$C_1$-$C_8$-alkoxy and heterocyclyloxy-$C_0$-$C_4$-alkyl-$C_1$-$C_8$-alkoxy having from 5 to 7 ring atoms in the heterocyclyl ring which contains one ring nitrogen atom and may contain one further ring heteroatom selected from oxygen, sulphur or nitrogen, is, for example, pyridinyl or imidazolyl which are each unsubstituted or substituted by $C_1$-$C_8$-alkyl, $C_{1-6}$-alkoxy-$C_{1-6}$-alkyl, $C_{1-6}$-alkoxy-$C_{1-6}$-alkoxy, halogen, cyano, oxide, oxo, trifluoromethyl, $C_1$-$C_8$-alkoxy, $C_1$-$C_8$-alkoxycarbonyl, aryl or heterocyclyl.

Heterocyclyl-$C_0$-$C_4$-alkyl is, for example, pyridinyl, methylenepyridinyl or imidazolyl.

Heterocyclyl which is bonded via a ring nitrogen atom and has from 4 to 8 ring atoms has in particular from 5 to 7 ring atoms and may have 1 or 2 fused-on phenyl or cycloalkyl radicals, or else be present as the spiro compound. Examples include pyrrolidino, piperidino, morpholino, 9-[3.3.1]non-9-yl, 1-azepan-1-yl, 2,8-diazaspiro[4.5]dec-8-yl, octahydroisoindol-2-yl, 4-azatricyclo[5.2.1.0$^{2,6}$]dec-4-yl, 3-azabicyclo[3.2.1]oct-3-yl, 3,7-diazabicyclo[3.3.1]non-3-yl, 3-azabicyclo[3.3.1]non-3-yl, 8-azabicyclo[3.2.1]oct-8-yl, 3-azabicyclo[3.2.2]non-3-yl and tetrahydro-1H-1-benz[6,7-b]azepin-1-yl.

In the case of nitrogen heterocycles, the heterocyclyl radicals may be bonded via the nitrogen or via a ring carbon.

Halogen is, for example, fluorine, chlorine, bromine or iodine, preferably fluorine or chlorine.

Polyhalo-$C_1$-$C_4$-alkyl is, for example, di-, tri- or tetrahalo-$C_1$-$C_4$-alkyl, such as trifluoromethyl.

$C_3$-$C_8$-Cycloalkanoyl is preferably 3-, 5- or 6-membered cycloalkyl-C(=O)—.

3- to 8-membered cycloalkoxy is preferably 3-, 5- or 6-membered cycloalkoxy, such as cyclopropyloxy cyclopentyloxy cyclohexyloxy.

3- to 8-membered cycloalkyl is preferably 3-, 5- or 6-membered cycloalkyl, such as cyclopropyl, cyclopentyl, cyclohexyl.

Amino-$C_2$-$C_4$-alkoxy is, for example, 2-aminoethoxy, and also 3-aminopropyloxy or 4-aminobutyloxy.

Amino-$C_1$-$C_4$-alkyl is, for example, 2-aminoethyl, 3-aminopropyl or 4-aminobutyl.

Carbamoyl-$C_0$-$C_8$-alkyl is, for example, carbamoyl, carbamoylmethyl, 2-carbamoylethyl, 3-carbamoylpropyl, 2-(3-carbamoyl)propyl, 2-carbamoylpropyl, 3-(1-carbamoyl)propyl, 2-(2-carbamoyl)propyl, 2-carbamoyl-2-methylpropyl, 4-carbamoylbutyl, 1-carbamoylbutyl, 1-(1-carbamoyl-2-methyl)butyl, 3-(4-carbamoyl-2-methyl)butyl.

Carboxy-$C_1$-$C_4$-alkoxy is, for example, carboxymethoxy, 2-carboxyethoxy, 2- or 3-carboxypropyloxy or 4-carboxybutyloxy, especially carboxymethoxy.

Carboxy-$C_1$-$C_4$-alkyl is, for example, carboxymethyl, 2-carboxyethyl, 2- or 3-carboxypropyl, 2-carboxy-2-methylpropyl, 2-carboxy-2-ethylbutyl or 4-carboxybutyl, especially carboxymethyl.

Cyano-$C_1$-$C_4$-alkoxy is, for example, cyanomethoxy, 2-cyanoethoxy 2- or 3-cyanopropyloxy or 4-cyanobutyloxy, especially cyanomethoxy Cyano-$C_1$-$C_4$-alkyl is, for example, cyanomethyl, 2-cyanoethyl, 2- or 3-cyanopropyl, 2-cyano-2-methylpropyl, 2-cyano-2-ethylbutyl or 4-cyanobutyl, especially cyanomethyl.

N,N-Di-$C_1$-$C_4$-alkylamino is, for example, dimethylamino, N-methyl-N-ethylamino, diethylamino, N-methyl-N-propylamino or N-butyl-N-methylamino.

N,N-Di-$C_1$-$C_4$-alkylamino-$C_2$-$C_4$-alkoxy is 2-dimethylaminoethoxy, 3-dimethylaminopropyloxy, 4-dimethylaminobutyloxy, 2-diethylaminoethoxy, 2-(N-methyl-N-ethylamino)ethoxy or 2-(N-butyl-N-methylamino)ethoxy.

N,N-Di-$C_1$-$C_4$-alkylamino-$C_1$-$C_4$-alkyl is, for example, 2-dimethylaminoethyl, 3-dimethylaminopropyl, 4-dimethylaminobutyl, 2-diethylaminoethyl, 2-(N-methyl-N-ethylamino)ethyl or 2-(N-butyl-N-methylamino)ethyl.

N,N-Di-$C_1$-$C_4$-alkylcarbamoyl-$C_1$-$C_4$-alkoxy is, for example, methyl or dimethylcarbamoyl-$C_1$-$C_4$-alkoxy, such as N-methyl-, N-butyl- or N,N-dimethylcarbamoylmethoxy, 2-(N-methylcarbamoyl)ethoxy, 2-(N-butylcarbamoyl)ethoxy, 2-(N,N-dimethylcarbamoyl)ethoxy, 3-(N-methylcarbamoyl)propyloxy, 3-(N-butylcarbamoyl)propyloxy, 3-(N,N-dimethylcarbamoyl)propyloxy or 4-(N-methylcarbamoyl)butyloxy, 4-(N-butylcarbamoyl)butyloxy or 4-(N,N-dimethylcarbamoyl)butyloxy, especially N-methyl-, N-butyl- or N,N-dimethylcarbamoylmethoxy.

N,N-Di-$C_1$-$C_4$-alkylcarbamoyl-$C_1$-$C_4$-alkyl is, for example, 2-dimethylcarbamoylethyl, 3-dimethylcarbamoylpropyl, 2dimethylcarbamoylpropyl, 2-(dimethylcarbamoyl)-2-methylpropyl or 2-(1-dimethylcarbamoyl)-3-methylbutyl.

Optionally partially hydrogenated pyridyl- or N-oxidopyridyl-$C_1$-$C_4$-alkoxy is, for example, pyridyl- or N-oxidopyridylmethoxy, 2-pyridylethoxy 2- or 3-pyridylpropyloxy or 4-pyridylbutyloxy, in particular 3- or 4-pyridylmethoxy.

Optionally partially hydrogenated pyridyl- or N-oxidopyridyl-$C_1$-$C_4$-alkyl is, for example, pyridyl- or N-oxidopyridylmethyl, 2-pyridylethyl, 2- or 3-pyridylpropyl or 4-pyridylbutyl, in particular 3- or 4-pyridylmethyl.

Halo-$C_2$-$C_8$-(hydroxy)alkoxy is, for example, halo-$C_2$-$C_4$-(hydroxy)alkoxy, such as 3-halo-, such as 3-chloro-2-hydroxypropyloxy.

Hydroxy-$C_2$-$C_8$-alkoxy is, for example, hydroxy-$C_2$-$C_4$-alkoxy such as 2-hydroxybutyloxy, 3-hydroxypropyloxy or 4-hydroxybutyloxy.

Hydroxy-$C_2$-$C_8$-alkyl is, for example, hydroxy-$C_2$-$C_4$-alkyl, such as 2-hydroxyethyl, 3-hydroxypropyl or 4-hydroxybutyl.

Morpholino-$C_1$-$C_4$-alkoxy may be N-oxidized and is, for example, 1-morpholinoethoxy, 3-morpholinopropyloxy or 1-(morpholino-2-methyl)propyloxy.

Morpholino-$C_1$-$C_4$-alkyl may be N-oxidized and is, for example, morpholinomethyl, 2-morpholinoethyl, 3-morpholinopropyl or 1- or 2-(4-morpholino)butyl.

$C_1$-$C_8$-Alkanoyl is in particular $C_2$-$C_6$-alkanoyl, such as acetyl, propionyl, butyryl, isobutyryl or pivaloyl.

N—$C_1$-$C_4$-Alkanoylamino-$C_1$-$C_4$-alkyl is, for example, N—$C_1$-$C_4$-alkanoylamino-$C_1$-$C_4$-alkyl, such as 2-acetaminoethyl.

$C_1$-$C_8$-Alkanoyl-$C_2$-$C_4$-alkoxy (oxo-$C_2$-$C_8$-alkoxy) bears the $C_1$-$C_8$-alkanoyl group in a position higher than the α-position and is, for example, 4-acetylbutoxy.

$C_1$-$C_8$-Alkanoyloxy-$C_1$-$C_4$-alkyl bears the $C_1$-$C_8$-alkanoyloxy group in a position higher than the α-position and is, for example, 4-acetoxybutyl.

$C_1$-$C_8$-Alkanesulphonyl-$C_1$-$C_4$-(hydroxy)alkoxy is, for example, 3-methanesulphonyl-2-hydroxypropyloxy.

$C_1$-$C_8$-Alkanesulphonyl-$C_1$-$C_4$-alkoxy is, for example, methanesulphonylmethoxy or 3-methanesulphonyl-2-hydroxypropyloxy.

$C_1$-$C_8$-Alkanesulphonylamino-$C_2$-$C_4$-alkoxy is, for example, 2-ethanesulphonylaminoethoxy, 3-ethanesulphonylaminopropyloxy or 3-(1,1-dimethylethanesulphonylamino)propyloxy.

$C_1$-$C_4$-Alkanesulphonylamino-$C_1$-$C_4$-alkyl is, for example, ethanesulphonylaminomethyl, 2-ethanesulphonylaminoethyl, 3-ethanesulphonylaminopropyl or 3-(1,1-dimethylethanesulphonylamino)propyl.

$C_1$-$C_8$-Alkanesulphonyl-$C_1$-$C_4$-alkyl is, for example, ethanesulphonylmethyl, 2-ethanesulphonylethyl, 3-ethanesulphonylpropyl or 3-(1,1-dimethylethanesulphonyl)propyl.

$C_2$-$C_8$-alkenyloxy is, for example, allyloxy.

$C_2$-$C_8$-Alkenyloxy-$C_1$-$C_4$-alkoxy is, for example, allyloxymethoxy.

$C_2$-$C_8$-Alkenyloxy-$C_1$-$C_4$-alkyl is, for example, allyloxymethyl.

$C_1$-$C_8$-Alkoxy is, for example, $C_1$-$C_5$-alkoxy such as methoxy, ethoxy, propyloxy, isopropyloxy, butyloxy, isobutyloxy, sec-butyloxy, tert-butyloxy or pentyloxy, but may also be a hexyloxy or heptyloxy group.

$C_1$-$C_8$-Alkoxycarbonyl is preferably $C_2$-$C_5$-alkoxycarbonyl such as methoxycarbonyl, ethoxycarbonyl, propyloxycarbonyl, isopropyloxycarbonyl, butyloxycarbonyl, isobutyloxycarbonyl, sec-butyloxycarbonyl or tert-butyloxycarbonyl.

$C_1$-$C_8$-Alkoxycarbonylamino-$C_2$-$C_8$-alkoxy is preferably $C_2$-$C_5$-alkoxycarbonylamino-$C_2$-$C_8$-alkoxy such as methoxycarbonylamino-$C_2$-$C_8$-alkoxy, ethoxycarbonylamino-$C_2$-$C_8$-alkoxy, propyloxycarbonylamino-$C_2$-$C_8$-alkoxy, isopropyloxycarbonylamino-$C_2$-$C_8$-alkoxy, butyloxycarbonylamino-$C_2$-$C_8$-alkoxy, isobutyloxycarbonylamino-$C_2$-$C_8$-alkoxy, sec-butyloxycarbonylamino-$C_2$-$C_8$-alkoxy or tert-butyloxycarbonylamino-$C_2$-$C_8$-alkoxy in which $C_2$-$C_8$-alkoxy is, for example, ethoxy, propyloxy, butyloxy, pentyloxy or hexyloxy.

$C_1$-$C_8$-Alkoxycarbonylamino-$C_2$-$C_8$-alkyl is preferably $C_2$-$C_5$-alkoxycarbonylamino-$C_2$-$C_8$-alkyl such as methoxycarbonylamino-$C_2$-$C_8$-alkyl, ethoxycarbonylamino-$C_2$-$C_8$-alkyl, propyloxycarbonylamino-$C_2$-$C_8$-alkyl, isopropyloxycarbonylamino-$C_2$-$C_8$-alkyl, butyloxycarbonylamino-$C_2$-$C_8$-alkyl, isobutyloxycarbonylamino-$C_2$-$C_8$-alkyl, sec-butyloxycarbonylamino-$C_2$-$C_8$-alkyl or tert-butyloxycarbonylamino-$C_2$-$C_8$-alkyl, in which $C_2$-$C_8$-alkyl is, for example, ethyl, propyl, butyl, pentyl or hexyl.

$C_1$-$C_4$-Alkoxycarbonyl-$C_1$-$C_4$-alkoxy is, for example, methoxycarbonyl- or ethoxycarbonylmethoxy, 2-methoxycarbonyl- or 2-ethoxycarbonylethoxy, 2- or 3-methoxycarbonyl- or 2- or 3-ethoxycarbonylpropyloxy or 4-methoxycarbonyl- or 4-ethoxycarbonylbutyloxy, in particular methoxycarbonyl- or ethoxycarbonylmethoxy or 3-methoxycarbonyl- or 3-ethoxycarbonylpropyloxy.

$C_1$-$C_4$-Alkoxycarbonyl-$C_1$-$C_4$-alkyl is, for example, methoxycarbonyl- or ethoxycarbonylmethyl, 2-methoxycarbonyl- or 2-ethoxycarbonylethyl, 3-methoxycarbonyl- or 3-ethoxycarbonylpropyl or 4-ethoxycarbonylbutyl.

$C_1$-$C_4$-Alkoxy-$C_2$-$C_4$-alkenyl is, for example, 4-methoxybut-2-enyl.

$C_1$-$C_8$-Alkoxy-$C_1$-$C_8$-alkoxy is, for example, 2-methoxy-, 2-ethoxy- or 2-propyloxyethoxy, 3-methoxy- or 3-ethoxypropyloxy or 4-methoxybutyloxy, in particular 3-methoxypropyloxy or 4-methoxybutyloxy.

$C_1$-$C_6$-Alkoxy-$C_1$-$C_6$-alkoxy-$C_1$-$C_6$-alkyl is, for example, $C_1$-$C_4$-alkoxy-$C_1$-$C_4$-alkoxy-$C_1$-$C_4$-alkyl, such as 2-methoxy-, 2-ethoxy- or 2-propyloxyethoxymethyl, 2-(2-methoxy-, 2-ethoxy- or 2-propyloxyethoxy)ethyl, 3-(3-methoxy- or 3-ethoxypropyloxy)propyl or 4-(2-methoxybutyloxy)butyl, in particular 2-(3-methoxypropyloxy)ethyl or 2-(4-methoxybutyloxy)ethyl.

$C_1$-$C_4$-Alkoxy-$C_1$-$C_4$-alkyl is, for example, ethoxymethyl, propyloxymethyl, butyloxymethyl, 2-methoxy-, 2-ethoxy- or 2-propyloxyethyl, 3-methoxy- or 3-ethoxypropyl or 4-methoxybutyl, in particular 3-methoxypropyl or 4-methoxybutyl.

$C_1$-$C_8$-Alkyl may be straight-chain or branched and is, for example, methyl, ethyl, propyl, isopropyl, butyl, isobutyl, sec-butyl, tert-butyl, or a pentyl, hexyl or heptyl group.

$C_1$-$C_4$-Alkylamino-$C_2$-$C_4$-alkoxy is, for example, 2-methylamino-, 2-ethylamino-, 2-propylamino- or 2-butylaminoethoxy, 3-ethylamino- or 3-propylaminopropyloxy or 4-methylaminobutoxy.

$C_1$-$C_4$-Alkylamino-$C_1$-$C_4$-alkyl is, for example, propylaminomethyl, 2-methylamino-, 2-ethylamino-, 2-propylamino- or 2-butylaminoethyl, 3-ethylamino- or 3-propylaminopropyl, or 4-methylaminobutyl.

N—$C_1$-$C_8$-Alkylcarbamoyl-$C_1$-$C_4$-alkoxy is, for example, methyl- or dimethylcarbamoyl-$C_1$-$C_4$-alkoxy, for example methylcarbamoylmethoxy, 2-methylcarbamoylethoxy or 3-methylcarbamoylpropyloxy.

$C_1$-$C_4$-Alkylenedioxy is, for example, methylenedioxy or ethylenedioxy, but may also be 1,3- or 1,2-propylenedioxy.

$C_1$-$C_4$-Alkylthio-$C_1$-$C_4$-(hydroxy)alkoxy is, for example, 2-hydroxy-3-methylthiopropyloxy.

$C_1$-$C_4$-Alkylthio-$C_1$-$C_4$-alkoxy is, for example, methylthio-$C_1$-$C_4$-alkoxy, e.g. methylthiomethoxy, 2-methylthioethoxy or 3-methylthiopropyloxy.

$C_1$-$C_4$-Alkylthio-$C_1$-$C_4$-alkyl is, for example, methylthio-$C_1$-$C_4$-alkyl, e.g. methylthiomethyl, 2-methylthioethyl or 3-methylthiopropyl.

N'-$C_2$-$C_8$-Alkanoylpiperazino-$C_1$-$C_4$-alkyl is, for example, 4-acetylpiperazinomethyl.

N'-$C_1$-$C_4$-Alkylpiperazino-$C_1$-$C_4$-alkyl is 4-methylpiperazinomethyl.

Piperazino-$C_1$-$C_4$-alkyl is, for example, piperazinomethyl, 2-piperazinoethyl or 3-piperazinopropyl.

Piperidino-$C_1$-$C_4$-alkoxy is, for example, piperidinomethoxy, 2-piperidinoethoxy or 3-piperidinopropyloxy Piperidino-$C_1$-$C_4$-alkyl is, for example, piperidinomethyl, 2-piperidinoethyl or 3-piperidinopropyl.

Pyrrolidino-$C_2$-$C_4$-alkoxy is, for example, 2-pyrrolidinoethoxy or 3-pyrrolidinopropyloxy.

Pyrrolidino-$C_1$-$C_4$-alkyl is, for example, pyrrolidino-$C_1$-$C_4$-alkyl, such as pyrrolidinomethyl, 2-pyrrolidinoethyl or 3-pyrrolidinopropyl.

S,S-Dioxothiomorpholino-$C_1$-$C_4$-alkyl is, for example, S,S-dioxothiomorpholinomethyl or 2-(S,S-dioxo)thiomorpholinoethyl.

S-Oxothiomorpholino-$C_1$-$C_4$-alkyl is, for example, S-oxothiomorpholinomethyl or 2-(S-oxo)thiomorpholinoethyl.

Thiazolyl-$C_1$-$C_4$-alkoxy is, for example, thiazolylmethoxy, 2-thiazolylethoxy or 3-thiazolylpropyloxy.

Thiomorpholino-$C_1$-$C_4$-alkyl or S,S-dioxothiomorpholino-$C_1$-$C_4$-alkyl is, for example, thiomorpholino-$C_1$-$C_4$-alkyl such as -methyl or -ethyl, or S,S-dioxothiomorpholino-$C_1$-$C_4$-alkyl, such as -methyl or -ethyl.

Depending on the presence of asymmetric carbon atoms, the inventive compounds may be in the form of isomer mixtures, especially as racemates, or in the form of pure isomers, especially of optical antipodes.

Salts of compounds having salt-forming groups are in particular acid addition salts, salts with bases or, in the presence of a plurality of salt-forming groups, in some cases also mixed salts or internal salts.

Salts are primarily the pharmaceutically usable or nontoxic salts of compounds of the formula (I).

Such salts are formed, for example, from compounds of the formula (I) with an acidic group, for example a carboxyl or sulpho group, and are, for example, the salts thereof with suitable bases, such as nontoxic metal salts derived from metals of group Ia, Ib, IIa and IIb of the Periodic Table of the Elements, for example alkali metal, in particular lithium, sodium or potassium salts, alkaline earth metal salts, for example magnesium or calcium salts, and also zinc salts or ammonium salts, including those salts which are formed with organic amines, such as optionally hydroxy-substituted mono-, di- or trialkylamines, in particular mono-, di- or tri(lower alkyl)amines, or with quaternary ammonium bases, for example methyl-, ethyl-, diethyl- or triethylamine, mono-, bis- or tris(2-hydroxy(lower alkyl))amines, such as ethanol-, diethanol- or triethanolamine, tris(hydroxymethyl)methylamine or 2-hydroxy-tert-butylamine, N,N-di(lower alkyl)-N-(hydroxy(lower alkyl))amines, such as N,N-dimethyl-N-(2-hydroxyethyl)amine, or N-methyl-D-glucamine, or quaternary ammonium hydroxides, such as tetra-butylammonium hydroxide. The compounds of the formula (I) having a basic group, for example an amino group, may form acid addition salts, for example with suitable inorganic acids, e.g. hydrohalic acid such as hydrochloric acid, hydrobromic acid, sulphuric acid with replacement of one or both protons, phosphoric acid with replacement of one or more protons, e.g. orthophosphoric acid or metaphosphoric acid, or pyrophosphoric acid with replacement of one or more protons, or with organic carboxylic, sulphonic, sulpho or phosphonic acids or N-substituted sulphamic acids, e.g. acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid, isonicotinic acid, and also amino acids, for example the α-amino acids mentioned above, and also methanesulphonic acid, ethanesulphonic acid, 2-hydroxyethanesulphonic acid, ethane-1,2-disulphonic acid, benzenesulphonic acid, 4-toluenesulphonic acid, naphthalene-2-sulphonic acid, 2- or 3-phosphoglycerate, glucose-6-phosphate, N-cyclohexylsulphamic acid (with formation of cyclamates) or with other acidic organic compounds such as ascorbic acid. Compounds of the formula (I) with acidic and basic groups may also form internal salts.

For the isolation and purification, pharmaceutically unsuitable salts may also find use.

The compounds of the formula (I) and the pharmaceutically usable salts thereof, have inhibiting action on the natural enzyme renin. The latter passes from the kidneys into the blood and there brings about the cleavage of angiotensinogen to form the decapeptide angiotensin I which is then cleaved in the lung, the kidneys and other organs to the octapeptide angiotensin II. Angiotensin II increases the blood pressure both directly by arterial constriction and indirectly by the release of the hormone aldosterone which inhibits the release of the sodium ion from the adrenal glands, which is associated with a rise in the extracellular liquid volume. This rise can be attributed to the action of angiotensin II itself or of the heptapeptide angiotensin III formed therefrom as a cleavage product. Inhibitors of the enzymatic activity of renin bring about a reduction in the formation of angiotensin I and, as a consequence thereof, the formation of a smaller amount of angiotensin II. The reduced concentration of this active peptide hormone is the immediate cause of the hypotensive action of renin inhibitors.

One experimental method of detecting the action of renin inhibitors is by means of in vitro tests, in which the reduction of the formation of angiotensin I in different systems (human plasma, purified human renin together with synthetic or natural renin substrate) is measured. One in vitro test which is used is the one according to Nussberger et al. (1987) J. Cardiovascular Pharmacol., Vol. 9, p. 39-44 which follows. This test measures the formation of angiotensin I in human plasma. The amount of angiotensin I formed is determined in a subsequent radioimmunoassay. Which action inhibitors have on the formation of angiotensin I is tested in this system by the addition of different concentrations of these substances. The $IC_{50}$ refers to that concentration of the particular inhibitor which reduces the formation of angiotensin I by 50%. The compounds of the present invention exhibit inhibiting actions in the in vitro systems at minimum concentrations of about $10^{-3}$ to about $10^{-10}$ mol/l.

In salt-depleted animals, renin inhibitors bring about a blood pressure decrease. Human renin differs from renin of other species. To test inhibitors of human renin, primates (marmosets, *Callithrix jacchus*) are used, because human renin and primate renin are substantially homologous in the enzymatically active region. One in vivo test which is used is as follows: the test compounds are tested on normotensive marmosets of both genders and having a body weight of about 350 g which are conscious, able to move freely and in their normal cages. Blood pressure and heart rate are measured using a catheter in the descending aorta and recorded radiometrically. The endogenous release of renin is stimulated by the combination of a 1-week low-salt diet with a single intramuscular injection of furosemide (5-(aminosulphonyl)-4-chloro-2-[2-furanylmethyl)amino]benzoic acid) (5 mg/kg). 16 hours after the injection of furosemide, the test substances are administered either directly into the femoral artery by means of an injection cannula or into the stomach by gavage as a suspension or solution, and their effect on blood pressure and heart rate is evaluated. The compounds of the present invention effectively reduce blood pressure in the in vivo test described at doses of about 0.003 to about 0.3 mg/kg i.v. and at doses of about 0.3 to about 30 mg/kg p.o.

The compounds of the present invention may find use for the treatment of hypertension, congestive heart failure, cardiac hypertrophy, cardiac fibrosis, cardiomyopathy postinfarction, complications resulting from diabetes, such as nephropathy, vasculopathy and neuropathy, disorders of the cardiac vessel, restenosis after angioplasty, increased intraocular pressure, glaucoma, abnormal vascular growth, hyperaldosteronism, states of anxiety and cognitive disorders.

The compound groups mentioned below are not to be regarded as closed, but rather parts of these compound groups may be exchanged with one another or with the definitions given above or omitted in a sensible manner, for example to replace general by more specific definitions.

Preference is given to compounds of the formula (I) in which X is methylene.

Preference is given to compounds of the formula (I) in which $R^1$ is hydrogen or $C_1$-$C_8$-alkyl.

When $R^2$ is aryl-$C_0$-$C_4$-alkyl, it is preferably aryl-$C_0$-$C_1$-alkyl.

Preference is given to compounds of the formula (I), in which $R^2$ is $C_1$-$C_8$-alkyl, $C_3$-$C_8$-cycloalkyl, $C_1$-$C_8$-alkylsulphonyl, $C_3$-$C_8$-cycloalkylsulphonyl, aryl-$C_0$-$C_8$-alkylsulphonyl, $C_3$-$C_{12}$cycloalkyl-$C_1$-$C_8$-alkanoyl, $C_3$-$C_{12}$-cycloalkyl-$C_3$-$C_8$-cycloalkanoyl, aryl-$C_1$-$C_8$-alkanoyl, heterocyclyl-$C_1$-$C_8$-alkanoyl, $C_1$-$C_8$-alkanoyl or aryl-$C_0$-$C_4$-alkyl, which radicals may be substituted by 1-4 $C_1$-$C_8$-alkyl, $C_3$-$C_8$-cycloalkyl, $C_3$-$C_8$-cycloalkoxy, $C_0$-$C_6$-alkylcarbonylamino, halogen, cyano, hydroxyl, oxide, trifluoromethyl, $C_1$-$C_8$-alkoxy or optionally N-mono-or N,N-di-$C_1$-$C_8$-alkylated carbamoyl.

Particular preference is given to compounds of the formula (I) in which $R^2$ is $C_3$-$C_8$-cycloalkyl, $C_1$-$C_8$-alkylsulphonyl, $C_3$-$C_8$-cycloalkylsulphonyl, aryl-$C_0$-$C_8$-alkylsulphonyl, $C_3$-$C_{12}$-cycloalkyl-$C_1$-$C_8$-alkanoyl, $C_3$-$C_{12}$-cycloalkyl-$C_3$-$C_8$-cycloalkanoyl, aryl-$C_1$-$C_8$-alkanoyl, heterocyclyl-$C_1$-$C_8$-alkanoyl or $C_1$-$C_8$-alkanoyl, which radicals may be substituted by 1-4 $C_1$-$C_8$-alkyl, $C_3$-$C_8$-cycloalkyl, $C_3$-$C_8$-cycloalkoxy, $C_0$-$C_6$-alkylcarbonylamino, halogen, cyano, hydroxyl, oxide, trifluoromethyl, $C_1$-$C_8$-alkoxy or optionally N-mono- or N,N-di-$C_1$-$C_8$-alkylated carbamoyl.

Very particular preference is given to compounds of the formula (I) in which $R^2$ is $C_1$-$C_8$-alkylsulphonyl, $C_3$-$C_8$-cycloalkylsulphonyl, aryl-$C_0$-$C_8$-alkylsulphonyl, $C_3$-$C_{12}$-cycloalkyl-$C_1$-$C_8$-alkanoyl, $C_3$-$C_{12}$-cycloalkyl-$C_3$-$C_8$-cycloalkanoyl, aryl-$C_1$-$C_8$-alkanoyl, heterocyclyl-$C_1$-$C_8$-alkanoyl or $C_1$-$C_8$-alkanoyl, which radicals may be substituted by 1-4 $C_1$-$C_8$-alkyl, $C_3$-$C_8$-cycloalkyl, $C_3$-$C_8$-cycloalkoxy, $C_0$-$C_6$-alkylcarbonylamino, halogen, cyano, hydroxyl, oxide, trifluoromethyl, $C_1$-$C_8$-alkoxy or optionally N-mono- or N,N-di-$C_1$-$C_8$-alkylated carbamoyl.

Preference is further given to compounds of the formula (I) in which $R^2$ together with $R^1$ and the nitrogen atom to which they are bonded, is a saturated or partly unsaturated, 4-8-membered heterocyclic ring which may contain an additional nitrogen or oxygen atom, in which case the additional nitrogen atom may optionally be substituted by $C_1$-$C_8$-alkyl or $C_1$-$C_8$-alkanoyl, in which case this heterocyclic ring may be part of a bicyclic or tricyclic ring system having a total of up to 16 ring members and the second ring may also contain a nitrogen or oxygen atom, and the nitrogen atom of the second ring may optionally be substituted by $C_1$-$C_8$-alkyl or $C_1$-$C_8$-alkanoyl, and all ring systems mentioned may be substituted by 1-4 $C_1$-$C_8$-alkyl, hydroxyl, oxide, oxo, $C_1$-$C_8$-alkoxy, $C_1$-$C_8$-alkoxy-$C_1$-$C_8$-alkoxy, $C_1$-$C_8$-alkanoylamino or aryloxy-$C_0$-$C_4$-alkyl-$C_1$-$C_8$-alkoxy.

Preference is further given to compounds of the formula (I) in which, when X is methylene, $R^1$ a) is hydrogen; or
  b) is $C_1$-$C_8$-alkyl or $C_3$-$C_8$-cycloalkyl;

$R^2$ a) is $C_1$-$C_8$-alkyl, $C_3$-$C_8$-cycloalkyl, $C_1$-$C_8$-alkanoyl, heterocyclyl-$C_1$-$C_8$-alkanoyl, $C_3$-$C_{12}$-cycloalkyl-$C_1$-$C_8$-alkanoyl or aryl-$C_1$-$C_8$-alkanoyl, which radicals may be substituted by 1-4 $C_1$-$C_8$-alkyl, $C_{1-6}$-alkylamino, cyano, halogen, hydroxyl, $C_1$-$C_6$-alkanoylamino, $C_1$-$C_8$-alkoxy, oxide, oxo, trifluoromethyl or aryl; or
  b) together with $R^1$ and the nitrogen atom to which they are bonded, is a saturated or partly unsaturated, 4-8-membered heterocyclic ring which may contain an additional nitrogen or oxygen atom, in which case the additional nitrogen atom may optionally be substituted by $C_1$-$C_8$-alkyl or $C_1$-$C_8$-alkanoyl, in which case this heterocyclic ring may be part of a bicyclic or tricyclic ring system having a total of up to 16 ring members and the second ring may also contain a nitrogen or oxygen atom, and the nitrogen atom of the second ring may optionally be substituted by $C_1$-$C_8$-alkyl or $C_1$-$C_8$-alkanoyl, and all ring systems mentioned may be substituted by 1-4 $C_1$-$C_8$-alkyl, hydroxyl, oxide, oxo, $C_1$-$C_8$-alkoxy, $C_1$-$C_8$-alkoxy-$C_1$-$C_8$-alkoxy, $C_1$-$C_8$-alkanoylamino or aryloxy-$C_0$-$C_4$-alkyl-$C_1$-$C_8$-alkoxy.

The invention further preferably relates to compounds of the formula (I) in which X is methylene;

$R^1$ a) is hydrogen; or
  b) is $C_1$-$C_8$-alkyl or $C_3$-$C_8$-cycloalkyl;

$R^2$ a) is $C_1$-$C_8$-alkyl, $C_3$-$C_8$-cycloalkyl, $C_1$-$C_8$-alkanoyl, heterocyclyl-$C_1$-$C_8$-alkanoyl, $C_3$-$C_{12}$-cycloalkyl-$C_1$-$C_8$-alkanoyl or aryl-$C_1$-$C_8$-alkanoyl, which radicals may be substituted by 1-4 $C_1$-$C_8$-alkyl, $C_{1-6}$-alkylamino, cyano, halogen, hydroxyl, $C_1$-$C_8$-alkanoylamino, $C_1$-$C_8$-alkoxy, oxide, oxo, trifluoromethyl or aryl; or
  b) together with $R^1$ and the nitrogen atom to which they are bonded, is a saturated or partly unsaturated, 4-8-membered heterocyclic ring which may contain an additional nitrogen or oxygen atom, in which case the additional nitrogen atom may optionally be substituted by $C_1$-$C_8$-alkyl or $C_1$-$C_8$-alkanoyl, in which case this heterocyclic ring may be part of a bicyclic or tricyclic ring system having a total of up to 16 ring members and the second ring may also contain a nitrogen or oxygen atom, and the nitrogen atom of the second ring may optionally be substituted by $C_1$-$C_8$-alkyl or $C_1$-$C_8$-alkanoyl, and all ring systems mentioned may be substituted by 1-4 $C_1$-$C_8$-alkyl, hydroxyl, oxide, oxo, $C_1$-$C_8$-alkoxy, $C_1$-$C_8$-alkoxy-$C_1$-$C_8$-alkoxy, $C_1$-$C_8$-alkanoylamino or aryloxy-$C_0$-$C_4$-alkyl-$C_1$-$C_8$-alkoxy;

$R^3$ is hydrogen;
$R^4$ is hydrogen;
$R^5$ are each independently hydrogen or $C_1$-$C_8$-alkyl; and
$R^6$ is as defined in the above-specified groups (A) and (B)

and pharmaceutical usable salts thereof.

Particular preference is further given to compounds of the formula (I) in which one $R^5$ radical is hydrogen and one $R^5$ radical is $C_1$-$C_8$-alkyl.

Especially preferred $R^6$ radicals are furyl, thienyl, pyridyl, pyrimidyl, indolyl, quinolinyl, benzoimidazolyl, di-$C_{1-6}$-alkoxypyrimidinyl, 2- and 5-[b]thienyl, 6- and 7-isoquinolyl, 6- and 7-tetrahydroquinolyl, 6- and 7-tetrahydroisoquinolyl, 6-quinoxalinyl, 6- and 7-quinazolinyl,dihydro-3H-benzo[1,4]oxazinyl, 3,4-dihydro-2H-benzo[1,4]oxazinyl, 3-oxo-4H-benzo [1,4]oxazinyl, 2-oxobenzooxazolyl, 2-oxo-1,3-dihydroindolyl, 2,3-dihydroindolyl,indazolyl or benzofuranyl;

and 6- and 7-quinolyl, 6- and 7-isoquinolyl, 6- and 7-tetrahydroquinolyl,oxotetrahydroquinolyl, 6- and 7-tetrahydroisoquinolyl, 6-quinoxalinyl, 6- and 7-quinazolinyl,indolyl, dihydro-3H-benzo[1,4]oxazinyl, 3,4-dihydro-2H-benzo[1,4]oxazinyl, 3-oxo-3,4-dihydro-2H-benzo[1,4]oxazinyl, 3-oxo-4H-benzo[1,4]oxazinyl, 2-oxobenzooxazolyl, 2-oxo-2,3-dihydrobenzooxazolyl, 2-oxo-1,3-dihydroindolyl, 2,3-dihydroindolyl, indazolyl, benzofuranyl, 2,3-dihydrobenzothiazinyl, imidazolyl, benzimidazolyl, pyridinyl, pyrrolo[2,3-b]pyridinyl, pyrrolo[3,2-c]pyridinyl, pyrrolo[2,3-]pyridinyl, pyrrolo[3,2-b]pyridinyl, [1,2,3]triazolo[1,5-a]pyridinyl, [1,2,4]triazolo[4,3-a]pyridinyl, imidazo[1,2-a]pyrimidinyl, imidazo[1,5-a]pyridinyl, naphthyl or cyclohexenophenyl, each of which is substituted by from one to four radicals selected from $C_{1-6}$-alkyl, cyano, oxo, oxide, trifluoromethyl, hydroxyl, halogen, carbamoyl, carboxy, $C_{1-6}$-alkoxy, hydroxy-$C_{2-7}$-alkoxy, $C_{1-6}$-alkoxy-$C_{1-6}$-alkoxy, di-$C_{1-6}$-alkylamino, 2,3-dihydroxypropoxy, 2,3-dihydroxypropoxy-$C_{1-6}$-alkoxy, 2,3-dimethoxypropoxy, methoxybenzyloxy, hydroxybenzyloxy, phenethyloxy, methylenedioxybenzyloxy, dioxolanyl-$C_{1-6}$-alkoxy, cyclopropyl-$C_{1-6}$-alkoxy, pyridylcarbamoyloxy-$C_{1-6}$-alkoxy, 3-morpholino-2-hydroxypropoxy, benzyloxy-$C_{1-6}$-alkoxy, picolyloxy, $C_{1-6}$-alkoxycarbonyl, $C_{1-6}$-alkoxy-$C_{1-6}$-alkoxy-$C_{1-6}$-alkyl, $C_{1-6}$-alkylcarbonylamino, $C_{1-6}$-alkylcarbonylamino-$C_{1-6}$-alkyl, $C_{1-6}$-alkylcarbonylamino-$C_{1-6}$-alkoxy, (N—$C_{1-6}$-alkyl)-$C_{1-6}$-alkylcarbonylamino-$C_{1-6}$-alkyl, (N—$C_{1-6}$-alkyl)-$C_{1-6}$-alkylcarbonylamino-$C_{1-6}$-alkoxy, $C_{3-6}$-cycloalkylcarbonylamino-$C_{1-6}$-alkyl, $C_{3-6}$-cycloalkylcarbonylamino-$C_{1-6}$-alkoxy, $C_{1-6}$-alkoxy-$C_{1-6}$-alkyl, hydroxy-$C_{1-6}$-alkyl, hydroxy-$C_{2-7}$-alkoxy-$C_{1-6}$-alkyl, hydroxy-$C_{2-7}$-alkoxy-$C_{1-6}$-alkoxy, $C_{1-6}$-alkoxycarbonylamino-$C_{1-6}$-alkyl, $C_{1-6}$-alkoxycarbonylamino-$C_{2-7}$-alkoxy, $C_{1-6}$-alkylaminocarbonylamino-$C_{1-6}$-alkyl, $C_{1-6}$-alkylaminocarbonylamino-$C_{2-7}$-alkoxy, $C_{1-6}$-alkylaminocarbonyl-$C_{1-6}$-alkyl, $C_{1-6}$-alkylaminocarbonyl-$C_{1-6}$-alkoxy, $C_{1-6}$-alkylaminocarbonyl-$C_{1-6}$-alkoxy-$C_{1-6}$-alkyl, di-$C_{1-6}$-alkylaminocarbonyl-$C_{1-6}$-alkyl, di-$C_{1-6}$-alkylaminocarbonyl-$C_{1-6}$-alkoxy, $C_{1-6}$-alkylcarbonyloxy-$C_{1-6}$-alkyl, $C_{1-6}$-alkylcarbonyloxy-$C_{1-6}$-alkoxy, cyano-$C_{1-6}$-alkyl, cyano-$C_{1-6}$-alkoxy, 2-oxooxazolidinyl-$C_{1-6}$-alkyl, 2-oxooxazolidinyl-$C_{1-6}$-alkoxy, $C_{1-6}$-alkoxycarbonyl-$C_{1-6}$-alkyl, $C_{1-6}$-alkoxycarbonyl-$C_{1-6}$-alkoxy, $C_{1-6}$-alkylsulphonylamino-$C_{1-6}$-alkyl, $C_{1-6}$-alkylsulphonylamino-$C_{2-7}$-alkoxy, (N—$C_{1-6}$-alkyl)-$C_{1-6}$-alkylsulphonylamino-$C_{1-6}$-alkyl, (N—$C_{1-6}$-alkyl)-$C_{1-6}$-alkylsulphonylamino-$C_{1-6}$-alkoxy, $C_{1-6}$-alkylamino-$C_{1-6}$-alkyl, $C_{1-6}$-alkylamino-$C_{2-7}$-alkoxy, di-$C_{1-6}$-alkylamino-$C_{1-6}$-alkyl, Di-$C_{1-6}$-alkylamino-$C_{2-7}$-alkoxy, $C_{1-6}$-alkylsulphonyl-$C_{1-6}$-alkyl, $C_{1-6}$-alkylsulphonyl-$C_{1-6}$-alkoxy, carboxy-$C_{1-6}$-alkyl, carboxy-$C_{1-6}$-alkoxy, carboxy-$C_{1-6}$-alkoxy-$C_{1-6}$-alkyl, $C_{1-6}$-alkoxy-$C_{1-6}$-alkylcarbonyl, acyl-$C_{1-6}$-alkoxy-$C_{1-6}$-alkyl, (N—$C_{1-6}$-alkyl)-$C_{1-6}$-alkoxycarbonylamino, (N-hydroxy)-$C_{1-6}$-alkylaminocarbonyl-$C_{1-6}$-alkyl, (N-hydroxy)-$C_{1-6}$-alkylaminocarbonyl-$C_{1-6}$-alkoxy, (N-hydroxy)aminocarbonyl-$C_{1-6}$-alkyl, (N-hydroxy)aminocarbonyl-$C_{1-6}$-alkoxy, $C_{1-6}$-alkoxyaminocarbonyl-$C_{1-6}$-alkyl, 6-alkoxy-aminocarbonyl-$C_{1-6}$-alkoxy, (N—$C_{1-6}$-alkoxy)-$C_{1-6}$-alkylaminocarbonyl-$C_{1-6}$-alkyl, (N—$C_{1-6}$-alkoxy)-$C_{1-6}$-alkylaminocarbonyl-$C_{1-6}$-alkoxy, (N-acyl)-$C_{1-6}$-alkoxy-$C_{1-6}$-alkylamino, $C_{1-6}$-alkoxy-$C_{1-6}$-alkylcarbamoyl, (N—$C_{1-6}$-alkyl)-$C_{1-6}$-alkoxy-$C_{1-6}$-alkylcarbamoyl, $C_{1-6}$-alkoxy-$C_{1-6}$-alkylcarbonyl, $C_{1-6}$-alkoxy-$C_{1-6}$-alkylcarbonylamino, (N—$C_{1-6}$-alkyl)-$C_{1-6}$-alkoxy-$C_{1-6}$-alkylcarbonylamino, 1-$C_{1-6}$-alkoxy-$C_{1-6}$-alkylimidazol-2-yl, 1-$C_{1-6}$-alkoxy-$C_{1-6}$-alkyltetrazol-5-yl, 5-$C_{1-6}$-alkoxy-$C_{1-6}$-alkyltetrazol-1-yl, 2-$C_{1-6}$-alkoxy-$C_{1-6}$-alkyl-4-oxoimidazol-1-yl, carbamoyl-$C_{1-6}$-alkyl, carbamoyl-$C_{1-6}$-alkoxy, $C_{1-6}$-alkylcarbamoyl, di-$C_{1-6}$-alkylcarbamoyl, $C_{1-6}$-alkylsulphonyl, piperidinoalkyl, piperidinoalkoxy, piperidinoalkoxyalkyl, morpholinoalkyl, morpholinoalkoxy, morpholinoalkoxyalkyl, piperazinoalkyl, piperazinoalkoxy, piperazinoalkoxyalkyl, [1,2,4]-triazol-1-ylalkyl, [1,2,4]-triazol-1-ylalkoxy, [1,2,4]-triazol-4-ylalkyl, [1,2,4]-triazol-4-ylalkoxy, [1,2,4]-oxadiazol-5-ylalkyl, [1,2,4]-oxadiazol-5-ylalkoxy, 3-methyl-[1,2,4]-oxadiazol-5-ylalkyl,3-methyl-[1,2,4]-oxadiazol-5-ylalkoxy, 5-methyl-[1,2,4]-oxadiazol-3-ylalkyl, 5-methyl-[1,2,4]-oxadiazol -3-ylalkoxy, tetrazol-1-ylalkyl, tetrazol-1-ylalkoxy, tetrazol-2-ylalkyl, tetrazol-2-ylalkoxy, tetrazol-5-ylalkyl, tetrazol-5-ylalkoxy, 5-methyl-tetrazol-1-ylalkyl, 5-methyl-tetrazol -1-ylalkoxy, thiazol-4-ylalkyl, thiazol-4-ylalkoxy, oxazol-4-ylalkyl, oxazol-4-ylalkoxy, 2-oxo-pyrrolidinylalkyl, 2-oxo-pyrrolidinylalkoxy, imidazolylalkyl, imidazolylalkoxy, 2-methyl-imidazolylalkyl, 2-methyl-imidazolylalkoxy, N-methylpiperazinoalkyl, N-methylpiperazinoalkoxy, N-methylpiperazinoalkoxyalkyl, pyrrolidinyl, piperidinyl, piperazinyl, pyrrolyl, 4-methylpiperazinyl, morpholinyl, thiomorpholinyl, 2-hydroxymethylpyrrolidinyl, 3-hydroxypyrrolidinyl, 3,4-dihydroxypyrrolidinyl, 3-acetamidomethylpyrrolidinyl, 3-$C_{1-6}$-alkoxy-$C_{1-6}$-alkyl-pyrrolidinyl, 4-hydroxypiperidinyl, 4-oxopiperidinyl, 3,5-dimethylmorpholinyl, 4,4-dioxothiomorpholinyl, 4-oxothiomorpholinyl, 2,6-dimethylmorpholinyl, 2-oxoimidazolidinyl, 2-oxooxazolidinyl, 2-oxopyrrolidinyl, 2-oxo-[1,3]oxazinyl and 2-oxotetrahydropyrimidinyl.

Further especially preferred $R^6$ radicals are heterocyclyl radicals, preferably indolyl, 3,4-dihydro-2H-benzo[1,4]oxazinyl, indazolyl, benzofuranyl, benzoimidazolyl, pyridinyl, pyrrolo[2,3-b]pyridinyl, pyrrolo[3,2-c]pyridinyl, pyrrolo[2,3-c]pyridinyl, pyrrolo[3,2-b]pyridinyl, [1,2,3]triazolo[1,5-a]pyridinyl, [1,2,4]triazolo[4,3-a]pyridinyl, imidazo[1,2-a]pyrimidinyl or imidazo[1,5-a]pyridinyl, or naphthyl, each of which is substituted by from one to four radicals selected from $C_{1-6}$-alkyl, cyano, oxo, oxide, trifluoromethyl, hydroxyl, halogen, carbamoyl, carboxy, $C_{1-6}$-alkoxy, hydroxy-$C_{2-7}$-alkoxy, $C_{1-6}$-alkoxy-$C_{1-6}$-alkoxy, $C_{1-6}$-alkoxy-$C_{1-6}$-alkyl or $C_{1-6}$-alkoxy-$C_{1-6}$-alkoxy-$C_{1-6}$-alkyl.

Particular preference is given in each case to those compounds of the formula (I) in which at least one asymmetric carbon atom, for example one, two or preferably all three asymmetric carbon atoms, of the main chain have the stereochemistry (in each case "S") shown in the formula (Ia)

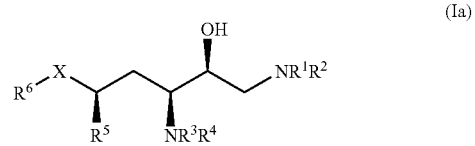

(Ia)

where one $R^5$ substituent is hydrogen and the remaining substituents are each as defined above including the preferences specified, and pharmaceutically usable salts thereof.

The compounds of the formula (I) may also be prepared in optically pure form. The separation into antipodes may be effected by methods known per se, either preferably at a synthetically early stage by salt formation with an optically active acid, for example (+)- or (−)-mandelic acid and separation of the diastereomeric salts by fractional crystallization, or preferably at a rather later stage by derivatization with a chiral auxiliary building block, for example (+)- or (−)-camphanoyl chloride, and separation of the diastereomeric products by chromatography and/or crystallization and subsequent cleavage of the bond to the chiral auxiliary. To determine the absolute configuration of the piperidine present, the pure diastereomeric salts and derivatives may be analysed with common spectroscopic methods, of which X-ray spectroscopy on single crystals constitutes a particularly suitable method.

Prodrug derivatives of the compounds described in the present context are derivatives thereof which, on in vivo application, release the original compound by a chemical or physiological process. A prodrug may be converted to the original compound, for example, when a physiological pH is attained or by enzymatic conversion. Prodrug derivatives may, for example, be esters of freely available carboxylic acids, S- and O-acyl derivatives of thiols, alcohols or phenols, and the acyl group is as defined in the present context. Preference is given to pharmaceutically usable ester derivatives which are converted by solvolysis in physiological medium to the original carboxylic acid, for example lower alkyl esters, cycloalkyl esters, lower alkenyl esters, benzyl esters, mono- or disubstituted lower alkyl esters such as lower ω-(amino, mono- or dialkylamino, carboxyl, lower alkoxycarbonyl)-alkyl esters or such as lower α-(alkanoyloxy, alkoxycarbonyl or dialkylaminocarbonyl)-alkyl esters; as such, pivaloyloxymethyl esters and similar esters are utilized in a conventional manner.

Owing to the close relationship between a free compound, a prodrug derivative and a salt compound, a certain compound in this invention also encompasses its prodrug derivative and salt form, where this is possible and appropriate.

The compounds of the formula (I) or formula (Ia) also include those compounds in which one or more atoms are replaced by their stable, non-radioactive isotopes; for example, a hydrogen atom by deuterium.

The compounds of the formula (I) or formula (Ia), and the pharmaceutically usable salts thereof, may find use as medicines, for example in the form of pharmaceutical preparations. The pharmaceutical preparations may be administered enterally, such as orally, for example in the form of tablets, coated tablets, sugar-coated tablets, hard and soft gelatin capsules, solutions, emulsions or suspensions, nasally, for example in the form of nasal sprays, rectally, for example in the form of suppositories, or transdermally, for example in the form of ointments or patches. The administration may also be parenteral, such as intramuscular or intravenous, for example in the form of injection solutions.

To prepare tablets, coated tablets, sugar-coated tablets and hard gelatin capsules, the compounds of the formula (I) or formula (Ia) and pharmaceutically usable salts thereof may be processed with pharmaceutically inert, inorganic or organic excipients. Such excipients used, for example for tablets, coated tablets and hard gelatin capsules, may be lactose, corn starch, or derivatives thereof, talc, stearic acid or salts thereof etc.

Suitable excipients for soft gelatin capsules are, for example, vegetable oils, waxes, fats, semisolid and liquid polyols, etc.

Suitable excipients for preparing solutions and syrups are, for example, water, polyols, sucrose, invert sugar, glucose, etc.

Suitable excipients for injection solutions are, for example, water, alcohols, polyols, glycerol, vegetable oils, bile acids, lecithin, etc.

Suitable excipients for suppositories are, for example, natural or hardened oils, waxes, fats, semisolid or liquid polyols, etc.

The pharmaceutical preparations may additionally also comprise preservatives, solubilizers, viscosity-increasing substances, stabilizers, wetting agents, emulsifiers, sweeteners, colorants, flavourings, salts for altering the osmotic pressure, buffers, coatings or antioxidants. They may also comprise other therapeutically valuable substances.

The present invention further provides the use of the compounds of the formula (I) or formula (Ia), and the pharmaceutically usable salts thereof, in the treatment or prevention of hypertension and heart failure, and also glaucoma, myocardial infarction, kidney failure and restenoses.

The compounds of the formula (I) or formula (Ia) and the pharmaceutically usable salts thereof may also be administered in combination with one or more agents having cardiovascular action, for example α- and β-blockers such as phentolamine, phenoxybenzamine, prazosin, terazosin, tolazine, atenolol, metoprolol, nadolol, propranolol, timolol, carteolol etc.; vasodilators such as hydralazine, minoxidil, diazoxide, nitroprusside, flosequinan etc.; calcium antagonists such as amrinone, bencyclan, diltiazem, fendiline, flunarizine, nicardipine, nimodipine, perhexilene, verapamil, gallopamil, nifedipine etc.; ACE inhibitors such as cilazapril, captopril, enalapril, lisinopril etc.; potassium activators such as pinacidil; anti-serotoninergics such as ketanserin; thromboxane-synthetase inhibitors; neutral endopeptidase inhibitors (NEP inhibitors); angiotensin II antagonists; and also diuretics such as hydrochlorothiazide, chlorothiazide, acetazolamide, amiloride, bumetanide, benzthiazide, ethacrynic acid, furosemide, indacrinone, metolazone, spironolactone, triamteren, chlorthalidone etc.; sympatholytics such as methyldopa, clonidine, guanabenz, reserpine; and other agents which are suitable for the treatment of hypertension, heart failure or vascular diseases in humans and animals which are associated with diabetes or renal disorders such as acute or chronic renal failure. Such combinations may be employed separately or in preparations which comprise a plurality of components.

Further substances which can be used in combination with the compounds of the formula (I) are the compounds of classes (i) to (ix) on page 1 of WO 02/40007 (and also the preferences and examples further listed therein) and the substances specified on pages 20 and 21 of WO 03/027091.

The dose may vary within wide limits and has of course to be adapted to the individual circumstances in each individual case. In general, for oral administration, a daily dose of about 3 mg to about 3 g, preferably about 10 mg to about 1 g, for example about 300 mg, per adult (70 kg), divided into preferably 1-3 individual doses which may, for example, be of equal size, may be appropriate, although the upper limit specified may also be exceeded if this should be found to be appropriate; typically, children receive a lower dose according to their age and body weight.

The compounds of the formula (I) or formula (Ia) may be prepared in an analogous manner to preparative processes known from the literature. The starting materials to carry out the preparative processes are described, for example, in EP 0678503 and in Helvetica Chemica Acta 86 (2003), 2848-2870 or literature cited therein. The inventive compounds of the formula I and salts of such compounds having at least one salt-forming group are obtained by processes known per se, for example by a) condensing a compound of the formula II

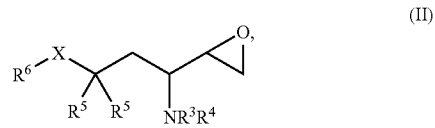

(II)

where X, $R^3$, $R^4$, $R^5$ and $R^6$ are each as defined above or a salt thereof with a compound of the formula $R^1R^2NH$ (III) where $R^1$ and $R^2$ are each as defined above, in the course of which free functional groups in the reaction components with the exception of the groups taking part in the reaction are present in protected form, and detaching protecting groups present. In cases where $R^1$ and $R^2$ are a saturated or partly unsaturated oxo-substituted heterocyclic ring (for example lactams) and strong bases are used as a reagent, the alkoxide formed by epoxide formation may react with one of the protecting groups present (e.g. N-Boc) and form an oxazolidinone which may be cleaved to give the product, for example with lithium hydroxide, or b) condensing a compound of the formula II

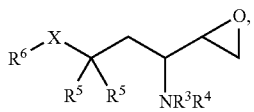
(II)

where X, $R^3$, $R^4$, $R^5$ and $R^6$ are each as defined above or a salt thereof with an azide, reducing the azido group to amino and then, depending on the definitions of $R^1$ and $R^2$, mono- or dialkylating, mono- or diacylating, and also optionally sulphonylating the amino group, in the course of which free functional groups present in the reaction components with the exception of the groups taking part in the reaction are present in protected form, and detaching protecting groups present, or c) condensing a compound of the formula IV

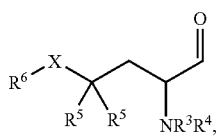
(IV)

where X, $R^3$, $R^4$, $R^5$ and $R^6$ are each as defined above or a salt thereof with cyanide or nitromethane, reducing the nitrile group or nitro group to amino, and then, depending on the definitions of $R^1$ and $R^2$, mono- or dialkylating, mono- or diacylating, and also optionally sulphonylating the amino group, in the course of which free functional groups present in the reaction components with the exception of the groups taking part in the reaction are present in protected form, and detaching protecting groups present.

Compounds of the formula 11 can be prepared in an analogous manner to preparative processes known from the literature, for example by a) condensing a compound of the formula IV

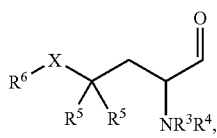
(IV)

where X, $R^3$, $R^4$, $R^5$ and $R^6$ are each as defined above or a salt thereof with methylide (see, for example, in Tet. Lett. 30(40), 5425-5428, 1989), in the course of which free functional groups present in the reaction components with the exception of the groups taking part in the reaction are present in protected form, and detaching protecting groups present, or b) epoxidizing a compound of the formula V

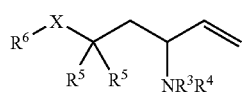
(V)

where X, $R^3$, $R^4$, $R^5$ and $R^6$ are each as defined above or a salt thereof (see, for example, in J. Med. Chem. 35(10), 1685-1701, 1992 and J. Org. Chem. 59(3), 653-657, 1994), in the course of which free functional groups present in the reaction components with the exception of the groups taking part in the reaction are present in protected form, and protecting groups present are detached, or c) dihydroxylating a compound of the formula V

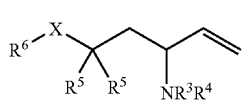
(V)

where X, $R^3$, $R^4$, $R^5$ and $R^6$ are each as defined above or a salt thereof, tosylating the primary alcohol and subsequently admixing with a base such as potassium hydroxide (see, for example in WO 03050073), in the course of which free functional groups present in the reaction components with the exception of the groups taking part in the reaction are present in protected form, and detaching protecting groups present, or d) preparing an activated ester from a compound of the formula VI

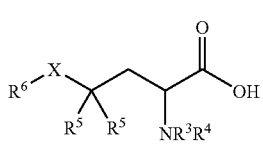
(VI)

where X, $R^3$, $R^4$, $R^5$ and $R^6$ are each as defined above or a salt thereof and admixing it with diazomethane, admixing the diazoketone with 48% HBr, and then reducing the bromoketone and subsequently admixing it with a base such as potassium hydroxide (see, for example, in WO 03050073), in the course of which free functional groups present in the reaction components with the exception of the groups taking part in the reaction are present in protected form, and detaching protecting groups present.

Details of the specific preparation variants can be taken from the examples.

The examples which follow illustrate the present invention. All temperatures are reported in degrees Celsius, pressures in mbar. Unless stated otherwise, the reactions take place at room temperature. The abbreviation "Rf=xx (A)" means, for example, that the Rf value xx is determined in the solvent system A. The ratio of solvents relative to one another is always reported in parts by volume. Chemical names for end products and intermediates were generated with the aid of the program AutoNom 2000 (automatic nomenclature). Unless stated otherwise, the absolute stereochemistry of all three asymmetric carbon atoms of the main chain of the formula (Ia) is in each case "S".

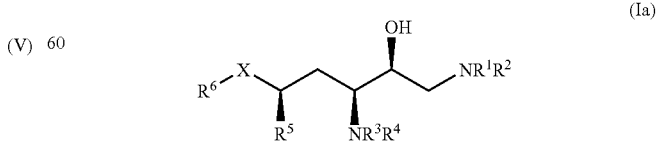
(Ia)

HPLC gradients on Hypersil BDS C-18 (5 um); column: 4×125 mm

I 90% water*/10% acetonitrile* to 0% water*/100% acetonitrile* in 5 minutes+2.5 minutes (1.5 m/min)

II 95% water*/5% acetonitrile* to 0% water*/100% acetonitrile* in 40 minutes (0.8 ml/min)

* contains 0.1% trifluoroacetic acid

The following abbreviations are used:

Rf ratio of distance travelled by a substance to separation of the eluent front from the start point in thin-layer chromatography Rt ion time of a substance in HPLC (in minutes)

m.p. melting point (temperature)

General Method A: (N-BOC Deprotection)

A solution of 0.2 mmol of "N-BOC derivative" in 2 ml of 4N HCl/dioxane is stirred at 0° C. over 2-6 hours. The reaction mixture is admixed with dioxane, frozen in liquid nitrogen and lyophilized under high vacuum overnight. The title compound is obtained from the residue.

General Method B: (N-Cbz Deprotection)

The solution of 1 mmol of "N-Cbz derivative" in 15 ml of tetrahydrofuran is hydrogenated in the presence of 100-200 mg of 10% Pd/C at 15-20° C. over 2-20 hours. The reaction mixture is clarified by filtration and the filtrate is concentrated by evaporation. The title compound is obtained from the residue by means of flash chromatography (SiO$_2$ 60F).

General Method C: (Phenol Alkylation I)

The mixture of 20 mmol of "phenol" in 60 ml of N,N-dimethylformamide is stirred with 4.15 g of potassium carbonate and 30 mmol of "halide" or "tosylate" at 100° C. over 24 hours. The reaction mixture is then concentrated by evaporation. The residue is admixed with 1M aqueous sodium hydrogencarbonate solution (40 ml) and extracted with ethyl acetate (2×60 ml). The organic phases are washed with brine (1×60 ml), dried over sodium sulphate and concentrated by evaporation. The title compound is obtained from the residue by means of flash chromatography (SiO$_2$ 60F).

Residues $R^6$:

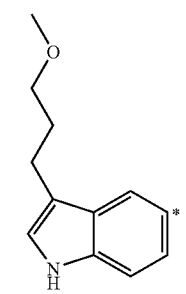

1

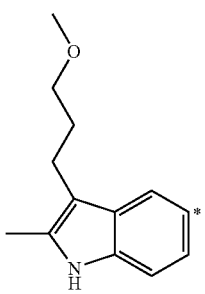

2

-continued

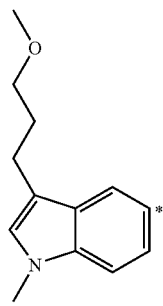

3

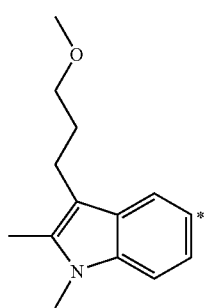

4

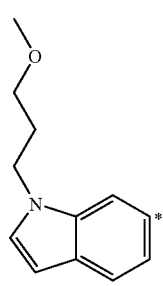

5

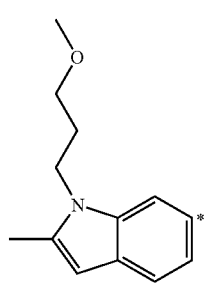

6

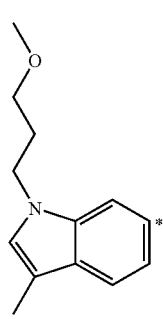

7

8
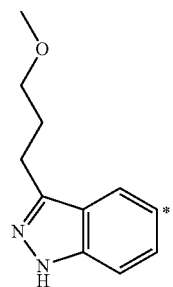
9
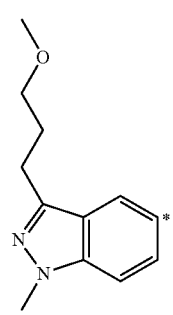
10
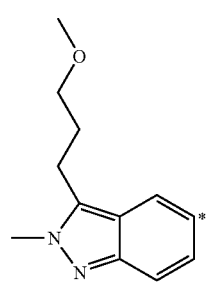
11
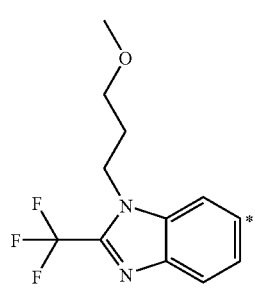
12
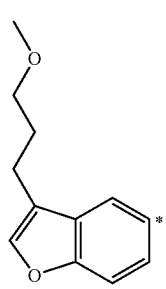
13
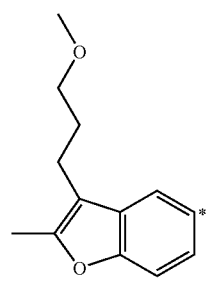
14
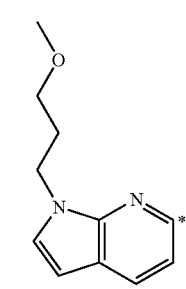
15
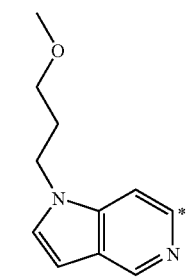
16
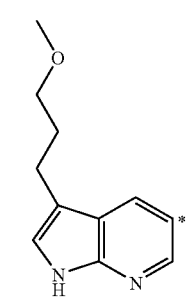
17
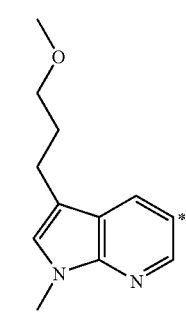

-continued
18
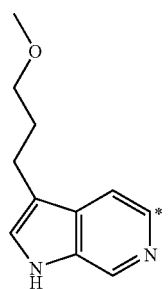
19
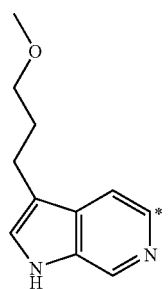
20
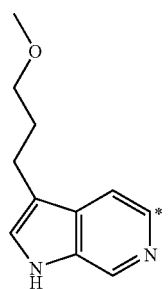
21
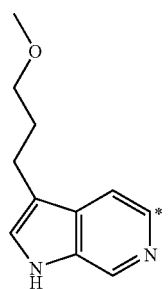
22
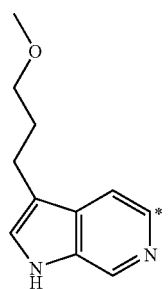
-continued
23
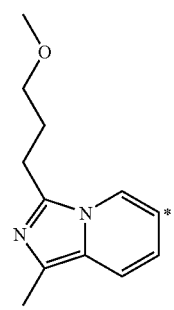
24
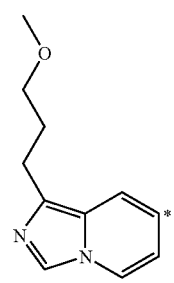
25
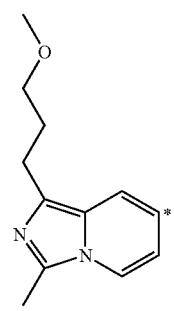
26
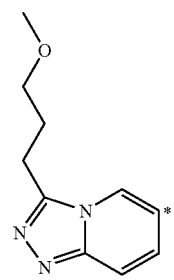
27
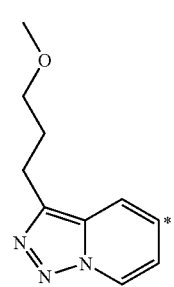

| 28 | 33 |
|---|---|
| 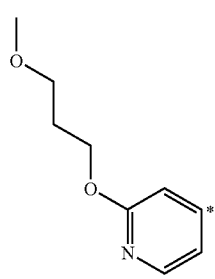 | 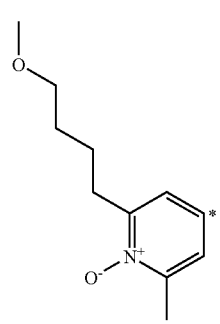 |
| 29 | 34 |
| 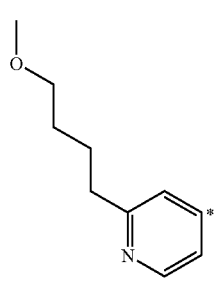 | 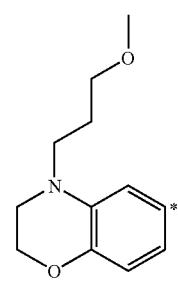 |
| 30 | 35 |
| 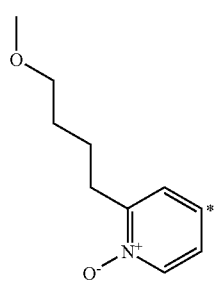 | 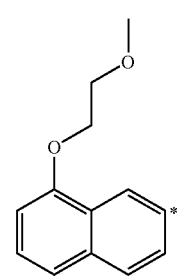 |
| 31 | 36 |
| 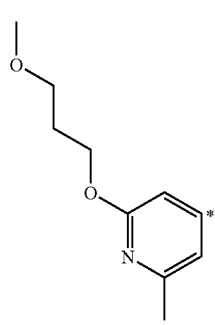 | 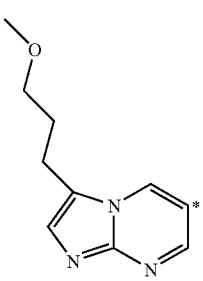 |
| 32 | 37 |
| 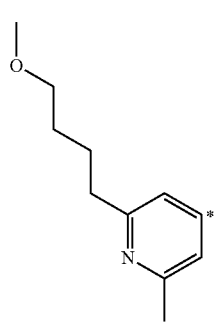 | 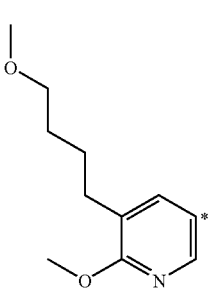 |

-continued

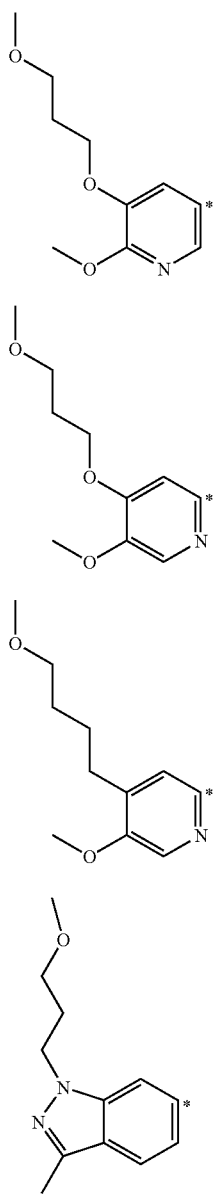

The protected or unprotected residues R⁶ (bromide or iodide derivatives) are prepared as follows:

1 5-Bromo-3-(3-methoxypropyl)-1-(2-trimethylsilanylethoxymethyl)-1H-indole

The stirred solution of 1.0 g of 5-bromo-3-(3-methoxyprop-(E,Z)-enyl)-1-(2-trimethylsilanylethoxymethyl)-1 H-indole in 40 ml of ethyl acetate is admixed at 0° C. with 0.152 ml of acetic acid and 0.402 g of 10% Pd/C. The mixture is hydrogenated at 0° C. over 1 hour and then clarified by filtration, and the filtrate is washed successively with 1M sodium hydrogencarbonate solution (cold) and brine. The organic phase is dried over sodium sulphate and filtered, and the filtrate is concentrated by evaporation. The title compound is obtained as a yellowish oil from the residue by means of flash chromatography (SiO2 60F). Rf=0.25 (1:4 EtOAc-heptane). Rt=6.26 (gradient I).

The starting materials are prepared as follows:

a) 5-Bromo-3-(3-methoxyprop-(E,Z)-enyl)-1-(2-trimethylsilanylethoxymethyl)-1H-indole 95.3 ml of a sodium bis(trimethylsilyl)amide solution (1M in tetrahydrofuran) is added dropwise at 0° C. over 10 minutes to the stirred mixture of 37.9 g of (2-methoxyethyl)triphenylphosphonium bromide [55894-16-1] in tetrahydrofuran. The mixture is stirred at 0° C. over a further 30 minutes and the solution of 22.2 g of 5-bromo-1-(2-trimethylsilanylethoxymethyl)-1H-indole-3-carbaldehyde in 100 ml of tetrahydrofuran is subsequently added dropwise. The reaction mixture is stirred at 0° C. over a further 1 hour, quenched with 1M ammonium chloride solution, diluted with water and extracted with tert-butyl methyl ether (2×). The combined organic phases are washed with water and brine, dried over sodium sulphate and filtered, and the filtrate is concentrated by evaporation. The title compound (E,Z mixture) is obtained as a brown oil from the residue by means of flash chromatography (SiO2 60F). Rf=0.46 (1:2 EtOAc-heptane). Rt=6.20 (gradient I).

b) 5-Bromo-1-(2-trimethylsilanylethoxymethyl)-1-indole-3-carbaldehyde

The stirred solution of 25 g of 5-bromo-1H-indole-3-carbaldehyde [877-03-2] in 250 ml of N,N-dimethylformamide is admixed at 0° C. with 4.59 g of sodium hydride (60% in mineral oil) in portions. The mixture is stirred over 1 hour and then admixed dropwise with 22.5 ml of 2-(trimethylsilyl)ethoxymethyl chloride (SEM-Cl). The mixture is stirred at room temperature over 16 hours. The resultant reaction mixture is poured onto 350 ml of 1M sodium hydrogencarbonate solution (cold) and extracted with tert-butyl methyl ether (2×). The combined organic phases are washed successively with water (3×) and brine, dried over sodium sulphate and filtered, and the filtrate is concentrated by evaporation. The title compound is obtained as a white solid from the residue by means of crystallization (from diisopropyl ether). Rf=0.23 (1:2 EtOAc-heptane). Rt=5.58 (gradient I). m.p. 105-106° C.

5 6-Bromo-1-(3-methoxypropyl)-1H-indole

The stirred solution of 25 g of 6-bromo-1H-indole [52415-29-9] in 250 ml of DMPU is admixed at 0° C. with 11.2 g of sodium hydride (60% in mineral oil) in portions. The mixture is stirred over 1 hour and then admixed with 60.9 g of 1-chloro-3-methoxypropane and 4.71 g of tetrabutylammonium iodide (exothermic reaction). The mixture is stirred at room temperature over a further 1 hour. The resulting reaction mixture is poured onto 2 l of water (cold) and extracted with tert-butyl methyl ether (2×). The combined organic phases are washed successively with water (3×) and brine, dried over sodium sulphate and filtered, and the filtrate is concentrated by evaporation. The title compound is obtained as a slightly yellowish oil from the residue by means of flash chromatography (SiO2 60F). Rf=0.31 (1:2 EtOAc-heptane). Rt=5.10 (gradient I).

9
5-Bromo-3-(3-methoxypropyl)-1-methyl-1H-indazole

A solution of 54.00 g of 5-bromo-3-(3-methoxyprop-1-ynyl)-1-methyl-1H-indazole in 1700 ml of methanol is admixed at room temperature with 20.58 g of 10% Pd/C. The mixture is hydrogenated over 1.5 hours and clarified by filtration, and the filtrate is concentrated by evaporation. The title compound is obtained as a yellowish oil from the residue by means of flash chromatography (SiO2 60F). Rf=0.56 (1:1 EtOAc-heptane). Rt=4.37 (gradient I).

The starting materials are prepared as follows:

a) 5-Bromo-3-(3-methoxyprop-1-ynyl)-1-methyl-1H-indazole

A solution of 81.67 g of 5-bromo-3-iodo-1-methyl-1H-indazole in 750 ml of N,N-dimethylformamide and 335 ml of triethylamine is admixed at room temperature under argon with 25 ml of 3-methoxypropyne, 5.5 g of copper(I) iodide and 10 g of bis(triphenylphosphine)palladium(II) chloride, and subsequently heated to 60° C. After 1 hour, the reaction mixture is cooled to room temperature, diluted with water and extracted with ethyl acetate (4×). The combined organic phases are dried over sodium sulphate and concentrated by evaporation. The title compound is obtained as a yellow solid from the residue by means of flash chromatography (SiO2 60F). Rf=0.67 (2:1 EtOAc-heptane). Rt=4.42 (gradient I).

b) 5-Bromo-3-iodo-1-methyl-1H-indazole

A solution of 184.30 g of 5-bromo-3-iodo-1H-indazole [459133-66-5] n 2500 ml of methanol is admixed at 40° C. with 212 ml of a sodium methoxide solution (5.4M in methanol). 90 ml of methyl iodide are then added and the reaction mixture is heated to 65° C. After 30 minutes, the reaction mixture is cooled to room temperature, concentrated to approx. 1000 ml by evaporation, diluted with water and extracted with ethyl acetate (2×). The combined organic phases are dried over sodium sulphate and concentrated by evaporation. The title compound is obtained as a dark brown solid from the residue by means of flash chromatography (SiO2 60F). Rf=0.68 (dichloromethane). Rt=4.94 (gradient I). As a by-product, the 5-bromo-3-iodo-2-methyl-2H-indazole regioisomer is also isolated as a red-orange solid. Rf=0.52 (dichloromethane). Rt=4.58 (gradient I).

11 6-Bromo-1-(3-methoxypropyl)-2-trifluoromethyl-1H-benzoimidazole 0.2 ml of concentrated aqueous hydrochloric acid is added under an argon atmosphere to a solution of 12.83 g of 4-bromo-$N^2$-(3-methoxypropyl)benzene-1,2-diamine in 5.78 ml of trifluoroacetic acid. The reaction mixture is heated to reflux for 4 hours. 2 ml of trifluoroacetic acid are once again added and the reaction mixture is heated to reflux for a further 2 hours. The reaction mixture is cooled to room temperature and neutralized with saturated aqueous sodium hydrogencarbonate solution. The mixture is extracted with ethyl acetate (3×). The combined organic phases are dried over sodium sulphate and concentrated by evaporation. The title compound is obtained as a yellow oil from the residue by means of flash chromatography (SiO2 60F). Rf=0.60 (1:2 EtOAc-heptane). Rt=4.79 (gradient I).

The starting materials are prepared as follows:

a) 4-Bromo-$N^2$-(3-methoxypropyl)benzene-1,2-diamine 78.57 g of tin(II) chloride are added to a solution of 21.01 g of (5-bromo-2-nitrophenyl)-(3-methoxypropyl)amine in 950 ml of ethanol. The reaction mixture is heated to reflux for 12 hours. The mixture is cooled to room temperature and concentrated by evaporation. The residue is treated with 2M NaOH until a pH of 11 is obtained. The mixture is extracted with tert-butyl methyl ether (3×). The combined organic phases are dried over sodium sulphate and concentrated by evaporation. The title compound is obtained as an orange oil from the residue. Rf=0.31 (1:1 EtOAc-heptane). Rt=3.06 (gradient I).

b) (5-Bromo-2-nitrophenyl)(3-methoxypropyl)amine

A solution of 26.49 g of 2,4-dibromo-1-nitrobenzene [51686-78-3] and 70 ml of 3-methoxypropylamine is stirred at room temperature for 4 hours and subsequently left to stand at 3° C. for 2 days. The reaction mixture is concentrated by evaporation. The title compound is obtained as a yellow oil from the residue by means of flash chromatography (SiO2 60F). Rf=(1:3 EtOAc-heptane). Rt=4.99 (gradient I).

12 5-Bromo-3-(3-methoxypropyl)benzofuran

Analogously to residue 1, 6.01 g of 5-bromo-3-(3-methoxyprop-1-ynyl)benzofuran are reacted. The title compound is obtained as a yellowish oil. Rf=0.55 (1:6 EtOAc-heptane). Rt=22 (gradient I).

The starting material is prepared as follows:

a) 5-Bromo-3-(3-methoxyprop-1-ynyl)benzofuran

Analogously to residue 9a, 9.31 g of 5-bromobenzofuran-3-yl trifluoromethanesulphonate [440083-74-9] and 3.52 ml of 3-methoxypropyne are reacted. The title compound is obtained as a yellowish oil. Rf=0.43 (1:10 EtOAc-heptane). Rt=5.14 (gradient I).

According to the process described for the residues 1, 5, 9, 11 and 12, the following residues are prepared in an analogous manner:
2 5-Bromo-3-(3-methoxypropyl)-2-methyl-1H-indole
3 5-Bromo-3-(3-methoxypropyl)-1-methyl-1H-indole
4 5-Bromo-3-(3-methoxypropyl)-1,2-dimethyl-1H-indole
6 6-Bromo-1-(3-methoxypropyl)-2-methyl-1H-indole
7 6-Bromo-1-(3-methoxypropyl)-3-methyl-1H-indole
8 5-Bromo-3-(3-methoxypropyl)-1H-indazole
10 5-Bromo-3-(3-methoxypropyl)-2-methyl-2H-indazole
13 5-Bromo-3-(3-methoxypropyl)-2-methyl-benzofuran
14 6-Bromo-1-(3-methoxypropyl)-1H-pyrrolo[2,3-b]pyridine
15 6-Bromo-1-(3-methoxypropyl)-1H-pyrrolo[3,2-c]pyridine
16 5-Bromo-3-(3-methoxypropyl)-1H-pyrrolo[2,3-b]pyridine
17 5-Bromo-3-(3-methoxypropyl)-1-methyl-1H-pyrrolo[2,3-b]pyridine
18 5-Bromo-3-(3-methoxypropyl)-1H-pyrrolo[2,3-c]pyridine
19 5-Bromo-3-(3-methoxypropyl)-1-methyl-1H-pyrrolo[2,3-c]pyridine
20 5-Bromo-3-(3-methoxypropyl)-1H-pyrrolo[3,2-b]pyridine
21 5-Bromo-3-(3-methoxypropyl)-1-methyl-1H-pyrrolo[3,2-b]pyridine
27 5-Bromo-3-(3-methoxypropyl)-[1,2,3]triazolo[1,5-a]pyridine 22 6-Bromo-3-(3-methoxypropyl)-imidazo [1,5-a] pyridine A solution of 5.74 g of N-(5-bromopyridin-2-ylmethyl)4-methoxybutyramide in 20 ml of benzene is admixed with 3.37 g of phosphorus oxychloride. The reaction mixture is heated to reflux over 5 hours. The reaction mixture is subsequently cooled to room temperature and concentrated by evaporation, and the residue is admixed with 100 ml of water. The aqueous solution is basified with saturated aqueous sodium hydrogencarbonate solution and extracted with dichloromethane (3×200 ml). The combined organic phases are washed with 200 ml of water, dried over sodium sulphate and concentrated by evaporation. The title compound is identified on the basis of the Rf value by means of flash chromatography (SiO2 60F).

The starting material is prepared as follows:

a) N-(5-Bromopyridin-2-ylmethyl)-4-methoxybutyramide

A solution of 9.35 g of C-(5-bromopyridin-2-yl)methylamine [17399-23-0] in 200 ml of ethyl acetate is admixed with 300 ml of saturated aqueous sodium carbonate solution. The reaction mixture is cooled to 0° C. in an ice bath and subsequently admixed dropwise with a solution of 4-methoxybutanoyl chloride [61882-39-1] in 100 ml of ethyl acetate. The reaction mixture is stirred at 0° C. over 1 hour. The phases are separated and the aqueous phase is extracted with 300 ml of ethyl acetate (2×). The combined organic phases are washed with 300 ml of brine, dried over sodium sulphate and concentrated by evaporation. The title compound is identified on the basis of the Rf value from the residue by means of flash chromatography (SiO2 60F).

23 6-Bromo-3-(3-methoxypropyl)-1-methylimidazo[1,5-a]pyridine

A solution of 1.42 g of 1,1,1-triphenyl-3-(5-bromopyridin-2-yl)-2-aza-1,$\lambda^5$-phosphabuta-1,3-diene in 10 ml of anhydrous chloroform is admixed with a solution of 0.306 g of 4-methoxybutyraldehyde [21071-24-9] in 5 ml of chloroform. The reaction solution is left to stand at room temperature over 48 hours and subsequently concentrated by evaporation. The title compound is identified on the basis of the Rf value from the residue by means of flash chromatography (SiO2 60F).

The starting material is prepared as follows:

a) 1,1,1-Triphenyl-3-(5-bromopyridin-2-yl)-2-aza-1,$\lambda^5$-phosphabuta-1,3-diene 4.18 g of methyltriphenylphosphonium iodide are taken up in 5 ml of anhydrous benzene under argon and 6.3 ml of a methyllithium solution (1.6M in diethyl ether) are added dropwise. The solution is heated to reflux and the resulting suspension is subsequently cooled to 0° C. A solution of 1.83 g of 5-bromopyridine-2-carbonitrile [97483-77-7] in 4 ml of benzene is added and the reaction mixture is stirred at room temperature over 120 hours. Dichloromethane is added and the lithium salts are filtered off through Hyflo. The filtrate is concentrated. The title compound is identified on the basis of the Rf value from the residue by means of flash chromatography (Alox).

24 7-Bromo-1-(3-methoxypropyl)imidazo[1,5-a]pyridine

A mixture of 5.34 g of 7-bromo-1-(3-methoxypropenyl)imidazo[1,5-a]pyridine and 0.200 g of 10% Pd/C is hydrogenated at 0° C. and standard pressure in 100 ml of 1:1 ethanol/dioxane. As soon as the double bond has been fully reduced, the catalyst is filtered off through Hyflo and the filtercake is washed with methanol (2×20 ml) and the filter is concentrated by evaporation. The title compound is identified on the basis of the Rf value from the residue by means of flash chromatography (SiO2 60F).

The starting material is prepared as follows:

a) 7-Bromo-1-(3-methoxypropenyl)imidazo[1,5-a]pyridine

A suspension of 12.04 g of (2-methoxyethyl)triphenylphosphonium bromide [55894-16-1] in 50 ml of anhydrous N,N-dimethylformamide is admixed with 2.60 g of sodium hydride (60% dispersion). The reaction mixture is stirred at room temperature for 30 minutes and a solution of 6.75 g of 7-bromoimidazo[1,5-a]pyridine-1-carbaldehyde in 20 ml of N,N-dimethylformamide is added. The reaction mixture is subsequently stirred at 50° C. for 1 hour. The reaction mixture is cooled to room temperature and poured onto ice-water. The quenched mixture is acidified with 1M HCl and extracted with tert-butyl methyl ether (3×100 ml). The combined organic phases are washed with water (100 ml) and brine (100 ml), dried over sodium sulphate and concentrated by evaporation. The title compound is identified on the basis of the Rf value from the residue by means of flash chromatography (SiO2 60F).

b) 7-Bromoimidazo[1,5-a]pyridine-1-carbaldehyde

A solution of 4.93 g of 7-bromoimidazo[1,5-a]pyridine in 2.2 ml of dry N,N-dimethylformamide is cooled in an ice bath to 0-5° C. Phosphorus oxychloride (5.37 g) is added dropwise at 0-5° C. and the reaction mixture is subsequently stirred at 100° C. over 1 hour. The reaction mixture is cooled and poured onto ice-water. The quenched solution is basified with 25% ammonium hydroxide solution and extracted with dichloromethane (3×200 ml). The combined organic phases are dried over sodium sulphate and concentrated by evaporation. The title compound is identified on the basis of the Rf value from the residue by means of flash chromatography (SiO2 60F).

c) 7-Bromoimidazo[1,5-a]pyridine

A solution of 10.75 g of N-(4-bromopyridin-2-ylmethyl)formamide in 100 ml of benzene is admixed with 8.43 g of phosphorus oxychloride. The reaction mixture is heated to reflux over 4 hours. The reaction mixture is subsequently cooled to room temperature and concentrated by evaporation, and the residue is admixed with 200 ml of water. The aqueous solution is basified with 1M NaOH and extracted with dichloromethane (3×300 ml). The combined organic phases are washed with 300 ml of water, dried over sodium sulphate and concentrated by evaporation. The title compound is identified on the basis of the Rf value from the residue by means of flash chromatography (SiO2 60F).

d) N-(4-Bromopyridin-2-ylmethyl)formamide 20.00 g of C-(4-bromopyridin-2-yl)methylamine are taken up in 60 ml of formic acid and the solution is heated to reflux over 3 hours. The reaction solution is cooled to room temperature and concentrated by evaporation, and the residue is taken up in saturated aqueous sodium hydrogencarbonate solution (300 ml) and the aqueous solution is extracted with dichloromethane (3×300 ml). The combined organic phases are washed with water (300 ml), dried over sodium sulphate and concentrated by evaporation. The title compound is identified on the basis of the Rf value from the residue by means of flash chromatography (SiO2 60F).

e) C-(4-Bromopyridin-2-yl)-methylamine

A solution of 18.70 g of 4-bromopyridine-2-carbonitrile [62150-45-2] in 200 ml of tetrahydrofuran is admixed under argon dropwise with 500 ml of 1M borane-tetrahydrofuran complex solution. The reaction solution is subsequently left to stand at room temperature for 16 hours. The reaction solution is cooled to 0° C., admixed dropwise with 500 ml of 2M HCl and heated to reflux for 30 minutes. The reaction solution is cooled to room temperature, basified with 2M NaOH, saturated with sodium chloride and extracted with tetrahydrofuran (3×300 ml). The combined organic phases are dried over sodium sulphate and concentrated by evaporation. The title compound is identified on the basis of the Rf value from the residue by means of flash chromatography (SiO2 60F).

25 7-Bromo-1-(3-methoxypropyl)-3-methylimidazo[1,5-a]pyridine

Analogously to residue 24, 1.0 g of 7-bromo-1-(3-methoxypropenyl)-3-methylimidazo[1,5-a]pyridine is reacted. The title compound is identified on the basis of the Rf value.

The starting material is prepared as follows:

a) 7-Bromo-1-(3-methoxypropenyl)-3-methylimidazo[1,5-a]pyridine

A solution of 1.59 g of 7-methoxy-1,1,1-triphenyl-3-(4-bromopyridin-2-yl)-2-aza-1,$\lambda^5$-phosphaheptane-1,3-diene in 10 ml of anhydrous chloroform is admixed with a solution of 0.132 g of acetaldehyde in 5 ml of chloroform. The reaction solution is left to stand at room temperature over 48 hours and subsequently concentrated by evaporation. The title compound is identified on the basis of the Rf value by means of flash chromatography (SiO2 60F).

b) 7-Methoxy-1,1,1-triphenyl-3-(4-bromopyridin-2-yl)-2-aza-1,$\lambda^5$-phosphaheptane-1,3-diene 4.62 g of (4-methoxybutyl)triphenylphosphonium iodide are taken up in 5 ml of anhydrous benzene under argon and 6.3 ml of a methyllithium solution (1.6M in diethyl ether) are added dropwise. The solution is heated to reflux and the resulting suspension is subsequently cooled to 0° C. A solution of 1.83 g of 4-bromopyridine-2-carbonitrile [62150-45-2] in 4 ml of benzene is added and the reaction mixture is stirred at room temperature over 120 hours. Dichloromethane is added and the lithium salts are filtered off through Hyflo. The filtrate is concentrated. The title compound is identified on the basis of the Rf value from the residue by means of flash chromatography (Alox).

c) (4-Methoxybutyl)triphenylphosphonium iodide 10.70 g of 4-methoxybutyl iodide are taken up in 80 ml of acetonitrile. 14.43 g of triphenylphosphine are added and the reaction solution is heated to reflux for 16 hours. The reaction solution is concentrated by evaporation and the residue is admixed with diethyl ether. The suspension is stirred at room temperature for 30 minutes and the precipitated solid is filtered off and dried. The title compound is used for the next stage without further purification.

26 6-Bromo-3-(3-methoxypropyl)-[1,2,4]triazolo[4,3-a]pyridine

A mixture of 18.80 g of (5-bromopyridin-2-yl)hydrazine [77992-44-0] and 14.54 g of methyl 4-methoxybutyrate [29006-01-7] is heated to reflux over 16 hours. The reaction solution is subsequently cooled and purified by means of flash chromatography (SiO2 60F). The title compound is identified on the basis of the Rf value.

28 4-Bromo-2-(3-methoxypropoxy)pyridine 11 mmol of silver carbonate and 20 mmol of 1-iodo-3-methoxypropane [61542-10-7] are added under an argon atmosphere to a solution of 21 mmol of 4-bromo-1H-pyridin-2-one [36953-37-4] in 30 ml of benzene. The reaction mixture is heated to 45° C. with exclusion of light for 2 days. The mixture is cooled to room temperature and filtered through Hyflo. The filtercake is washed with benzene and with saturated aqueous sodium hydrogencarbonate solution. The phases of the filtrate are separated and the aqueous phase is extracted with dichloromethane (3×). The combined organic phases are dried over sodium sulphate and concentrated by evaporation. The title compound is identified on the basis of the Rf value by means of flash chromatography (SiO2 60F).

29 4-Bromo-2-(4-methoxybutyl)pyridine

A solution of 3.17 mmol of 4-bromopyridine [1120-87-2] in 10 ml of tetrahydrofuran is cooled to −78° C. and a solution of 3.49 mmol of 4-methoxybutylmagnesium chloride [634590-61-7] in 5 ml of diethyl ether is added. 3.17 mmol of phenyl chloroformate are added dropwise and the reaction mixture is stirred at −78° C. for 10 minutes. Subsequently, the mixture is warmed to room temperature and quenched with 20% aqueous ammonium chloride solution. The phases of the filtrate are separated and the aqueous phase is extracted with diethyl ether. The combined organic phases are washed successively with water, 10% aqueous HCl, water and brine, dried over sodium sulphate and concentrated by evaporation. The residue is dissolved in 10 ml of toluene and 3.5 mmol of 3,4,5,6-tetrachloro-1,2-benzoquinone and 7 ml of acetic acid are added. The reaction mixture is stirred at room temperature for 24 hours and basified with 10% aqueous NaOH. The mixture is stirred at 0° C. for 15 minutes and filtered through Hyflo. The organic phase is extracted with 10% aqueous HCl (3×)—the combined aqueous phases are basified with 20% aqueous NaOH and extracted with dichloromethane (3×). The combined organic phases are dried over sodium sulphate and concentrated by evaporation. The title compound is identified on the basis of the Rf value from the residue by means of flash chromatography (SiO2 60F).

Alternatively, 4-bromo-2-(4-methoxybutyl)pyridine can be prepared as follows:

a) A solution of 1.6 mmol of 4-bromo-2-(4-methoxybut-1(E,Z)-enyl)pyridine in 30 ml of methanol is hydrogenated under a hydrogen atmosphere over 0.16 mmol of palladium/carbon at 0° C. for 40 minutes. The mixture is filtered from the catalyst and concentrated by evaporation. The title compound is identified on the basis of the Rf value from the residue by means of flash chromatography (SiO2 60F).

b) 4-Bromo-2-(4-methoxybut-1(E,Z)pyridine

Analogously to residue 1a, 2,4 mmol of (3-methoxypropyl)triphenylphosphonium bromide [111088-69-8] and 1.6 mmol of 4-bromopyridine-2-carbaldehyde [131747-63-2] are reacted. The title compound (E,Z mixture) is identified on the basis of the Rf value.

31
4-Bromo-2-(3-methoxypropoxy)-6-methylpyridine

Analogously to residue 28, 21 mmol of 4-bromo-6-methyl-1H-pyridin-2-one are reacted. The title compound is identified on the basis of the Rf value.

The starting material is prepared as follows:

a) 4-Bromo-6-methyl-1H-pyridin-2-one 16 mmol of phosphorus oxybromide are added under an argon atmosphere to a solution of 21 mmol of 4-hydroxy-6-methyl-1H-pyridin-2-one [3749-51-7] in 9 ml of N,N-dimethylformamide. The reaction mixture is heated to 110° C. for 30 minutes and subsequently cooled to room temperature, and 10 ml of water are added. The solution is brought to pH 7 by adding sodium carbonate and cooled to 0° C. The precipitate is filtered off and washed with water and diethyl ether. The title compound is identified on the basis of the Rf value.

32 4-Bromo-2-(4-methoxybutyl)-6-methylpyridine

Analogously to residue 29, 3.17 mmol of 4-bromo-2-methylpyridine [22282-99-1] are reacted. The title compound is identified on the basis of the Rf value.

Alternatively, 4-bromo-2-(4-methoxybutyl)-6-methylpyridine can be prepared as follows:
a) Analogously to residue 29a, 1.6 mmol of 4-bromo-2-(4-methoxybut-1(E,Z)-yl)-6-methylpyridine are reacted. The title compound is identified on the basis of the Rf value.

b) 4-Bromo-2-(4-methoxybut-1(E,Z)-yl)-6-methylpyridine

Analogously to residue 29b, 1.6 mmol of 4-bromo-6-methylpyridine-2-carbaldehyde [448906-71-6] are reacted. The title compound is identified on the basis of the Rf value.

33 4-Bromo-2-(4-methoxybutyl)-6-methylpyridine-N-oxide

According to methods known from the literature, the oxidation to residue 33 is carried out in the course of above described synthesis of residue 32. The title compound is identified on the basis of the Rf value.

34 6-Bromo-4-(3-methoxypropyl)-3,4-dihydro-2H-benzo[1,4]oxazine

The solution of 2.85 g of 6-bromo-4-(3-methoxypropyl)-4H-benzo[1,4]oxazin-3-one in 50 ml of tetrahydrofuran is admixed with 48 ml of 1M borane-tetrahydrofuran complex and stirred at 65° C. over 1 hour. The reaction mixture is cooled to room temperature and then admixed cautiously with 100 ml of methanol. After 10 minutes, the mixture is concentrated to dryness and the title compound is obtained as a slightly yellowish oil from the residue by means of flash chromatography (SiO2 60F). Rf=0.31 (1:2 EtOAc-heptane). Rt=4.89 (gradient I).

The starting material is prepared as follows:

a) 6-Bromo-4-(3-methoxypropyl)-4H-benzo[1,4]oxazin-3-one

The suspension of 9.87 g of 6-bromo-4H-benzo[1,4]oxazin-3-one [24036-52-0], 9.40 g of 1-chloro-3-methoxypropane, potassium fluoride on alumina (Fluka 60244), 0.144 g of potassium iodide in 500 ml of acetonitrile is stirred at 100° C. over 40 hours. The reaction mixture is cooled to room temperature and filtered through Hyflo, and the filtrate is concentrated by evaporation to dryness. The title compound is obtained as a slightly yellowish solid from the residue by crystallization from ethyl acetate. Rf=0.43 (1:1 EtOAc-heptane). Rt=4.27 (gradient I). m.p. 193-195° C.

35 Methyl 8-(2-methoxyethoxy)naphthalene-2-carboxylate

Analogously to method C, 2.02 g of methyl 8-hydroxynaphthalene-2-carboxylate [115399-09-2] and 2.08 g of 1-bromo-2-methoxyethane are reacted. The title compound is identified on the basis of the Rf value.

36 6-Bromo-3-(3-methoxy-propyl)-imidazo[1,2-a]pyrimidine 20 mmol of 6-bromo-3-(3-methoxy-prop-1(E,Z)-yl)-imidazo[1,2-a]pyrimidine are reacted according to the procedure for residue 1. The title compound is identified on the basis of its Rf-value.

The starting materials are prepared in the following way:

a) 6-Bromo-3-(3-methoxy-prop-1(E,Z)-yl)-imidazo[1,2-a]pyrimidine 10 mmol of 6-bromo-imidazo[1,2-a]pyrimidine-3-carbaldehyde are reacted according to the procedure for residue 1a. The title compound is identified based its Rf-value.

b) 6-Bromo-imidazo[1,2-a]pyrimidine-3-carbaldehyde 10 mmol 6-bromo-imidazo[1,2-a]pyrimidine are reacted according to the procedure for residue 26b. The title compound is identified based on its Rf-value.

c) 6-Bromo-imidazo[1,2-a]pyrimidine 50 mmol of 5-bromo-pyrimidin-2-ylamine are dissolved in 200 ml of saturated aqueous sodium hydrogencarbonate solution. 55 mmol of chloroacetaldehyde are added to the reaction mixture and the mixture is stirred for 24 hours at 25° C. The mixture is extracted with ethyl acetate (3×300 ml) and the combined extracts are dried over sodium sulphate and evaporated under reduced pressure. Flash chromatography (SiO2 60F) of the residue provides the title compound which is identified on the basis of its Rf-value.

37
5-Bromo-2-methoxy-3-(4-methoxy-butyl)-pyridine 0.16 mmol 10% Pd/C is added to a solution of 1.6 mmol 5-bromo-2-methoxy-3-(4-methoxy-but-1(E,Z)-enyl)-pyridine in 30 ml methanol. The reaction mixture is stirred at 0° C.

for 40 minutes under a hydrogen atmosphere. The catalyst is removed by filtration and. The title compound is obtained as a white solid from the residue by means of flash chromatography (SiO2 60F).

The starting material is prepared as follows:

a) 5-Bromo-2-methoxy-3-(4-methoxy-but-1(E,Z)-enyl)-pyridine 2.45 ml of a 1M solution of sodium-bis(trimethylsilyl) amide in tetrahydrofuran are added to a suspension of 2.4 mmol (3-methoxy-propyl)-triphenyl-phosphonium bromide [111088-69-8] in 8 ml tetrahydrofuran under an argon atmosphere at 0° C. The reaction mixture is stirred for 30 minutes at 0° C. and then 1.6 mmol 5-bromo-2-methoxy-pyridine-3-carbaldehyde [103058-87-3] are added. The reaction mixture is warmed to room temperature and then diluted with tert-butyl methyl ether. The solution is washed with saturated aqueous sodium hydrogencarbonate solution. The organic layer is dried over sodium sulphate, filtered and concentrated. The title compound is obtained from the residue by means of flash chromatography (SiO2 60F) and identified based on its Rf value

38
5-Bromo-2-methoxy-3-(3-methoxy-propoxy)-pyridine

A mixture of 21 mmol 5-bromo-3-(3-methoxy-propoxy)-1H-pyridin-2-one, 14 mmol silver carbonate and 25 mmol iodomethane in 35 ml of benzene are stirred at 40-50° C. for 24 hours with exclusion of light. The mixture is cooled in an ice bath and the silver salts are removed by filtration. The filtrate is washed with 2% aqueous sodium hydrogencarbonate solution and with water (2×). The organic layer is dried over sodium sulphate, filtered and concentrated. The title compound is obtained from the residue by means of flash chromatography (SiO2 60F) and identified based on its Rf value.

The starting material is prepared as follows:

a) 5-Bromo-3-(3-methoxy-propoxy)-1H-pyridin-2-one

To a 1.4M NaOH solution at 0° C. are added 0.9 mol 5-bromo-3-hydroxy-1H-pyridin-2-one [34206-49-0]. The mixture is allowed to stir for 15 minutes and 0.9 mmol 1-iodo-3-methoxypropane [61542-10-7] are added carefully at 0° C. The mixture is stirred at room temperature for 3 hours, then neutralized with acetic acid to pH 7. The mixture is extracted with chloroform (10×) and the organic layer is dried over sodium sulphate, filtered and concentrated. The title compound is obtained from the residue by means of flash chromatography (SiO2 60F) and identified based on its Rf value.

39
2-Iodo-5-methoxy-4-(3-methoxy-propoxy)-pyridine 2 mmol of 2,6-diiodo-3-methoxy-4-(3-methoxy-propoxy)-pyridine are added to a solution of 4 mmol n-butyllithium in 1.6 ml hexane and 10 ml tetrahydrofuran at −78° C. under an argon atmosphere. The reaction mixture is stirred at −78° C. for 15 minutes. 2 mmol of water are introduced and the reaction mixture is allowed to reach room temperature. 10% Aqueous ammonium chloride solution is added to the mixture followed by extraction with tert-butyl methyl ether (3×). The combined organic layers are dried over sodium sulphate, filtered and concentrated. The title compound is obtained from the residue by means of flash chromatography (SiO2 60F) and identified based on its Rf value.

The starting material is prepared as follows:

a) 2,6-Diiodo-3-methoxy-4-(3-methoxy-propoxy)-pyridine

To a stirred solution of 60 mmol NaOH in 50 ml N,N-dimethyl formamide is progressively added 50 mmol 2,6-diiodo-3-methoxy-pyridin-4-ol [437709-87-0]. The reaction mixture is stirred for 30 minutes and then cooled to 0° C. 60 mmol 1-iodo-3-methoxy-propane [61542-10-7] are added and the mixture is stirred for 15 minutes at room temperature. Water and ethyl acetate are added to the mixture, the layers are separated and the aqueous layer is extracted with ethyl acetate (3×). The combined organic layers are dried over sodium sulphate, filtered and concentrated. The title compound is obtained from the residue by means of flash chromatography (SiO2 60F) and identified based on its Rf value,

40 2-Iodo-5-methoxy-4-(4-methoxy-butyl)-pyridine 2 mmol of 2,6-diiodo-3-methoxy-4-(4-methoxy-butyl)-pyridine are added to a solution of 4 mmol n-butyllithium in 1.6 ml hexane and 10 ml tetrahydrofuran at −78° C. under an argon atmosphere. The reaction mixture is stirred at −78° C. for 15 minutes. 2 mmol of water are introduced and the reaction mixture is warmed to room temperature. 10% Aqueous ammonium chloride solution is added to the mixture followed by extraction with tert-butyl methyl ether (3×). The combined organic layers are dried over sodium sulphate, filtered and concentrated. The title compound is obtained from the residue by means of flash chromatography (SiO2 60F) and identified based on its Rf value.

The starting materials are prepared as follows:

a) 2,6-Diiodo-3-methoxy-4-(4-methoxy-butyl)-pyridine

To a stirred solution of 60 mmol NaOH in 50 ml N,N-dimethyl formamide is progressively added 50 mmol 2,6-diiodo-4-(4-methoxy-butyl)-pyridin-3-ol. The reaction mixture is stirred for 30 minutes and then cooled to 0° C. 60 mmol methyl iodide are added and the mixture is stirred for 15 minutes at room temperature. Water and ethyl acetate are added to the mixture, the layers are separated and the aqueous layer is extracted with ethyl acetate (3×).

The combined organic layers are dried over sodium sulphate, filtered and concentrated. The title compound is obtained from the residue by means of flash chromatography (SiO2 60F) and identified based on its Rf value.

b) 2,6-Diiodo-4-(4-methoxy-butyl)-pyridin-3-ol

To a stirred solution of 0.1 mol 4-(4-methoxy-butyl)-pyridin-3-ol and 0.21 mol sodium carbonate in 1 l water at 20 ° C. is added 0.1 mol iodine. The mixture is stirred until the color disappears. The reaction mixture is adjusted to pH 3 with concentrated HCl. The formed solid is collected by filtration. The title compound is obtained from the solid by re-crystallization from ethanol and identified based on its Rf value.

c) 4-(4-Methoxy-butyl)-pyridin-3-ol

A mixture of 39 mmol acetic acid 4-(4-methoxy-butyl)-pyridin-3-yl ester in 20 ml acetic acid is heated to 70° C. for 30 minutes. After cooling, 75 ml of diethyl ether/pentane (1:5) is added and the precipitate is collected by filtration. The title compound is obtained from the solid by re-crystallization from toluene and identified based on its Rf value.

d) Acetic acid 4-(4-methoxy-butyl)-pyridin-3-yl ester

To a degassed solution of 9.9 mmol acetic acid 4-(4-methoxy-but-1-ynyl)-pyridin-3-yl ester and 0.51 mmol quinoline in 230 ml ethyl acetate is added 0.56 mmol 10% Pd/C. The suspension is vigorously stirred under an atmospheric pressure of hydrogen for 2 hours. The catalyst is removed by filtration and the solvent is evaporated. The title compound is obtained from the residue by means of flash chromatography (SiO2 60F) and identified based on its Rf value.

e) Acetic acid 4-(4-methoxy-but-1-ynyl)-pyridin-3-yl ester 0.95 mmol Palladium dichloride bis-triphenylphoshine and 0.97 mmol cupric chloride are dissolved in 64 ml tetrahydrofuran under an argon atmosphere. A solution of 30 mmol acetic acid 4-iodo-pyridin-3-yl ester [289473-46-7] and 38 mmol 4-methoxy-but-1-yne [36678-08-7] in 50 ml tetrahydrofuran is added in one portion and the reaction mixture is stirred at room temperature for 1 hour. 300 ml of diethyl ether are added and the precipitate is filtered off. The filtrate is washed successively with saturated, aqueous ammonium chloride solution (3×), water (2×) and brine. The organic layer is dried over sodium sulphate, filtered and concentrated. The title compound is obtained from the residue by means of flash chromatography (SiO2 60F) and identified based on its Rf value.

41 6-Bromo-1-(3-methoxy-propyl)-3-methyl-1H-indazole

A mixture of 10.90 g methanesulfonic acid 2-acetyl-5-bromo-phenyl ester, 7.75 g of (3-methoxy-propyl)-hydrazine and 7.17 g of ammonium acetate in 100 ml of o-xylene is refluxed for 3 days with continuous separation of the water which is formed during the reaction. The reaction mixture is then cooled to room temperature and concentrated by evaporation. The title compound is obtained as an orange-yellow oil from the residue by means of flash chromatography (SiO2 60F). Rf=0.38 (1:1 EtOAc-heptane). Rt=4.52 (gradient I).

The starting materials are prepared as follows:

a) Methanesulfonic acid 2-acetyl-5-bromo-phenyl ester 4.42 ml of methanesulphonyl chloride are added dropwise to a solution of 10.0 g 1-(4-bromo-2-hydroxy-phenyl)-ethanone [30186-18-6] and 13.0 ml of triethylamine in 200 ml dichloromethane at 0° C. The reaction mixture is worked up after 1 hour by pouring into 250 ml cold 1N HCl and extracting with tert-butyl methyl ether (2×)—the combined organic layers are washed successively with water and brine, dried over sodium sulphate and concentrated by evaporation. The title compound is obtained as light yellow crystals from the residue by re-crystallization from diisopropyl ether. Rf=0.51 (1:1 EtOAc-heptane). Rt=3.94 (gradient I). m.p. 62.0-62.1° C.

b) (3-Methoxy-propyl)-hydrazine 22.0 g of 1-bromo-3-methoxy-propane [36865-41-5] are added dropwise to a mixture of 130 ml of hydrazine hydrate in 40 ml of ethanol at room temperature. After stirring for 2 hours, the reaction mixture is warmed to 40° C. for 1 hour, re-cooled to room temperature and then concentrated by evaporation. The residue is then continuously extracted with diethyl ether for 2 days—the cooled ether solution is dried over sodium sulphate and concentrated by evaporation to provide the crude title compound as a yellow oil, which is used in the next step without any further purification.

Residues $NR^1R^2$:

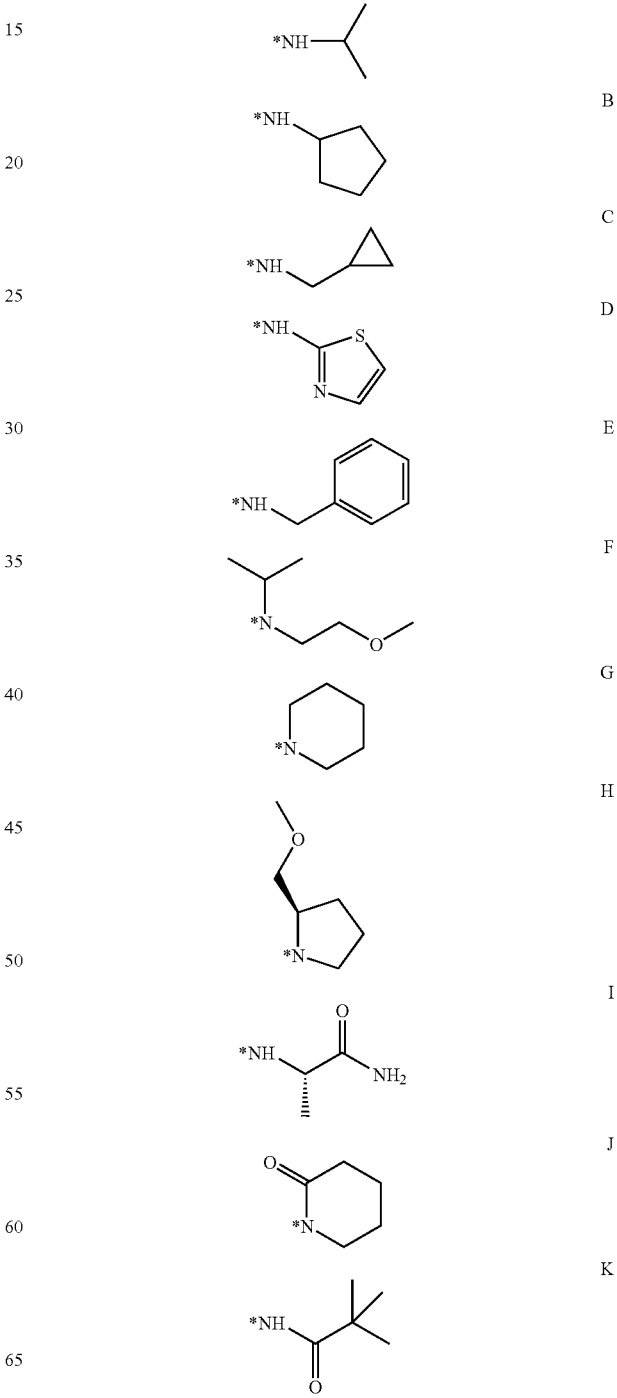

-continued
| | |
|---|---|
| L 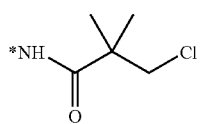 | W 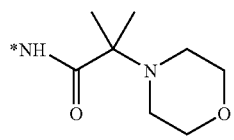 |
| M 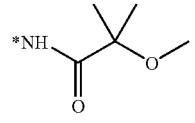 | X 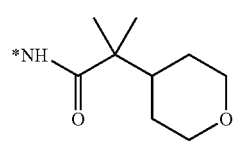 |
| N 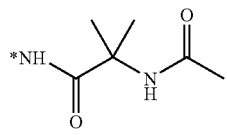 | Y 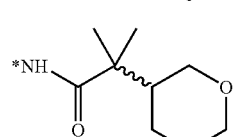 |
| O 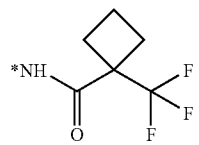 | Z 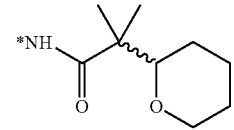 |
| P 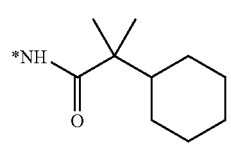 | AA 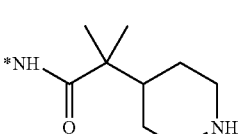 |
| Q 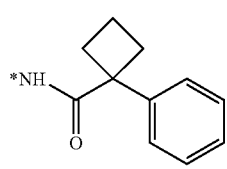 | BB 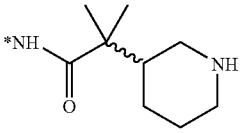 |
| R 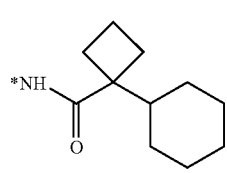 | CC 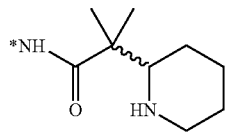 |
| S 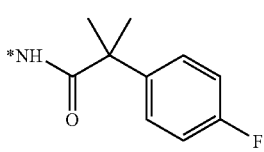 | DD 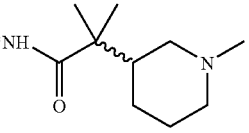 |
| T 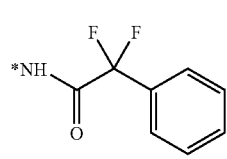 | EE 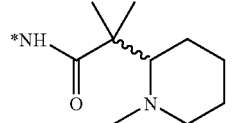 |
| U 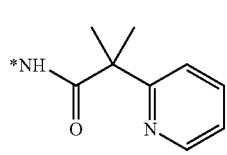 | FF 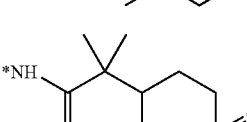 |
| V 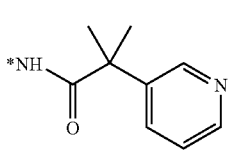 | GG 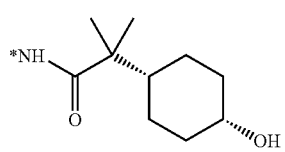 |

-continued
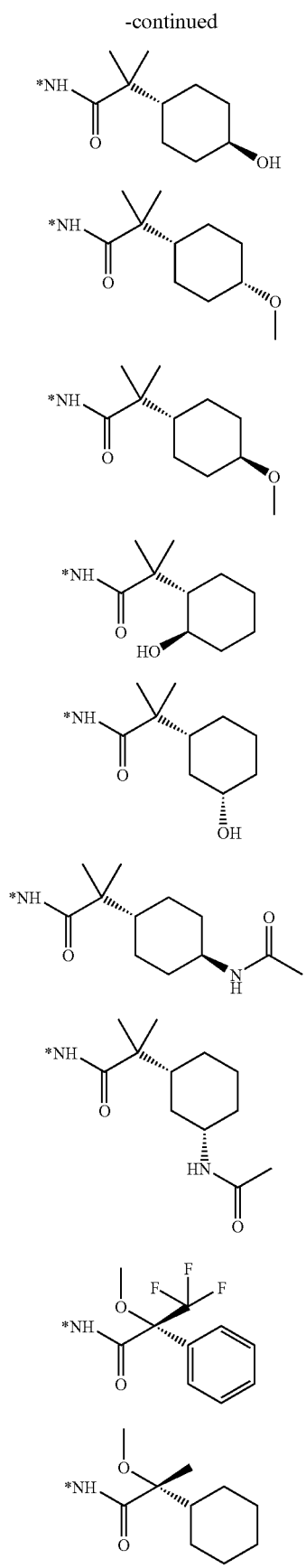
-continued
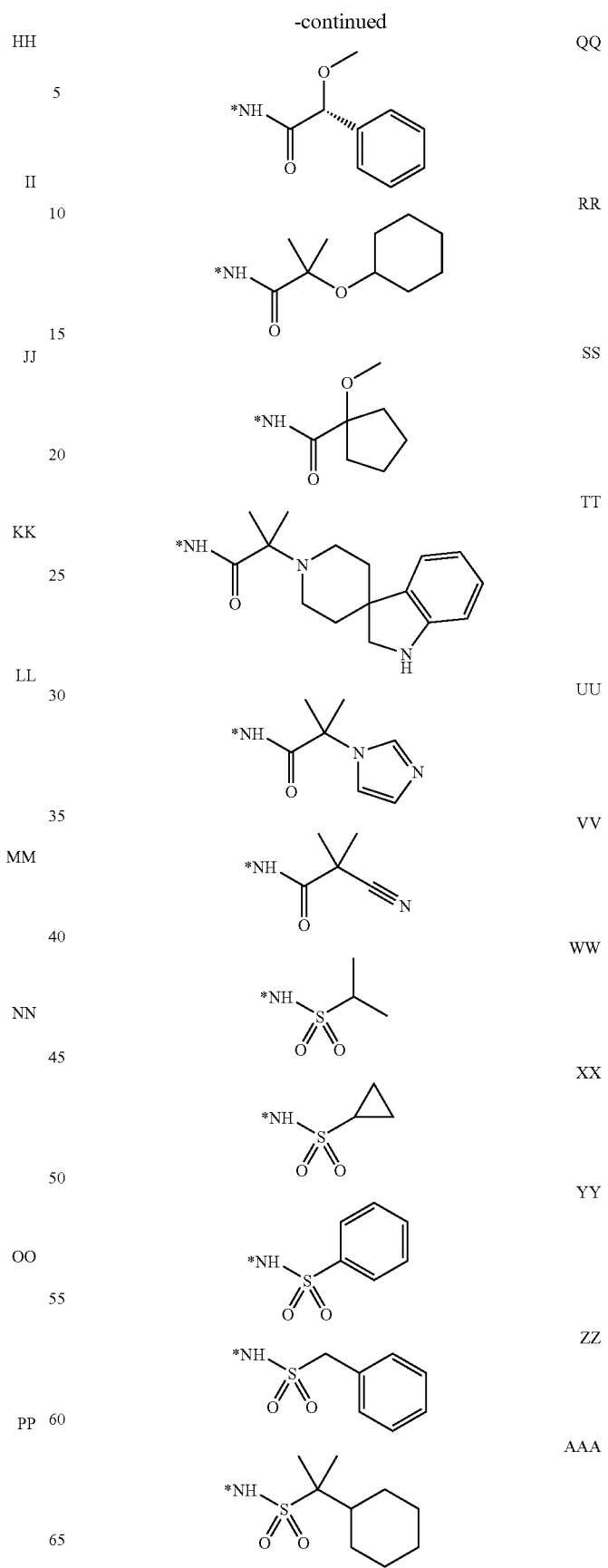

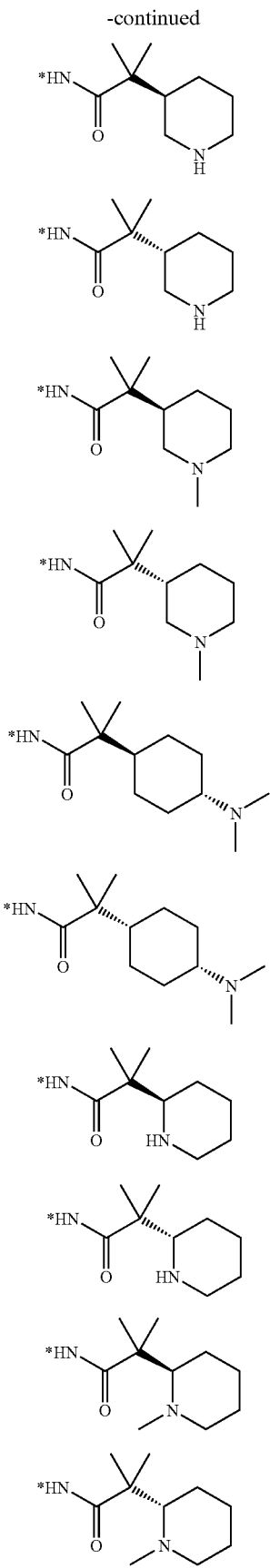
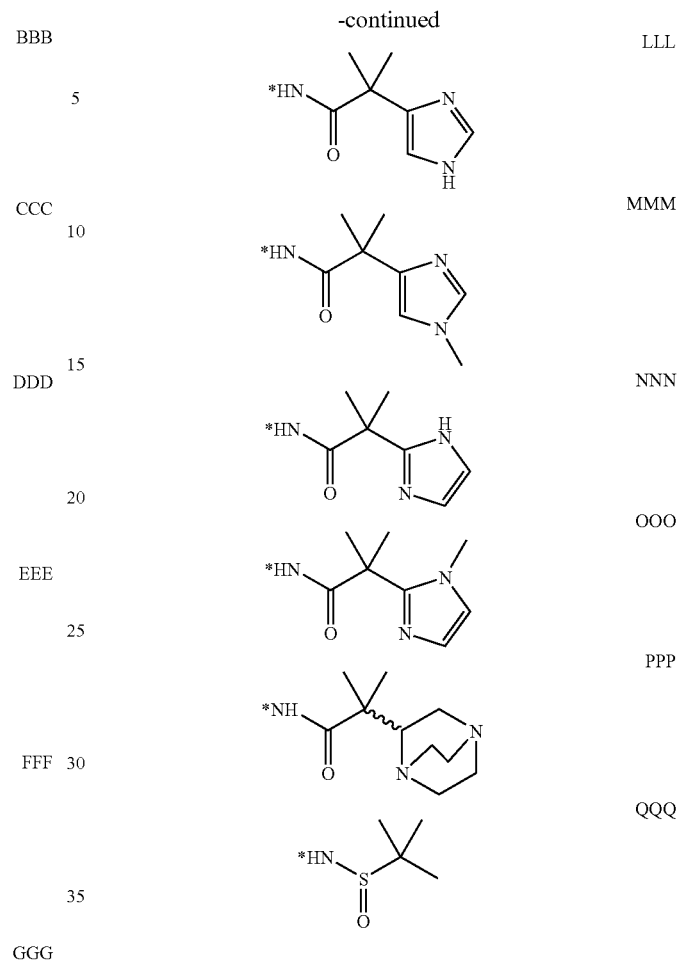

The protected or unprotected amines corresponding to above residues $NR^1R^2$ or corresponding precursors are prepared according to methods known from the literature and as exemplified as follows:

R 1-Cyclohexyl-cyclobutanecarboxylic acid

A mixture of 2.04 g 1-(4-chloro-phenyl)-cyclobutanecarboxylic acid [50921-39-6], 0.875 g sodium acetate and 0.20 g 10% Pd/C in 15 ml of methanol is hydrogenated at room temperature and 0.1 bar for 1 hour. The catalyst is removed by filtration over Hyflo and the filtrate is charged with 0.20 g of Nishimura's catalyst. The mixture is hydrogenated at room temperature and 4 bar for 1.5 hours. The catalyst is removed by filtration over Hyflo and concentrated by evaporation to provide the title compound as a colourless oil which is used without further purification. Rt=4.44 (gradient I).

U 2-Methyl-2-pyridin-2-yl-propionic acid

A solution of 0.275 g of 2-methyl-2-pyridin-2-yl-propionic acid methyl ester [CAS 476429-22-8] in 10 ml of methanol at room temperature is admixed with 3.65 ml of 1M aqueous lithium hydroxide solution. After stirring for 12 hours, the reaction mixture is adjusted to pH 6-7 with 1M HCl and concentrated by evaporation. The residue is dissolved in 60 ml of 5:1 ethyl acetate/methanol, dried over sodium sulphate and concentrated by evaporation to provide the crude title compound as a yellow solid which is used without further purification.

X 2-Methyl-2-(tetrahydro-pyran-4-yl)-propionic acid

A solution of 0.795 g of 2-methyl-2-(tetrahydro-pyran-4-yl)-propionic acid ethyl ester in 3 ml of ethanol is admixed with 3 ml of a 40% aqueous potassium hydroxide solution and then heated to reflux. After 4 hours, the reaction mixture is cooled to room temperature and the ethanol removed in vacuo. The remaining aqueous solution is acidified (pH 2-3) with 4M HCl and then extracted with tert-butyl methyl ether (2×). The combined organic layers are washed with water and brine, dried over sodium sulphate and concentrated by evaporation to provide the crude title compound as a yellow solid. Rf=0.10 (1:3 EtOAc-heptane).

The starting material is prepared as follows:

a) 2-Methyl-2-(tetrahydro-pyran-4-yl)-propionic acid ethyl ester

A solution of 1 g (tetrahydro-pyran-4-yl)-acetic acid ethyl ester [103260-44-2] in 3 ml of dry tetrahydrofuran is added dropwise to a solution of lithium diisopropyl amide (freshly prepared from 1 ml diisopropyl amine and 4.3 ml 1.6 M butyllithium solution in hexanes) in 5 ml of dry tetrahydrofuran at −78° C. The reaction mixture is stirred for 15 minutes at −78° C. and then 0.46 ml of methyl iodide are added and the mixture is allowed to warm to 0° C. over a period of 15 minutes. The reaction mixture is re-cooled to −78° C. and then a solution of lithium diisopropyl amide (freshly prepared from 1 ml diisopropyl amine and 4.3 ml 1.6 M butyllithium solution in hexanes) in 5 ml of dry tetrahydrofuran is added dropwise. The solution is stirred for 15 minutes at −78° C. and then 0.46 ml of methyl iodide are added and the mixture is allowed to warm to room temperature. After 2 hours, the reaction mixture is quenched with 20 ml of 1M HCl and then extracted with tert-butyl methyl ether (2×). The combined organic phases are washed with brine, dried over sodium sulphate and concentrated by evaporation. The title compound is obtained as a colourless oil from the residue by means of flash chromatography (SiO2 60F). Rf=0.27 (1:5 EtOAc-heptane).

AA tert-Butyl 4-(1-carboxy-1-methylethyl)piperidine-1-carboxylate 0.052 g of methyl 2-methyl-2-piperidin-4-ylpropionate hydrochloride is taken up in 2 ml of dioxane and the mixture is admixed with 2 ml of 3M NaOH. The reaction mixture is stirred at room temperature for 30 minutes and 0.079 g of di-tert-butyl dicarbonate are added. The reaction mixture is subsequently stirred at room temperature for 16 hours, adjusted to pH=6 with 2M HCl and extracted with ethyl acetate (2×). The combined organic phases are washed with brine, dried over sodium sulphate and concentrated. The title compound is obtained as a colourless oil from the residue by means of flash chromatography (SiO2 60F). Rf=0.45 (1:2 EtOAc-heptane).

The starting material is prepared as follows:

a) Methyl 2-methyl-2-piperidin-4-ylpropionate hydrochloride 0.115 g of methyl 2-methyl-2-pyridin-4-ylpropionate [79757-27-0] are dissolved in 5 ml of methanol in an autoclave. The solution is admixed with 0.35 ml of 1.2M HCl in methanol and 0.012 g of platinum(IV) oxide and the reaction mixture is hydrogenated at 4 bar and 23° C. over 46 hours. The catalyst is filtered off through Hyflo and the filtrate is concentrated by evaporation. The title compound is obtained as a light brown residue. Rf=0.05 (200:20:1 dichloromethane-methanol-25% conc. ammonia).

DD 2-Methyl-2-(1-methyl-piperidin-3(R,S)-yl)-propionic acid 0.200 g of 2-methyl-2-(1-methyl-piperidin-3(R,S)-yl)-propionic acid methyl ester are dissolved in 4 ml of methanol. 4 ml of a 1M aqueous lithium hydroxide solution are added and the mixture is stirred for 16 hours at room temperature. The reaction mixture is neutralised with 1M HCl and extracted with ethyl acetate (3×50 ml). The organic phases are combined and concentrated by evaporation. The residue is purified by means of flash chromatography (SiO2 60F) to provide the title compound as a colourless oil. Rf 0.15 (150:54:10:1 dichloromethane-methanol-acetic acid-water).

The starting materials are prepared as follows:

a) 2-Methyl-2-(1-methyl-piperidin-3(R,S)-yl)-propionic acid methyl ester 0.370 g of 2-methyl-2-piperidin-3(R,S)-yl-propionic acid methyl ester hydrochloride are dissolved in 0.5 ml of 3M NaOH. 2 ml of formic acid and 0.19 ml of formaldehyde (35% aqueous solution) are added and the reaction solution is warmed to 60° C. for 20 hours. The solution is cooled to room temperature, neutralised with 3M NaOH to pH 8-9 and extracted with dichloromethane (3×10 ml). The combined organic phases are washed with water (10 ml), dried over sodium sulphate and concentrated by evaporation. The residue is purified by means of flash chromatography (SiO2 60F) to provide the title compound as a colourless oil. Rf 0.19 (200:20:1 dichloromethane-methanol-25% conc. ammonia).

b) 2-Methyl-2-piperidin-3(R,S)-yl-propionic acid methyl ester hydrochloride

A mixture of 0.823 g of 2-methyl-2-pyridin-3-yl-propionic acid methyl ester [476429-23-9] and 0.062 g of platinum(IV) oxide hydrate in 8 ml of methanol and 1.7 ml of 1.2M HCl in methanol at room temperature is hydrogenated for 5.5 hours. The catalyst is removed by filtration over Hyflo and the filtrate is concentrated by evaporation to provide the crude title compound as a brown oil which is used in the next step without further purification.

GG 2-(cis-4-Hydroxy-cyclohexyl)-2-methyl-propionic acid 0.200 g of 2-(cis-4-hydroxy-cyclohexyl)-2-methyl-propionic acid methyl ester are dissolved in 4 ml of methanol. 4 ml of a 1M aqueous lithium hydroxide solution are added and the mixture is stirred for 16 hours at room temperature. The reaction mixture is then neutralised with 1M HCl and concentrated by evaporation. The title compound is identified from the residue by means of flash chromatography (SiO2 60F) based on its Rf value.

The starting materials are prepared as follows:

a) 2-(cis-4-Hydroxy-cyclohexyl)-2-methyl-propionic acid methyl ester and 2-(trans-4-Hydroxy-cyclohexyl)-2-methyl-propionic acid methyl ester A solution of 2.0 g of 2-(cis/trans-4-hydroxy-cyclohexyl)-2-methyl-propionic acid in 40 ml of methanol is cooled to 0° C. 20 ml of a 2M trimethylsilyldiazomethane solution in hexanes are added dropwise and the reaction solution is left to stand at room temperature for 1 hour. The solution is concentrated under reduced pressure and the residue taken up in ethyl acetate. The solution is washed with saturated aqueous sodium carbonate solution and brine, dried over sodium sulphate and concentrated by evaporation. The residue is purified by flash chromatography (SiO2 60F) to provide the title compounds as colourless oils, the cis isomer eluting first. Rf (cis)=0.11 (1:3 EtOAc-heptane); Rf (trans)=0.09 (1:3 EtOAc-heptane).

b) 2-(cis-4-Hydroxy-cyclohexyl)-2-methyl-propionic acid 2.690 g of 2-(4-hydroxy-phenyl)-2-methyl-propionic acid [29913-51-7] are dissolved in 20 ml of water and 30 ml of 1M NaOH solution. 0.200 g of Raney-Nickel are added and the reaction mixture is hydrogenated at 50 bar and 150° C. for 24 hours. The catalyst is removed by filtration over Hyflo and the filtrate is concentrated by evaporation. The residue is taken up in 200 ml of water and the solution neutralized with 1M HCl to pH 6. The reaction mixture is then extracted with dichloromethane (2×200 ml) and ethyl acetate (2×20 ml) and the combined organic phases are dried over sodium sulphate and concentrated by evaporation to provide the title compounds as a ca. 1:4 mixture of cis/trans-isomers. The white solid is used for the next step without further purification.

II 2-(cis-4-Methoxy-cyclohexyl)-2-methyl-propionic acid 0.200 g of 2-(cis-4-methoxy-cyclohexyl)-2-methyl-propionic acid methyl ester are dissolved in 4 ml of methanol. 4 ml of a 1M aqueous lithium hydroxide solution is added and the mixture is stirred for 16 hours at room temperature. The reaction mixture is then neutralised with 1M HCl and concentrated under reduced pressure The title compound is identified from the residue by means of flash chromatography (SiO2 60F) based on its Rf value.

The starting material is prepared as follows:

a) 2-(cis-4-Methoxy-cyclohexyl)-2-methyl-propionic acid methyl ester 0.500 g of 2-(cis-4-hydroxy-cyclohexyl)-2-methyl-propionic acid methyl ester (residue GGa) are dissolved in 5 ml of dry tetrahydrofuran. 0.120 g of sodium hydride (60% dispersion) is added in portions and the mixture stirred at 40° C. for 1 hour. Methyl iodide (0.233 ml) is added and the mixture heated to 40° C. for 5 hours. The reaction mixture is then cooled to room temperature, quenched with 5 ml of water and extracted with tert-butyl methyl ether (2×50 ml). The combined organic phases are dried over sodium sulphate and concentrated by evaporation. The title compound is identified from the residue by means of flash chromatography (SiO2 60F) based on its Rf value.

KK trans-2-[2-tert-Butyl-dimethyl-silanyloxy)-cyclohexyl]-2-methyl-propionic acid Imidazole (0.310 g) is added to a solution of 0.337 g trans-(2-(2-hydroxy-cyclohexyl)-2-methyl propionic acid [34440-72-7] and 0.682 g tert-butyl-dimethyl-chlorosilane in 7 ml of dry N,N-dimethylformamide. The mixture is left to stand at room temperature for 2 hours and is then warmed to 50° for 12 hours. The reaction mixture is poured onto water (30 ml) and the mixture is extracted with tert-butyl methyl ether (2×50 ml). The combined organic phases are washed with saturated aqueous sodium bicarbonate solution (30 ml) and brine (30 ml), dried over sodium sulphate and concentrated under reduced pressure. The residue is taken up in 9 ml of methanol and 3 ml of tetrahydrofuran and the resulting mixture is treated for 1 hour at room temperature with a 10% aqueous potassium carbonate solution (3 ml). The reaction solution is concentrated under reduced pressure to half of the initial volume and the pH is adjusted to 5 with 1M HCl. The mixture is extracted with tert-butyl methyl ether (2×50 ml) and the combined organic phases are washed with brine, dried over sodium sulphate and concentrated under reduced pressure. The residue is purified by means of flash chromatography (SiO2 60F) to provide the title compound as white solid. Rf 0.64 (1:2 EtOAc-heptane).

LL 2-(3(S)-Hydroxy-cyclohex-1(R)-yl)-2-methyl-propionic acid 1.00 g of 2-(3(S)-hydroxy-cyclohex-1(R)-yl)-2-methyl-propionic acid ethyl ester are dissolved in 30 ml of methanol. 30 ml of a 1M aqueous lithium hydroxide solution are added and the mixture is stirred for 16 hours at room temperature. The reaction mixture is neutralised with 1M HCl and concentrated by evaporation. The title compound is identified from the residue by means of flash chromatography (SiO2 60F) based on its Rf value.

The starting materials are prepared as follows:

a) 2-(3(S)-Hydroxy-cyclohex-1(R)-yl)-2-methyl-propionic acid ethyl ester 3 ml of 1M tetrabutylammonium fluoride solution in tetrahydrofuran are added to a solution of 1.00 g of 2-[3(S)-(tert-butyl-dimethylsilanyloxy)-cyclohex-(1R)-yl]-2-methyl-propionic acid ethyl ester in 3 ml of tetrahydrofuran at 0° C. The reaction is left to stand at room temperature for 1 hour and is then diluted with tert-butyl methyl ether (20 ml) and washed with water (20 ml) and brine (20 ml). The organic layer is dried over sodium sulphate and concentrated by evaporation. The title compound is identified from the residue by means of flash chromatography (SiO2 60F) based on its Rf value.

b) 2-[3(S)-(tert-Butyl-dimethylsilanyloxy)-cyclohex-1(R)-yl]-2-methyl-propionic acid ethyl ester A solution of 21 ml lithium diisopropylamide (ca. 1M in tetrahydrofuran/hexanes) is cooled to −78° C. A solution of 3.72 g [3(S)-(tert-butyl-dimethyl-silanyl-oxy)-cyclohex-1(R)-yl]-acetic acid ethyl ester (197091-18-2) in 20 ml of tetrahydrofuran is added dropwise over a period of 15 minutes while maintaining the temperature at −78° C. The reaction solution is stirred for 30 minutes at −78° C. and methyl iodide (1.31 ml) is added in one portion. The reaction mixture is warmed to 0° C. over a period of 30 minutes and is then cooled again to −78° C. Lithium diisopropylamide-solution (21 ml) is added dropwise over a period of 15 minutes and the reaction mixture is stirred for 30 minutes at −78° C. 1.31 ml Methyl iodide are added in one portion and the reaction mixture is warmed to room temperature over a period of 16 hours. The reaction mixture is quenched with 0.1M HCl (50 ml) and is then extracted with tert-butyl methyl ether (3×50 ml). The combined organic phases are washed with brine (50 ml), dried over sodium sulphate and concentrated by evaporation. The title compound is identified from the residue by means of flash chromatography (SiO2 60F) based on its Rf value.

MM trans-2-(4-Acetylamino-cyclohexyl)-2-methyl-propionic acid 0.200 g of trans-2-(4-acetylamino-cyclohexyl)-2-methyl-propionic acid methyl ester are dissolved in 4 ml of methanol. 4 ml of a 1M aqueous lithium hydroxide solution are added and the mixture is stirred for 16 hours at room temperature. The reaction mixture is neutralised with 1M HCl and extracted with ethyl acetate (3×50 ml)—the combined organic phases are concentrated by evaporation. The title compound is identified from the residue by means of flash chromatography (SiO2 60F) based on its Rf value.

The starting materials are prepared as follows:

a) trans-2-(4-Acetylamino-cyclohexyl)-2-methyl-propionic acid methyl ester

A round bottom flask is charged with 0.422 g of trans-2-(4-azido-cyclohexyl)-2-methyl-propionic acid methyl ester. 0.71 ml of thioacetic acid are added and the solution is stirred for 1 hour at room temperature. After completion of the reaction, the reaction mixture is concentrated by evaporation. The title compound is identified from the residue by means of flash chromatography (SiO2 60F) based on its Rf value.

b) trans-2-(4-Azido-cyclohexyl)-2-methyl-propionic acid methyl ester

Sodium azide (0.761 g) is added to a solution of 0.898 g of cis-2-(4-methanesulphonyloxy-cyclohexl)-2-methyl-propionic acid methyl ester in 7 ml of N,N-dimethylformamide. The reaction mixture is warmed to 100° C. for 16 hours. The mixture is cooled to room temperature, diluted with 20 ml of water and extracted with tert-butyl methyl ether (3×30 ml). The combined organic phases are washed with brine (20 ml), dried over sodium sulphate and concentrated by evaporation. The title compound is identified from the residue by means of flash chromatography (SiO2 60F) based on its Rf value.

c) cis-2-(4-Methanesulphonyloxy-cyclohexl)-2-methyl-propionic acid methyl ester A solution of 1.00 g of 2-(cis4-hydroxy-cyclohexyl)-2-methyl-propionic acid methyl ester (residue GGa), 1.38 ml triethylamine and 0.061 g of 4-dimethylaminopyridine in 20 ml of dichloromethane is cooled to 0° C. Methanesulphonychloride (0.50 ml) is added and the solution is left to stand at room temperature for 16 hours. The solution is poured onto saturated aqueous sodium hydrogen carbonate solution and the phases are separated. The aqueous phase is extracted with dichloromethane (2×50 ml)—the combined organic phases are washed with brine (50 ml), dried over sodium sulphate and concentrated by evaporation. The title compound is identified from the residue by means of flash chromatography (SiO2 60F) based on its Rf value.

PP (R)-Cyclohexyl-methoxy-acetic acid

An autoclave is charged with a solution of 1.00 g of (R)-α-methoxy-phenyl acetic acid [24190-08-7] in 20 ml methanol. 0.100 g of Nishimura catalyst are added and the mixture is hydrogenated at 4 bar and 20° C. for 1 hour. The mixture is filtered over Hyflo and the filtrate concentrated by evaporation to provide the title compound as a colourless oil. The crude material is used without further purification. Rf=0.84 (150:54:10:1 dichloromethane-methanol-water-acetic acid).

UU 2-Imidazol-1-yl-2-methyl-propionic acid 1.54 g of 2-imidazol-1-yl-2-methyl-propionic acid ethyl ester [73828-88-3] are dissolved in 20 ml of methanol. 20 ml of a 3M NaOH are added and the mixture is stirred for 16 hours at 60° C. The reaction mixture is then neutralised with 1M HCl and concentrated by evaporation. The title compound is identified from the residue by means of flash chromatography (SiO2 60F) based on its Rf value.

AAA 2-Cyclohexyl-propane-2-sulphonyl chloride 2 mmol of phosphoroxytrichloride are added to a solution of 1 mmol of 2-cyclohexyl-propane -2-sulphonic acid in acetonitrile and the reaction mixture is heated to reflux for 2 hours. The reaction mixture is cooled to room temperature, carefully quenched by the addition of water and extracted with tert-butyl methyl ether. The organic phase is dried over sodium sulphate and concentrated by evaporation. The crude title compound is used without further purification.

The starting materials are prepared as follows:

a) 2-Cyclohexyl-propane-2-sulphonic acid 10 ml of an aqueous hydrogen peroxide solution (30% wt) are added to a stirred solution of 1 mmol of 2-cyclohexyl-propane-2-thiol in acetic and the mixture is then heated at 60° C. overnight. The reaction mixture is cooled to room temperature and the solvent removed under reduced pressure. The crude title compound is used without further purification.

b) 2-Cyclohexyl-propane-2-thiol 1 mmol of thiourea is added to a stirred solution of 1 mmol of (1-bromo-1-methyl-ethyl)-cyclohexane [BRN 2424910] in methanol and the mixture is stirred for 12 hours at room temperature. The solvent is removed under reduced pressure and the residue is then suspended in 10 ml of 2N NaOH and heated at 60° C. for 3 hours. The reaction mixture is cooled to room temperature and extracted with tert-butyl methyl ether (3×). The combined organic phases are dried over sodium sulphate and concentrated by evaporation. The crude title compound is used without further purification.

BBB (R)-3-(1-carboxy-1-methyl-ethyl)-piperidine-1-carboxylic acid tert-butyl ester 1.045 g of (R)-3-(1-methoxycarbonyl-1-methyl-ethyl)-piperidine-1-carboxylic acid tert-butyl ester is taken up in 5 ml of methanol and the mixture is admixed with 5 ml of 3M NaOH. The mixture is then stirred at 60° C. for 20 hours. The methanol is removed in vacuo and the aqueous residue acidified with 2M HCl to pH 2-3. The mixture is extracted with ethyl acetate (3×) and the combined extracts are washed with brine, dried over sodium sulphate and concentrated by evaporation. The title compound is obtained as a colourless oil which can be used without further purification.

The starting materials are prepared as follows:

a) (R)-3-(1-Methoxycarbonyl-1-methyl-ethyl)-piperidine-1-carboxylic acid tert-butyl ester A solution of lithium diisopropyl amide (freshly prepared from 4.5 ml diisopropyl amine and 19 ml 1.6 M butyllithium solution in hexanes) in 20 ml of dry tetrahydrofuran is cooled to −78° C. A solution of 7.15 g (R)-3-methoxycarbonylm-ethyl-piperidine-1-carboxylic acid tert-butyl ester in 40 ml of dry tetrahydrofuran is added dropwise while maintaining the temperature between −65 to −70° C. The reaction solution is stirred for 15 min at −70° C. 2.0 ml of methyl iodide are added and the mixture is allowed to warm to −20° C. over a period of 30 minutes. The reaction mixture is cooled to −78° C. and then a solution of lithium diisopropyl amide (freshly prepared from 4.5 ml diisopropyl amine and 19 ml 1.6 M butyllithium solution in hexanes) in 20 ml of dry tetrahydrofuran is added dropwise while maintaining the temperature between −65 to −70° C. The reaction solution is stirred for 15 minutes at −70° C. 2.0 ml of methyl iodide are added and the mixture is allowed to warm to room temperature. The reaction mixture is quenched with 50 ml of 0.1M HCl and then extracted with tert-butyl methyl ether (2×). The combined organic phases are washed with brine, dried over sodium sulphate and concentrated by evaporation. The title compound is obtained as a light yellow oil from the residue by means of flash chromatography (SiO2 60F). Rf=0.36 (1:4 EtOAc-heptane).

b) (R)-3-Methoxycarbonylmethyl-piperidine-1-carboxylic acid tert-butyl ester

Triethylamine (4.8 ml) is added to a solution of methyl (R)-3-piperidine acetate hydrochloride (Arch Corp.) in 100 ml of dichloromethane. The reaction solution is cooled to 0° C. and di-tert-butyl dicarbonate is added portionwise. The reaction solution is left to stand at room temperature for 16 hours and is then poured onto a saturated aqueous sodium hydrogencarbonate solution. The layers are separated and the aqueous layer is extracted with dichloromethane. The combined organic layers are washed with water, dried over sodium sulphate and concentrated by evaporation. The title compound is obtained as a colourless oil from the residue by means of flash chromatography (SiO2 60F). Rf=0.54 (1:1 EtOAc-heptane).

CCC (S)-3-(1-carboxy-1-methyl-ethyl)-piperidine-1-carboxylic acid tert-butyl ester The title compound is prepared according to the procedure described for residue BBB starting from (S)-3-piperidine acetate hydrochloride (Arch Corp.).

DDD (R)-2-Methyl-2-(1-methyl-piperidin-3-yl)-propionic acid 0.489 g of (R)-2-methyl-2-(1-methyl-piperidin-3-yl)-propionic acid methyl ester are taken up in 4 ml of methanol and the mixture is admixed with 4 ml of 3M NaOH. The mixture is then stirred at 60° C. for 6 hours. The methanol is removed in vacuo and the aqueous residue acidified with 2M HCl to pH 7. The mixture is concentrated under reduced pressure. The residue is taken up in 10 ml of ethanol and the insoluble salts removed by filtration. Concentration of the filtrate under reduced pressure provides the title compound as a colourless solid which can be used without further purification.

The starting materials are prepared as follows:

a) (R)-2-Methyl-2-(1-methyl-piperidin-3-yl)-propionic acid methyl ester 0.992 g of 2-methyl-2-piperidin-3-yl-propionic acid methyl ester hydrochloride are dissolved in 2.2 ml of 2M NaOH. The solution is stirred for 10 minutes at room temperature. 7 ml of formic acid and 0.900 ml of 36% aqueous formaldehyde solution are added and the mixture is warmed to 60° C. for 16 hours. The solution is concentrated under reduced pressure. The residue is taken up water and the pH adjusted to 8-9 with saturated sodium carbonate solution. The mixture is extracted with ethyl acetate (3×) and tetrahydrofuran (2×)—the combined extracts are dried over sodium sulphate and concentrated. The title compound is obtained as a yellow oil from the residue by means of flash chromatography (SiO2 60F). Rf=0.23 (200:20:1 dichloromethane/methanol/25% conc. ammonia).

b) (R)-2-Methyl-2-piperidin-3-yl-propionic acid methyl ester hydrochloride 1.030 g of (R)-3-(1-methoxycarbonyl-1-methyl-ethyl)-piperidine-1-carboxylic acid tert-butyl ester are taken up in 10 ml of 4M HCl in dioxane. The reaction solution is left to stand at room temperature for 1 hour and is then concentrated under reduced pressure to provide the title compound as colourless solid which can be used without further purification.

EEE (S)-2-Methyl-2-(1-methyl-piperidin-3-yl)-propionic acid

The title compound is prepared according to the procedure described for residue DDD starting from (S)-3-(1-methoxycarbonyl-1-methyl-ethyl)-piperidine-1-carboxylic acid tert-butyl ester.

FFF trans-(4-Dimethylamino-cyclohexyl)-methyl-propionic acid

The title compound is prepared according to the procedure for residue BBB starting from trans-(4-dimethylamino-cyclohexyl)-acetic acid methyl ester [CAS 609805-50-7].

GGG cis-(4-Dimethylamino-cyclohexyl)-methyl-propionic acid 0.500 g of cis-(4-dimethylamino-cyclohexyl)-methyl-propionic acid methyl ester are taken up in 5 ml of methanol and the mixture is admixed with 5 ml of 3M NaOH. The mixture is then stirred at 60° C. for 16 hours. The methanol is removed in vacuo and the aqueous residue acidified with 2M HCl to pH 7. The mixture is concentrated under reduced pressure. The residue is taken up in 10 ml of ethanol and the insoluble salts removed by filtration. Concentration of the filtrate under reduced pressure provides the title compound which can be used without further purification.

The starting materials are prepared as follows:

a) cis-(4-Dimethylamino-cyclohexyl)-methyl-propionic acid methyl ester

A solution of 0.354 g of trans-2-methyl-2-[4-(toluene-4-sulfonyloxy)-cyclohexyl]-propionic acid methyl ester in 10 ml of 60% aqueous dimethylamine solution is heated to 110° C. for 48 hours. The reactions mixture is cooled to room temperature and extracted with dichloromethane (3×). The combined extracts are dried over sodium sulphate and concentrated. Flash chromatography (SiO2 60F) of the residue provides the title compound which is identified on the basis of its Rf-value.

b) trans-2-Methyl-2-[4-(toluene-4-sulfonyloxy)-cyclohexyl]-propionic acid methyl ester 0.400 g trans-2-(4-hydroxy-cyclohexyl)-2-methyl-propionic acid methyl ester (residue HH) are dissolved in 10 ml of dichloromethane. Triethylamine (0.42 ml) and 4-dimethylamino pyridine (0.012 g) are added and the solution is cooled to 0° C. 0.419 g of para-toluenesulfonyl chloride are added portionwise and the reaction mixture is then stirred at room temperature for 16 hours. The reaction mixture is poured onto saturated aqueous sodium hydrogencarbonate solution and the layers are separated. The aqueous layer is extracted with dichloromethane and the combined organics are dried over sodium sulphate and concentrated. Flash chromatography (SiO2 60F) of the residue provides the title compound which is identified on the basis of its Rf-value.

HHH (R)-2-(1-carboxy-1-methyl-ethyl)-piperidine-1-carboxylic acid tert-butyl ester The title compound is prepared according to the procedure described for residue BBB starting from (R)-2-methoxycarbonylmethyl-piperidine-1-carboxylic acid tert-butyl ester.

III (S)-2-(1-carboxy-1-methyl-ethyl)-piperidine-1-carboxylic acid tert-butyl ester [CAS813433-73-7].

The title compound is prepared according to the procedure described for residue BBB starting from (S)-2-methoxycarbonylmethyl-piperidine-1-carboxylic acid tert-butyl ester [CAS131134-77-5].

JJJ (R)-2-Methyl-2-(1-methyl-piperidin-2-yl)-propionic acid

The title compound is obtained according to the procedure described for residue DDD.

KKK (S)-2-Methyl-2-(1-methyl-piperidin-2-yl)-propionic acid

The title compound is obtained according to the procedure described for residue EEE.

MMM 2-Methyl-2-(1-methyl-1H-imidazol-4-yl)-propionic acid 1.96 g of 2-methyl-2-(1-methyl-1H-imidazol-4-yl)-propionic acid ethyl ester is taken up in 10 ml of methanol and the mixture is admixed with 10 ml of 3M NaOH. The mixture is then stirred at 60° C. for 16 hours. The methanol is removed in vacuo and the aqueous residue acidified with 2M HCl to pH 7. The mixture is concentrated under reduced pressure. The residue is taken up in 10 ml of ethanol and the insoluble salts removed by filtration. Concentration of the filtrate under reduced pressure provides the title compound which can be used without further purification.

The starting material is prepared as follows:

a) 2-Methyl-2-(1-methyl-1H-imidazol-4-yl)-propionic acid ethyl ester

A solution of 1.82 g of 2-(1H-imidazol-4-yl)-2-methyl-propionic acid ethyl ester [CAS 21149-99-5] in 20 ml of dry N,N-dimethylformamide is treated with 0.480 g sodium hydride (60% dispersion). The mixture is stirred for 30 minutes at 60° C. 0.81 ml of methyl iodide are added and the mixture stirred for 4 hours at 60° C. The reaction mixture is poured onto saturated aqueous sodium hydrogencarbonate solution and extracted with tert-butyl methyl ether (3×). The combined extracts are washed with brine, dried over sodium sulphate and concentrated by evaporation. Flash chromatography (SiO2 60F) of the residue provides the title compound which is identified on the basis of its Rf-value.

NNN 2-(1H-imidazol-2-yl)-2-methyl-propionic acid 3.334 g of 2-(1-benzyl-1H-imidazol-2-yl-2-methyl-propionic acid benzyl ester are hydrogenated at 440 psi in ethanol (50 ml) at 50° C. for 24 hours. The catalyst is removed by filtration over Hyflo and the filtrate is concentrated under reduced pressure to provide the title compound which can be used without further purification.

The starting material is prepared as follows:

a) 2-(1-Benzyl-1H-imidazol-2-yl-2-methyl-propionic acid benzyl ester

A solution of 3.06 g of (1-benzyl-1H-imidazol-2yl)-acetic acid benzyl ester [CAS 123566-36-9] in 20 ml N,N-dimethylformamide is treated with 0.960 g of sodium hydride (60% dispersion) at 0° C. The mixture is stirred at 0° C. for 30 minutes and 1.50 ml of methyl iodide are added. The reaction mixture is stirred for 1 hour at room temperature, then poured onto saturated aqueous sodium hydrogencarbonate solution and extracted with tert-butyl methyl ether (3×). The combined extracts are washed with brine, dried over sodium sulphate and concentrated by evaporation. Flash chromatography (SiO2 60F) of the residue provides the title compound which is identified on the basis of its Rf-value.

OOO 2-Methyl-2-(1-methyl-1H-imidazol-2-yl)-propionic acid

The title compound is obtained according to the procedure described for residue MMM starting from 2-methyl-2-(1-methyl-1H-imidazol-2-yl)-propionic acid ethyl ester.

The starting material is prepared as follows:

a) 2-Methyl-2-(1-methyl-1H-imidazol-2-yl)-propionic acid ethyl ester

The title compound is obtained according to the procedure described for residue NNNa starting from (1-methyl-1H-imidazol-2-yl)-acetic acid ethyl ester [CAS 130082-60-9].

PPP (R,S)-2-(1,4-Diaza-bicyclo[2.2.2]oct-2-yl)-2-methyl-propionic acid

The title compound is obtained according to the procedure described for residue BBB starting from (R,S)-(1,4-diaza-bicyclo[2.2.2]oct-2-yl)-acetic acid methyl ester [CAS 171351-26-1].

The Example Compounds 1A to 1QQQ correspond to the formula

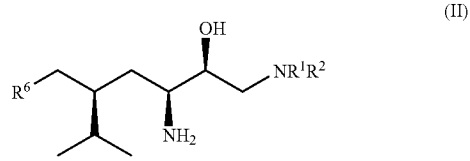

(II)

where $R^6$ corresponds to the above-specified residue 1 and $NR^1R^2$ in each case corresponds to one of the above-specified residues A to QQQ. The atoms denoted by * are the bonding sites. The further Example Compounds 2A to 41QQQ are accordingly the compounds of formula (II) in which the $NR^1R^2$ radical assumes all above residue-definitions (A to QQQ) for a given $R^6$ (above residue-definitions 2 to 41).

Thus, the Example Compound 3A is the compound 3-amino-1-isopropylamino-5-[3-(3-methoxypropyl)-1-methyl-1H-indol-5-ylmethyl]-6-methylheptan-2-ol. Analogously to the preparation process described herein below, the Example Compounds 1A to 41QQQ are obtained.

EXAMPLE 3A

3-Amino-1-isopropylamino-5-[3-(3-methoxypropyl)-1-methyl-1H-indol-5-ylmethyl]-6-methylheptan-2-ol dihydrochloride A solution of 0.030 g of tert-butyl {1-(1-hydroxy-2-isopropylaminoethyl)-3-[3-(3-methoxypropyl)-1-methyl-1H-indol-5-ylmethyl]-4-methylpentyl}carbamate in 1 ml of 4M HCl (in dioxane) is stirred at 0° C. to 20° C. over 2 hours, then concentrated by evaporation to dryness—the residue is dissolved in 1 ml of tert-butanol, frozen and lyophilized under high vacuum. The title compound is identified on the basis of the Rf value from the residue.

The starting materials are prepared as follows:

a) tert-butyl {1-(1-hydroxy-2-isopropylaminoethyl)-3-[3-(3-methoxypropyl)-1-methyl-1H-indol-5-ylmethyl]-4-methylpentyl}carbamate A solution of 0.032 g of tert-butyl {3-[3-(3-methoxypropyl)-1-methyl-1H-indol-5-ylmethyl]-4-methyl-1-oxiranylpentyl}carbamate in 1 ml of isopropanol and 0.044 ml of isopropylamine is stirred at 70° C. On completion of reaction (TLC monitoring), the reaction mixture is concentrated by evaporation, and the residue is admixed with water and extracted with tert-butyl methyl ether (2×). The combined organic phases are washed successively with water and brine, dried over sodium sulphate and concentrated by evaporation. The title compound is identified on the basis of the Rf value from the residue by means of flash chromatography (SiO2 60F).

b) tert-Butyl {3-[3-(3-methoxypropyl)-1-methyl-1H-indol-5-ylmethyl]-4-methyl-1-oxiranylpentyl}carbamate 1.29 g of trimethylsulphoxonium iodide and 0.66 g of potassium tert-butoxide are stirred under high vacuum overnight, admixed with 8 ml of tetrahydrofuran and subsequently cooled to 0° C. A solution of 1.01 g of tert-butyl {1-formyl-3-[3-(3-methoxypropyl)-1-methyl-1H-indol-5-ylmethyl]-4-methylpentyl}carbamate in 8 ml of dimethyl sulphoxide is added dropwise. On completion of reaction (TLC monitoring), the reaction mixture is partitioned between water and tert-butyl methyl ether, and the aqueous phase is extracted once more with tert-butyl methyl ether (2×). The combined organic phases are washed successively with water (3×) and brine, dried over sodium sulphate and concentrated by evaporation. The title compound is identified on the basis of the Rf value from the residue by means of flash chromatography (SiO2 60F).

c) tert-Butyl {1-formyl-3-[3-(3-methoxypropyl)-1-methyl-1H-indol-5-ylmethyl]-4-methylpentyl}carbamate 1.27 ml of triethylamine and then (over 20 minutes) a solution of 1.60 g of sulphur trioxide-pyridine complex in 6 ml of dimethyl sulphoxide are added dropwise at 0° C. to the solution of 1.44 g of tert-butyl {1-hydroxymethyl-3-[3-(3-methoxypropyl)-1-methyl-1H-indol-5-ylmethyl]-4-methylpentyl}carbamate in 10 ml of dichloromethane. After 40 minutes, 10 ml of ice-water are added dropwise and the reaction mixture is stirred at 10° C. for a further 10 minutes. The reaction mixture is extracted with dichloromethane (3×)—the combined organic phases are washed successively with 10% aqueous sodium hydrogensulphate solution, water, 10% sodium hydrogencarbonate solution and brine, dried over magnesium sulphate and concentrated by evaporation. The crude title compound is obtained as a yellowish foam from the residue. Rf=0.73 (2:1 EtOAc-heptane). Rt=5.48 (gradient I).

d) tert-Butyl {1-hydroxymethyl-3-[3-(3-methoxypropyl)-1-methyl-1H-indol-5-ylmethyl]-4-methylpentyl}carbamate A solution of 1.82 g of tert-butyl 4-{2-[3-(3-methoxypropyl)-1-methyl-1H-indol-5-ylmethyl]-3-methylbutyl}-2,2-dimethyloxazolidine-3-carboxylate in 30 ml of dichloromethane is admixed at room temperature with 0.070 g of p-toluenesulphonic acid monohydrate. After 1 hour, the reaction mixture is concentrated by evaporation—the title compound is obtained as a colourless oil from the residue by means of flash chromatography (SiO2 60F). Rf=0.50 (3:1 EtOAc-heptane). Rt=5.16 (gradient I).

e) tert-Butyl 4-{2-[3-(3-methoxypropyl)-1-methyl-1H-indol-5-ylmethyl]-3-methylbutyl}-2,2-dimethyloxazolidine-3-carboxylate A solution of 2.80 g of tert-butyl 4-(2-{(2-methoxyacetoxy)-[3-(3-methoxypropyl)-1-methyl-1H-indol-5-yl]-methyl}-3-methylbutyl)-2,2-dimethyloxazolidine-3-carboxylate (diastereomer mixture) in 140 ml of ethanol is hydrogenated at 0° C. in the presence of 0.294 ml of ethanolamine and 3.34 g of 10% Pd/C over 3.5 hours. The reaction mixture is clarified by filtration and the filtrate is concentrated by evaporation. The title compound is obtained as a colourless oil from the residue by means of flash chromatography (SiO2 60F). Rf=0.48 (1:1 EtOAc-heptane). Rt=29.41 (gradient II).

f) tert-Butyl 4-(2-{(2-methoxyacetoxy)-[3-(3-methoxypropyl)-1-methyl-1H-indol-5-yl]methyl}-3-methylbutyl)-2,2-dimethyloxazolidine-3-carboxylate (Diastereomer Mixture)

A solution of 2.48 g of tert-butyl 4-(2-{hydroxy-[3-(3-methoxypropyl)-1-methyl-1H-indol-5-yl]methyl}-3-methylbutyl)-2,2-dimethyloxazolidine-3-carboxylate (diastereomer mixture) in 70 ml of toluene is admixed at 0° C. successively with 1.04 ml of pyridine, 1.11 ml of methoxyacetyl chloride and 0.62 g of 4-dimethylaminopyridine. The reaction mixture is stirred at 0° C. over 3.5 hours. The resulting mixture is poured onto 0.1N HCl (cold) and extracted with tert-butyl methyl ether (2×). The combined organic phases are washed successively with water, 1M sodium hydrogencarbonate solution and brine, dried over sodium sulphate and filtered, and the filtrate is concentrated by evaporation. The title compound (diastereomer mixture) is obtained as a white foam from the residue by means of flash chromatography (SiO2 60F). Rf=0.32 (1:1 EtOAc-heptane). Rt=26.14 (gradient II).

g) tert-Butyl 4-(2-{hydroxy-[3-(3-methoxypropyl)-1-methyl-1H-indol-5-yl]-methyl}-3-methylbutyl)-2,2-dimethyloxazolidine-3-carboxylate (Diastereomer Mixture)

A solution of 12.51 ml of dibutylmagnesium (1M in heptane) in 70 ml of tetrahydrofuran is cooled to 0° C. and admixed with 7.80 ml of n-butyllithium (1M in hexane). After 10 minutes, the mixture is admixed with a solution of 3.60 g of 5-bromo-3-(3-methoxypropyl)-1-methyl-1H-indole (residue 3) and 0.14 ml of N-methylmorpholine in 15 ml of tetrahydrofuran and stirred at 0° C. for 30 minutes. The reaction mixture is cooled to −78° C. and admixed with the solution of 3.02 g of tert-butyl 4-(2-formyl-3-methylbutyl)-2,2-dimethyloxazolidine-3-carboxylate in 15 ml of tetrahydrofuran over 2 minutes. The resulting mixture is stirred at −78° C. for another 45 minutes and subsequently successively quenched with 1M ammonium chloride solution, diluted with water and extracted with tert-butyl methyl ether (3×). The combined organic phases are washed successively with 0.5N HCl (cold) (2×), water and brine, dried over sodium sulphate and filtered, and the filtrate is concentrated by evaporation. The title compound (diastereomer mixture) is obtained as a white foam from the residue by means of flash chromatography (SiO2 60F). Rf=0.21 (1:2 EtOAc-heptane). Rt=24.2/25.4 (gradient II).

h) tert-Butyl 4-(2-formyl-3-methylbutyl)-2,2-dimethyloxazolidine-3-carboxylate 6.97 ml of triethylamine are added dropwise at 0° C. to the solution of 3.0 g of tert-butyl 4-(2-hydroxymethyl-3-methylbutyl)-2,2-dimethyloxazolidine-3-carboxylate in 11 ml of dimethyl sulphoxide and 55 ml of dichloromethane. 5.23 g of sulphur trioxide-pyridine complex are added in 3 portions at intervals of 10 minutes and the reaction mixture is stirred at 0° C. for a further 3 hours. The reaction mixture is poured onto ice-water, adjusted to pH=2.5 with saturated aqueous potassium bisulphate solution and extracted with diethyl ether (3×)—the combined organic phases are washed successively with water and 5% aqueous sodium hydrogencarbonate solution, dried over sodium sulphate and concentrated by evaporation. The title compound is obtained from the residue as a yellow oil. Rf=0.46 (1:2 EtOAc-heptane).

i) tert-Butyl 4-(2-hydroxymethyl-3-methylbutyl)-2,2-dimethyloxazolidine-3-carboxylate A solution of 15.40 g of tert-butyl 4-(2-benzyloxymethyl-3-methylbutyl)-2,2-dimethyloxazolidine-3-carboxylate in 450 ml of tetrahydrofuran is hydrogenated at room temperature in the presence of 3.07 g of 10% Pd/C over 2 hours. The reaction mixture is clarified by filtration and the filtrate is concentrated by evaporation. The title compound is obtained as a yellowish oil from the residue by means of flash chromatography (SiO$_2$ 60F). Rf=0.28 (1:2 EtOAc-heptane). Rt=4.58 (gradient I).

j) tert-Butyl 4-(2-benzyloxymethyl-3-methylbutyl)-2,2-dimethyloxazolidine-3-carboxylate A solution of 14.70 g of tert-butyl (3-benzyloxymethyl-1-hydroxymethyl-4-methylpentyl)carbamate and 0.24 g of p-toluenesulphonic acid monohydrate in 82 ml of dichloromethane at 0° C. is admixed with 8.2 ml of 2-methoxypropene. After 22 hours at room temperature, the mixture is poured onto 1M aqueous sodium hydrogencarbonate solution and extracted with tert-butyl methyl ether (2×)—the combined organic phases are washed with brine, dried over sodium sulphate and concentrated by evaporation. The title compound is obtained as an orange oil from the residue by means of flash chromatography (SiO2 60F). Rt=6.30 (gradient I).

k) tert-Butyl (3-benzyloxymethyl-1-hydroxymethyl-4-methylpentyl)carbamate

A solution of 20.0 g of methyl 4-benzyloxymethyl-2-tert-butoxycarbonylamino-5-methylhexanoate [180182-92-7] in 320 ml of tetrahydrofuran at room temperature is admixed with 2.64 g of lithium borohydride in portions. After 4 hours, the reaction mixture is quenched with 200 ml of methanol dropwise over 1 hour and subsequently concentrated cautiously by evaporation. The residue is admixed once again with 150 ml of methanol and again concentrated by evaporation to dryness. The residue is admixed with 100 g of ice and 400 ml of 1N HCl and extracted with dichloromethane (3×)—the combined organic phases are washed with water, dried over sodium sulphate and concentrated by evaporation. The title compound is obtained as a beige oil from the residue by means of flash chromatography (SiO2 60F). Rf=0.32 (1:1 EtOAc-heptane). Rt=4.96 (gradient I).

EXAMPLE 35G

3-Amino-5-[8-(2-methoxyethoxy)naphthalen-2-ylmethyl]-6-methyl-1-piperidin-1-ylheptan-2-ol dihydrochloride Analogously to method A, 0.20 g of tert-butyl {1-(1-hydroxy-2-piperidin-1-ylethyl)-3-[8-(2-methoxyethoxy)naphthalen-2-ylmethyl]-4-methylpentyl}carbamate is used to prepare the title compound.

The starting materials are prepared as follows:

a) tert-Butyl {1-(1-hydroxy-2-piperidin-1-ylethyl)-3-[8-(2-methoxyethoxy)naphthalen-2-ylmethyl]-4-methylpentyl}carbamate A solution of 0.23 g of tert-butyl {3-[8-(2-methoxyethoxy)naphthalen-2-ylmethyl]-4-methyl-1-oxiranylpentyl}carbamate in 4 ml of isopropanol and 0.99 ml of piperidine is stirred at 70° C. On completion of reaction (TLC monitoring), the reaction mixture is concentrated by evaporation, and the residue is admixed with water and extracted with tert-butyl methyl ether (2×). The combined organic phases are washed successively with water and brine, dried over sodium sulphate and concentrated by evaporation. The title compound is identified on the basis of the Rf value from the residue by means of flash chromatography (SiO2 60F).

b) tert-Butyl {3-[8-(2-methoxyethoxy)naphthalen-2-ylmethyl]-4-methyl-1-oxiranylpentyl}carbamate 3.87 g of trimethylsulphoxonium iodide and 1.98 g of potassium tert-butoxide are stirred under high vacuum overnight, admixed with 24 ml of tetrahydrofuran and subsequently cooled to 0° C. A solution of 3.03 g of tert-butyl {1-formyl-3-[8-(2-methoxyethoxy)naphthalen-2-ylmethyl]-4-methylpentyl}carbamate in 24 ml of dimethyl sulphoxide is added dropwise. On completion of reaction (TLC monitoring), the reaction mixture is partitioned between water and tert-butyl methyl ether, and the aqueous phase is extracted once again with tert-butyl methyl ether (2×). The combined organic phases are washed successively with water (3×) and brine, dried over sodium sulphate and concentrated by evaporation. The title compound is identified on the basis of the Rf value from the residue by means of flash chromatography (SiO2 60F).

c) tert-Butyl {1-formyl-3-[8-(2-methoxyethoxy) naphthalen-2-ylmethyl]-4-methylpentyl}carbamate 1.04 ml of triethylamine and then a solution of 1.31 g of sulphur trioxide-pyridine complex are added at 0° C. to the solution of 0.86 g of tert-butyl {1-hydroxymethyl-3-[8-(2-methoxyethoxy)naphthalen-2-ylmethyl]-4-methylpentyl}carbamate in 8 ml of dichloromethane. After 45 minutes, the reaction mixture is admixed cautiously with ice-water. The resulting mixture is poured onto 1N HCl/ice and extracted with ethyl acetate (3×). The combined organic phases are washed successively with water (2×) and brine, clarified by filtration through Hyflo®, dried over sodium sulphate and concentrated by evaporation. In this way, the crude title compound is obtained.

d) tert-butyl {1-hydroxymethyl-3-[8-(2-methoxyethoxy)naphthalen-2-ylmethyl]-4-methylpentyl}carbamate A solution of 2.44 g of ethyl 2-tert-butoxycarbonylamino-4-[8-(2-methoxyethoxy)naphthalen-2-ylmethyl]-5-methylhexanoate in 35 ml of tetrahydrofuran is admixed at room temperature with 0.25 g of lithium borohydride in portions. After 23 hours, 35 ml of methanol are added dropwise and the resulting mixture is concentrated by evaporation at 40° C. The residue is once more admixed with 35 ml of methanol and again concentrated by evaporation to dryness. The residue is admixed with ice/1N HCl and extracted with dichloromethane (3×)—the combined organic phases are washed with water, dried over sodium sulphate and concentrated by evaporation. The title compound is identified on the basis of the Rf value from the residue by means of flash chromatography (SiO2 60F).

e) Ethyl 2-tert-butoxycarbonylamino-4-[8-(2-methoxyethoxy)naphthalen-2-ylmethyl]-5-methylhexanoate A solution of 1.94 g of ethyl 2-amino-4-[8-(2-methoxyethoxy)naphthalen-2-ylmethyl]-5-methylhexanoate in 16 ml of dichloromethane at 0° C. is admixed successively with 1.11 ml of ethyldiisopropylamine and a solution of 1.2 g of di-tert-butyl dicarbonate in 4 ml of dichloromethane. The reaction mixture is stirred at room temperature overnight and then concentrated by evaporation. The title compound is identified on the basis of the Rf value from the residue by means of flash chromatography (SiO2 60F).

f) Ethyl 2-amino-4-[8-(2-methoxyethoxy)naphthalen-2-ylmethyl]-5-methylhexanoate

A solution of 1.57 g of 3,6-diethoxy-2-{2-[8-(2-methoxyethoxy)naphthalen-2-ylmethyl]-3-methylbutyl}-2,5-dihydropyrazine in 14 ml of acetonitrile at room temperature is admixed with 14 ml of 1N HCl. After 30 minutes, the reaction mixture is poured into a stirred mixture of 15 ml of saturated aqueous sodium bicarbonate solution and 15 g of ice, and the mixture is extracted with dichloromethane (3×). The combined organic phases are washed with water (3×), dried with sodium sulphate and concentrated by evaporation. The crude title compound is identified on the basis of the Rf value from the residue.

g) 3,6-Diethoxy-2-{2-[8-(2-methoxyethoxy)naphthalen-2-ylmethyl]-3-methylbutyl}-2,5-dihydropyrazine 3.03 ml of n-butyllithium (1.6M in hexane) are added dropwise at −40° C. to the suspension of 0.884 g of 3,6-diethoxy-2,5-dihydropyrazine in 12 ml of tetrahydrofuran. After 20 minutes, a solution of 1.265 g of 7-(2-bromomethyl-3-methylbutyl)-1-(2-methoxyethoxy)naphthalene in 5 ml of tetrahydrofuran is added dropwise. The reaction mixture is stirred further at −40"C. for 30 minutes, then warmed to −20° C. over 1 hour. After 18 hours, the reaction mixture is concentrated by evaporation—the residue is partitioned between ethyl acetate and water. The aqueous phase is extracted with ethyl acetate (2×)—the combined organic phases are washed successively with water (2×) and brine, dried over sodium sulphate and concentrated by evaporation. The crude title compound is identified on the basis of the Rf value from the residue.

h) 7-(2-Bromomethyl3-methylbutyl)-1-(2-methoxyethoxy)naphthalene

A solution of 0.30 g of 2-[8-(2-methoxyethoxy)naphthalen-2-ylmethyl]-3-methylbutan-1-ol in 10 ml of dichloromethane at 0° C. is admixed with 0.29 g of triphenylphosphine and 0.20 g of N-bromosuccinimide. After 4 hours, the reaction mixture is concentrated by evaporation to a volume of approx. 3 ml, diluted with hexane, clarified by filtration and then concentrated fully by evaporation. The title compound is identified on the basis of the Rf value from the residue by means of flash chromatography (SiO2 60F).

i) 2-[8-(2-Methoxyethoxy)naphthalen-2-ylmethyl]-3-methylbutan-1-ol 3 ml of borane-tetrahydrofuran complex (1M in tetrahydrofuran) are added dropwise at 0° C. to the solution of 0.32 g of 2-[8-(2-methoxyethoxy)naphthalen-2-ylmethyl]-3-methylbutyric acid in 2 ml of tetrahydrofuran. After 2 hours at room temperature, the reaction mixture is cooled to 0° C., admixed cautiously with 5 ml of methanol and subsequently stirred at room temperature for 1 hour. The reaction mixture is concentrated by evaporation—the residue is dissolved once again in methanol and concentrated by evaporation to dryness. The title compound is identified on the basis of the Rf value from the residue by means of flash chromatography (SiO2 60F).

j) 2-[8-(2-Methoxyethoxy)naphthalen-2-ylmethyl]-3-methylbutyric acid 122 ml of hydrogen peroxide (30%) are added dropwise and then 0.17 g of lithium hydroxide monohydrate is added to the solution of 0.95 g of 4(R)-benzyl-3-{2-[8-(2-methoxyethoxy)naphthalen-2-ylmethyl]-3-methylbutyryl}oxazolidin-2-one in 12 ml of tetrahydrofuran and 4 ml of water at 0° C. After 6 hours at room temperature, the reaction mixture is cooled to 0° C. and admixed with a solution of 1.54 g of sodium sulphite in 9 ml of water (negative peroxide test). The reaction mixture is adjusted to pH 9.8 with saturated aqueous sodium hydrogen-carbonate solution and clarified by filtration, and the tetrahydrofuran is concentrated by evaporation. The residue is washed with dichloromethane (3×)—the combined organic phases are washed with phosphate buffer/25% conc. ammonia solution (pH 9.8). The combined aqueous phases are adjusted to pH 3.0 with 4N HCl and extracted with dichloromethane (2×). The combined organic phases are dried over sodium sulphate and concentrated by evaporation. The crude title compound is identified on the basis of the Rf value from the residue.

k) 4(R)-Benzyl-3-{2-[8-(2-methoxyethoxy)naphthalen-2-ylmethyl]-3-methylbutyryl}oxazolidin-2-one A solution of 0.31 g of 4(R)-benzyl-3-(3-methylbutyryl) oxazolidin-2-one in 2 ml of tetrahydrofuran is added dropwise at −78° C. to 1.2 ml of lithium bis(trimethylsilyl)amide solution (1M in tetrahydrofuran). After 30 minutes, a solution of 0.30 g of 7-bromomethyl-1-(2-methoxyethoxy)naphthalene in 2 ml of tetrahydrofuran is added dropwise and the reaction mixture is allowed to thaw from −78° C. to 0° C. over 2 hours. After 3 hours at 0° C., the reaction mixture is quenched with 5 ml of 1M ammonium chloride solution, diluted with water and extracted with tert-butyl methyl ether (2×). The combined organic phases are washed with brine, dried over sodium sulphate and concentrated by evaporation. The title compound is identified on the basis of the Rf value from the residue by means of flash chromatography (SiO2 60F).

l) 7-Bromomethyl-1-(2-methoxyethoxy)naphthalene 0.198 ml of bromotrimethylsilane are added dropwise at room temperature to a solution of 0.23 g of [8-(2-methoxyethoxy)naphthalen-2-yl]methanol in 5 ml of chloroform. After 1 hour, the reaction mixture is concentrated by evaporation. The title compound is identified on the basis of the Rf value from the residue by means of flash chromatography (SiO2 60F).

m) [8-(2-Methoxyethoxy)naphthalen-2-yl]methanol 1.64 ml of diisobutylaluminium hydride (1.5M in toluene) are added dropwise at 0° C. to a solution of 0.26 g of methyl 8-(2-methoxyethoxy)naphthalene-2-carboxylate (residue 35) in 20 ml of dichloromethane. After 3 hours, the reaction solution is admixed with 2 ml of ethyl acetate, stirred for 1 hour, then admixed with 3 ml of I M sodium potassium tartrate solution and subsequently stirred further for 1 hour. The reaction mixture is concentrated by evaporation—the residue is admixed with water and extracted with ethyl acetate (3×). The combined organic phases are washed successively with 1M HCl and brine, dried over sodium sulphate and concentrated by evaporation. The title compound is identified on the basis of the Rf value from the residue by means of flash chromatography (SiO2 60F).

EXAMPLE 3J

1-{3-Amino-2-hydroxy-5-[3-(3-methoxypropyl)-1-methyl-1H-indol-5-ylmethyl]-6-methylheptyl}piperidin-2-one hydrochloride A solution of 0.051 g of 1-(4-{2-[3-(3-methoxypropyl)-1-methyl-1H-indol-5-ylmethyl]-3-methylbutyl}-2-oxooxazolidin-5-ylmethyl)piperidin-2-one, 0.050 g of lithium hydroxide hydrate in 1.5 ml of ethanol and 1.5 ml of water is stirred at 100° C. over 2 hours. The reaction mixture is cooled to room temperature, poured onto ice-water and extracted with ethyl acetate (3×). The combined organic phases are dried over sodium sulphate and concentrated by evaporation. The title compound is obtained as a free base from the residue by means of flash chromatography (SiO2 60F). The latter is dissolved in 0.5 ml of dioxane, admixed with 20 µl of 4N HCl/dioxane, frozen in liquid nitrogen and lyophilized under high vacuum overnight. The title compound is identified on the basis of the Rf value from the residue.

The starting material is prepared as follows:

a) 1-(4-{2-[3-(3-Methoxypropyl)-1-methyl-1H-indol-5-ylmethyl]-3-methylbutyl}-2-oxooxazolidin-5-ylmethyl)piperidin-2-one A mixture of 0.115 g of piperidin-2-one, 0.136 g of potassium tert-butoxide in 3 ml of dimethyl sulphoxide is stirred at room temperature over 30 minutes, admixed with 0.26 g of tert-butyl {3-[3-(3-methoxypropyl)-1-methyl-1H-indol-5-ylmethyl]-4-methyl-1-oxiranylpentyl}carbamate (Example 3Ab) and subsequently stirred further at room temperature overnight. The reaction mixture is poured onto ice-water and extracted with tert-butyl methyl ether (2×). The combined organic phases are washed successively with water and brine, dried over sodium sulphate and concentrated by evaporation. The title compound is identified on the basis of the Rf value from the residue by means of flash chromatography (SiO2 60F).

EXAMPLE 3K

N-{3-Amino-2-hydroxy-5-[3-(3-methoxypropyl)-1-methyl-1H-indol-5-ylmethyl]-6-methylheptyl}-2,2-dimethylpropionamide hydrochloride A solution of 0.040 g of tert-butyl {1-[2-(2,2-dimethylpropionylamino)-1-hydroxyethyl]-3-[3-(3-methoxypropyl)-1-methyl-1H-indol-5-ylmethyl]-4-methylpentyl}carbamate in 1 ml of 4M HCl (in dioxane) is stirred at 0° C. to 20° C. over 2 hours, then concentrated by evaporation to dryness—the residue is dissolved in 1 ml of tert-butanol, frozen and lyophilized under high vacuum. The title compound is identified on the basis of the Rf value from the residue.

The starting materials are prepared as follows:

a) tert-Butyl {1-[2-(2,2-dimethylpropionylamino)-1-hydroxyethyl]-3-[3-(3-methoxypropyl)-1-methyl-1H-indol-5-ylmethyl]-4-methylpentyl}carbamate The stirred solution of 0.035 g of tert-butyl {1-(2-amino-1-hydroxyethyl)-3-[3-(3-methoxypropyl)-1-methyl-1H-indol-5-ylmethyl]-4-methylpentyl}carbamate in 0.60 ml of ethyl acetate is admixed successively with 0.60 ml of 2M sodium carbonate solution and 0.012 ml of pivaloyl chloride and stirred at room temperature over a further 1 hour. The reaction solution is admixed with water and extracted with ethyl acetate (2×). The combined organic phases are washed with water and brine, dried over sodium sulphate and concentrated by evaporation. The title compound is identified on the basis of the Rf value from the residue.

b) tert-Butyl {1-(2-amino-1-hydroxyethyl)-3-[3-(3-methoxypropyl)-1-methyl-1H-indol-5-ylmethyl]-4-methylpentyl}carbamate The solution of 0.51 g of tert-butyl {1-(2-azido-1-hydroxyethyl)-3-[3-(3-methoxypropyl)-1-methyl-1H-indol-5-ylmethyl]-4-methylpentyl}carbamate in 15 ml of methanol is hydrogenated in the presence of 0.11 g of 10% Pd/C over 1 hour. The reaction mixture is clarified by filtration and concentrated by evaporation. The title compound is identified on the basis of the Rf value from the residue.

c) tert-Butyl {1-(2-azido-1-hydroxyethyl)-3-[3-(3-methoxypropyl)-1-methyl-1H-indol-5-ylmethyl]-4-methylpentyl}carbamate The solution of 0.59 g of tert-butyl {3-[3-(3-methoxypropyl)-1-methyl-1H-indol-5-ylmethyl]-4-methyl-1-oxiranylpentyl}carbamate (Example 3Ab) in 12 ml of methanol is admixed with 0.21 g of sodium azide and 0.12 g of ammonium chloride and stirred at reflux over 6 hours. The reaction mixture is cooled, poured onto ice-water and extracted with tert-butyl methyl ether (2×). The combined organic phases are washed with water and brine, dried over sodium sulphate and concentrated by evaporation. The title compound is identified on the basis of the Rf value from the residue.

EXAMPLE 3WW

N-{3-Amino-2-hydroxy-5-[3-(3-methoxypropyl)-1-methyl-1H-indol-5-ylmethyl]-6-methylheptyl}propane-2-sulphonamide hydrochloride 0.007 ml of propane-2-sulphonyl chloride is added to a solution of 0.026 g of tert-butyl {1-(2-amino-1-hydroxyethyl)-3-[3-(3-methoxypropyl)-1-methyl-1H-indol-5-ylmethyl]-4-methylpentyl}carbamate (Example 3Kb), and 0.007 ml of triethylamine in 1 ml of dichloromethane is added at 0° C. After 6 hours, the reaction mixture is concentrated by evaporation—the N-Boc intermediate is identified on the basis of the Rf value from the residue by means of flash chromatography (SiO2 60F). The N-Boc intermediate is dissolved in 0.82 ml of 4N HCl/dioxane—after 4 hours, the reaction mixture is concentrated by evaporation, and the residue is dissolved in 0.5 ml of tert-butanol, frozen in liquid nitrogen and lyophilized under high vacuum overnight. The title compound is identified on the basis of the Rf value from the residue.

The invention claimed is:
1. A compound of the formula

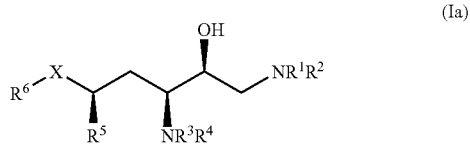

(Ia)

where

X is methylene or hydroxymethylene;

$R^1$ a) is hydrogen; or b) is $C_1$-$C_8$-alkyl, $C_3$-$C_8$-cycloalkyl, $C_1$-$C_8$-alkanoyl, $C_1$-$C_8$-alkoxycarbonyl, or heterocyclyl-$C_0$-$C_4$-alkyl, which radicals may be substituted by 1-4 $C_1$-$C_8$-alkyl, halogen, cyano, oxide, oxo, trifluoromethyl, $C_1$-$C_8$-alkoxy, $C_1$-$C_8$alkoxycarbonyl, aryl or heterocyclyl;

$R^2$ a) is $C_1$-$C_8$-alkyl, $C_3$-$C_8$-cycloalkyl, $C_1$-$C_8$-alkylsulphonyl, $C_3$-$C_8$-cycloalkylsulphonyl, aryl -$C_0$-$C_8$-alkylsulphonyl, heterocyclylsulphonyl, $C_3$-$C_{12}$-cycloalkyl-$C_1$-$C_8$-alkanoyl, $C_3$-$C_{12}$-cycloalkyl-$C_3$-$C_8$-cycloalkanoyl, aryl-$C_1$-$C_8$alkanoyl, heterocyclyl-$C_1$-$C_8$alkanoyl, aryl-$C_3$-$C_8$-cycloalkanoyl, $C_1$-$C_8$-alkanoyl, $C_1$-$C_8$-alkoxycarbonyl, optionally N-mono or N,N-di-$C_1$-$C_8$-alkylated carbamoyl-$C_0$-$C_8$-alkyl, or heterocyclyl-$C_0$-$C_4$-alkyl, which radicals may be substituted by 1-4 $C_1$-$C_8$-alkyl, $C_3$-$C_8$-cycloalkyl, $C_3$-$C_8$-cycloalkoxy, amino, $C_{1-6}$-alkylamino, di-$C_{1-6}$-alkylamino, $C_0$-$C_6$-alkylcarbonylamino, halogen, cyano, hydroxyl, oxide, oxo, trifluoromethyl, $C_1$-$C_8$-alkoxy, optionally N-mono or N,N-di-$C_1$-$C_8$alkylated carbamoyl, $C_1$-$C_8$alkoxycarbonyl, $C_{1-6}$-alkylenedioxy, aryl or heterocyclyl; or b) together with $R_1$ and the nitrogen atom to which they are bonded, is a saturated or partly unsaturated 4-8-membered heterocyclic ring which may contain an additional nitrogen, oxygen or sulphur atom or an —SO- or —SO2-group, and the additional nitrogen atom may optionally be substituted by $C_1$-$C_8$-alkyl, $C_1$-$C_8$-alkanoyl, $C_1$-$C_8$-alkoxycarbonyl, aryl or heterocyclyl radicals, in which case this heterocyclic ring may be part of a bicyclic or tricyclic ring system having a total of up to 16 members and the second ring may also contain a nitrogen, oxygen or sulphur atom or an —SO- or —SO2-group, and the nitrogen atom of the second ring may optionally be substituted by $C_1$-$C_8$-alkyl, $C_1$-$C_8$-alkanoyl, $C_1$-$C_8$-alkoxycarbonyl, aryl or heterocyclyl radicals, and all ring systems mentioned may be substituted by 1-4 $C_1$-$C_8$-alkyl, halogen, hydroxyl, oxide, oxo, trifluoromethyl, $C_1$-$C_8$-alkoxy, $C_1$-$C_8$-alkoxy-$C_1$-$C_8$-alkyl, $C_1$-$C_8$-alkoxy-$C_1$-$C_8$-alkoxy, $C_1$-$C_8$-alkoxycarbonylamino, $C_1$-$C_8$-alkylcarbonylamino, $C_1$-$C_8$-alkylamino, N,N-di-$C_1$-$C_8$-alkylamino, aryl-$C_0$-$C_4$-alkyl, aryloxy -$C_0$-$C_4$-alkyl, aryl-$C_0$-$C_4$-alkyl-$C_1$-$C_8$-alkoxy, aryloxy-$C_0$-$C_4$-alkyl-$C_1$-$C_8$-alkoxy, heterocyclyl-$C_0$-$C_4$-alkyl, heterocyclyloxy-$C_0$-$C_4$-alkyl, heterocyclyl-$C_0$-$C_4$-alkyl-$C_1$-$C_8$-alkoxy or heterocyclyloxy-$C_0$-$C_4$-alkyl-$C_1$-$C_8$-alkoxy;

$R^3$ is hydrogen, $C_1$-$C_4$-alkyl, $C_1$-$C_8$-alkoxycarbonyl or $C_1$-$C_8$-alkanoyl;

$R^4$ is hydrogen, $C_1$-$C_4$-alkyl, $C_1$-$C_8$-alkoxycarbonyl or $C_1$-$C_8$-alkanoyl;

$R^5$ is hydrogen, or $C_1$-$C_8$-alkyl;

(A) $R^6$ is a heterocyclyl radical which is substituted by from one to four radicals selected from $C_1$-$C_6$-alkyl, $C_{3-8}$-cycloalkyl, $C_{3-8}$-cycloalkoxy, $C_{3-8}$cycloalkoxy-$C_{1-6}$alkyl, $C_{3-8}$-cycloalkoxy, -$C_{1-6}$alkoxy, $C_{1-6}$-alkylamino, di-$C_1$-$C_6$-alkylamino, amino-$C_{1-6}$-alkyl, amino-$C_{2-7}$-alkoxy, polyhalo-$C_{1-6}$-alkyl, polyhalo-$C_{2-7}$-alkoxy, nitro, amino, $C_2$-$C_6$-alkenyl, $C_1$-$C_6$-alkoxy, $C_1$-$C_6$-alkanoyloxy, hydroxyl, halogen, oxide, oxo, cyano, carbamoyl, carboxy, $C_1$-$C_6$-alkylenedioxy, phenyl, phenoxy, phenylthio, phenyl-$C_1$-$C_6$-alkyl or phenyl-$C_1$-$C_6$-alkoxy, each of which are optionally substituted by halogen, $C_1$-$C_6$-alkyl, $C_{1-6}$-alkoxy, hydroxyl, $C_1$-$C_6$-alkylamino, di-$C_1$-$C_6$-alkylamino, $C_{1-6}$-alkoxycarbonyl, hydroxy-$C_{1-6}$-alkyl or trifluoromethyl, pyridylcarbonylamino-$C_{1-6}$-alkyl, $C_{2-7}$-alkenyloxy, $C_{1-6}$alkoxy- $C_{1-6}$-alkoxy, $C_{1-6}$-alkoxy-$C_{1-6}$-alkoxy-$C_{1-6}$-alkyl, methoxybenzyloxy, hydroxybenzyloxy, methylenedioxybenzyloxy, dioxolanyl-$C_{1-6}$-alkoxy, $C_{3-8}$-cycloalkyl-$C_{1-6}$alkyl, $C_{3-8}$-cycloalkyl-$C_{1-6}$-alkoxy, hydroxy-$C_{2-7}$-alkoxy, carbamoyloxy-$C_{2-7}$-alkoxy, pyridylcarbamoyloxy-$C_{2-7}$-alkoxy, benzoyloxy-$C_{2-7}$-alkoxy, $C_{1-6}$-alkoxycarbonyl, $C_{1-6}$-alkylcarbonylamino, $C_{1-6}$-alkylcarbonylamino-$C_{1-6}$-alkyl, $C_{1-6}$-alkylcarbonylamino-$C_{2-7}$-alkoxy, (N-$C_{1-6}$-alkyl)-$C_{1-6}$-alkylcarbonylamino-$C_{1-6}$-alkyl, (N-$C_{1-6}$-alkyl)-$C_{1-6}$-alkylcarbonylamino-$C_{2-7}$-alkoxy, $C_{3-8}$- cycloalkylcarbonylamino-$C_{1-6}$-alkyl, $C_{3-8}$-cycloalkylcarbonylamino-$C_{2-7}$-alkoxy, $C_{1-6}$alkoxy, $C_{1-6}$alkyl, hydroxy-$C_{1-6}$-alkyl, hydroxy-$C_{2-7}$-alkoxy-$C_{1-6}$-alkyl, hydroxy-$C_{2-7}$-alkoxy-$C_{1-6}$-alkoxy, $C_{1-6}$-alkoxycarbonyl -amino-$C_{1-6}$-alkyl, $C_{1-6}$-alkoxycarbonylamino-$C_{2-7}$-alkoxy, $C_{1-6}$-alkylaminocarbonyl- amino-$C_{1-6}$-alkyl, $C_{1-6}$-alkylaminocarbonylamino-$C_{2-7}$-alkoxy, $C_{1-6}$-alkylaminocarbonyl-$C_{1-6}$-alkyl, $C_{1-6}$-alkylaminocarbonyl-$C_{1-6}$-alkoxy, $C_{1-6}$-alkylaminocarbonyl-$C_{1-6}$-alkoxy-$C_{1-6}$-alkyl, di-$C_{1-6}$-alkylaminocarbonyl-$C_{1-6}$-alkyl, di-$C_{1-6}$-alkylaminocarbonyl-$C_{1-6}$-alkoxy, $C_{1-6}$-alkylcarbonyloxy-$C_{1-6}$-alkyl, $C_{1-6}$-alkylcarbonyloxy-$C_{2-6}$-alkoxy, cyano-$C_{1-6}$-alkyl, cyano-$C_{1-6}$-alkoxy, 2-oxooxazolidinyl-$C_{1-6}$-alkyl, 2-oxo-oxazolidinyl-$C_{1-6}$-alkoxy, $C_{1-6}$-alkoxycarbonyl-$C_{1-6}$-alkyl, $C_{1-6}$-alkoxycarbonyl-$C_{1-6}$-alkoxy, $C_{1-6}$-alkylsulphonylamino-$C_{1-6}$-alkyl, $C_{1-6}$-alkylsulphonylamino-$C_{2-7}$-alkoxy, (N-$C_{1-6}$-alkyl)-$C_{1-6}$ alkylsulphonylamino -$C_{1-6}$alkyl, (N-$C_{1-6}$alkyl)-$C_{1-6}$-alkylsulphonylamino-$C_{2-7}$alkoxy, $C_{1-6}$alkylamino-$C_{1-6}$-alkyl, $C_{1-6}$-alkylamino-$C_{2-7}$-alkoxy, di-$C_{1-6}$alkylamino-$C_{1-6}$alkyl, di-$C_{1-6}$-alkylamino-$C_{2-7}$-alkoxy, $C_{1-6}$-alkylsulphonyl-$C_{1-6}$-alkyl, $C_{1-6}$-alkylsulphonyl-$C_{1-6}$-alkoxy, carboxy-$C_{1-6}$-alkyl, carboxy-$C_{1-6}$-alkoxy, carboxy-$C_{1-6}$-alkoxy-$C_{1-6}$-alkyl, $C_{1-6}$-alkoxy-$C_{1-6}$-alkylcarbonyl, acyl-$C_{1-6}$-alkoxy-$C_{1-6}$-alkyl, (N-$C_{1-6}$-alkyl)-$C_{1-6}$-alkoxycarbonylamino, (N-hydroxy)-$C_{1-6}$-alkylaminocarbonyl-$C_{1-6}$-alkyl, (N-hydroxy)-$C_{1-6}$ alkylaminocarbonyl -$C_{1-6}$-alkoxy, (N-hydroxy)aminocarbonyl-$C_{1-6}$-alkyl, (N-hydroxy)aminocarbonyl-$C_{1-6}$-alkoxy, $C_{1-6}$-alkoxy-aminocarbonyl-$C_{1-6}$-alkyl, 6-alkoxyaminocarbonyl-$C_{1-6}$-alkoxy, (N-$C_{1-6}$-alkoxy)-$C_{1-6}$-alkylaminocarbonyl-$C_{1-6}$-alkyl, (N-$C_{1-6}$-alkoxy)-$C_{1-6}$alkylamino -carbonyl-$C_{1-6}$-alkoxy, (N-acyl)-$C_{1-6}$-alkoxy-$C_{1-6}$-alkylamino, $C_{1-6}$-alkoxy-$C_{1-6}$-alkylcarbamoyl, (N-$C_{1-6}$-alkoxy)-$C_{1-6}$-alkoxy-$C_{1-6}$$C_{1-6}$ alkylcarbamoyl, -$C_{1-6}$alkoxy-$C_{1-6}$-alkylcarbonyl, $C_{1-6}$-alkoxy-$C_{1-6}$-alkylcarbonylamino, (N-$C_{1-6}$-alkyl)-$C_{1-6}$-alkoxy-$C_{1-6}$alkylcarbonylamino, 1-$C_{1-6}$-alkoxy-$C_{1-6}$ alkylimidazol-2yl, 1alkoxy-$C_{1-6}$-alkyltetrazol-5-yl, 5-$C_{1-6}$-alkoxy-$C_{1-6}$-alkyltetrazol-1-yl, 2$C_{1-6}$alkoxy-$C_{1-6}$alkyl-4oxoimidazol-1-yl, carbamoyl-$C_{1-6}$-alkyl, carbamoyl-$C_{1-6}$-alkoxy, $C_{1-6}$-alkylcarbamoyl, di-$C_{1-6}$-alkylcarbamoyl, $C_{1-6}$-alkylsulphonyl, $C_{1-6}$-alkylamidinyl, acetamidinyl-$C_{1-6}$-alkyl, O-methyloximyl-$C_{1-6}$-alkyl, O,N-dimethylhydroxylamino-$C_{1-6}$-alkyl, $C_{3-6}$-cycloalkyl-$C_{1-6}$-alkanoyl, aryl-$C_{1-6}$-alkanoyl or heterocyclyl-$C_{1-6}$-alkanoyl, or else pyridyl, pyridyloxy, pyridylthio, pyridylamino, pyridyl-$C_{1-6}$-alkoxy, pyrimidinyl, pyrimidinyloxy, pyrimidinylthio, pyrimidinylamino, pyrimidinyl-$C_{1-6}$-alkyl, pyrimidinyl -$C_{1-6}$-alkoxy, thienyl, thienyl-$C_{1-6}$-alkyl, thienyl-$C_{1-6}$-alkoxy, furyl, furyl-$C_{1-6}$-alkyl or furyl -$C_{1-6}$-alkoxy, each of which is optionally substituted by halogen, $C_{1-6}$-alkyl, $C_{1-6}$-alkoxy or dihydroxy-$C_{1-6}$-alkylaminocarbonyl, piperidinoalkyl, piperidinoalkoxy, piperidinoalkoxyalkyl, morpholinoalkyl, morpholinoalkoxy, morpholinoalkoxyalkyl, piperazinoalkyl, piperazinoalkoxy, piperazinoalkoxyalkyl,[1,2,4]-triazol-1-ylalkyl, [1,2,4]-triazol-1-ylalkoxy,[1,2,4]-triazol-4-ylalkyl,[1,2,4]-triazol-4-ylalkoxy,[1,2,4]-oxadiazol-5-ylalkyl,[1,2,4]-oxadiazol-5-ylalkoxy, 3-methyl-[1,2,4]-oxadiazol-5-ylalkyl, 3-methyl-[1,2,4]-oxadiazol-5-ylalkoxy, 5-methyl-[1,2,4]-oxadiazol-3-ylalkyl, 5methyl [1,2,4]-oxadiazol-3-ylalkoxy, tetrazol-1-ylalkyl, tetrazol-1-ylalkoxy, tetrazol-2-ylalkyl, tetrazol-2-ylalkoxy, tetrazol-5-ylalkyl, tetrazol-5-ylalkoxy, 5-methyl-tetrazol-1-ylalkyl, 5-methyl-tetrazol-l-ylalkoxy, thiazol-4-ylalkyl, thiazol-4-ylalkoxy, oxazol-4-ylalkyl, oxazol -4-ylalkoxy, 2-oxo-pyrrolidinylalkyl, 2-oxo-pyrrolidinylalkoxy, imidazolylalkyl, imidazolylalkoxy, 2-methyl-imidazolylalkyl, 2-methyl-imidazolylalkoxy, N-methyl -piperazinoalkyl, N-methylpiperazinoalkoxy, N-methylpiperazinoalkoxyalkyl, dioxolanyl, dioxanyl, dithiolanyl, dithianyl, pyrrolidinyl, piperidinyl, piperazinyl, pyrrolyl, 4methyl -piperazinyl, morpholinyl, thiomorpholinyl, 2-hydroxymethylpyrrolidinyl, 3hydroxy -pyrrolidinyl, 3,4-dihydroxypyrrolidinyl, 3-acetamidomethylpyrrolidinyl, 3-$C_{1-6}$alkoxy -$C_{1-6}$-alkyl-pyrrolidinyl, 4-hydroxypiperidinyl, 4-oxopiperidinyl, 3,5-dimethylmorpholinyl, 4,4-dioxothiomorpholinyl, 4-oxothiomorpholinyl, 2,6-dimethylmorpholinyl, 2-oxo -imidazolidinyl, 2-oxooxazolidinyl, 2-oxopyrrolidinyl, 2oxo -[1,3] oxazinyl, 2oxo -tetrahydropyrimidinyl and the —O—CH$_2$CH(OH)CH$_2$NR$_x$ radical where NR$_x$ is a mono- or di-$C_{1-6}$-alkylamino, piperidino, morpholino, piperazino or N-methylpiperazino radical; or (B) R$^6$ is phenyl substituted by $C_1$-$C_6$-alkylenedioxy, furyl, thienyl, pyridyl, pyrimidyl, indolyl, quinolinyl, pyrazinyl, triazolyl, imidazolyl, benzothiazolyl, pyranyl, tetrahydropyranyl, azetidinyl, morpholinyl, tetrahydroquinolyl, tetrahydroisoquinolyl, quinazolinyl, quinoxalinyl, isoquinolyl, benzo[b]thienyl, isobenzofuranyl, benzoimidazolyl, 2- oxobenzoimidazolyl, oxazolyl, thiazolyl, pyrrolyl, pyrazolyl, triazinyl, dihydrobenzofuranyl, 2-oxodihydrobenzo[d][1,3]oxazinyl, 4-oxodihydroimidazolyl, 5-oxo-4H[1,2,4]triazinyl, 3-oxo-4H-benzo [1,4]thiazinyl, tetrahydroquinoxalinyl, 1,1,3-trioxodihydro-2H-1λ$^6$-benzo[1,4]thiazinyl, 1-oxopyridyl, dihydro-3H -benzo[1,4]oxazinyl, 3,4-dihydro-2H-benzo[1,4]oxazinyl, 2-oxotetrahydrobenzo[e][1,4]diazepinyl, 2-oxodihydrobenzo[e][1,4]diazepinyl, 1H -pyrrolizinyl, phthalazinyl, 1-oxo-3H-isobenzofuranyl, 4-oxo-3H-thieno[2,3-d]pyrimidinyl, 3-oxo-4H-benzo[1,4]oxazinyl, [1,5]naphthyridyl, dihydro-2H-benzo [1,4]thiazinyl, 1,1-dioxodihydro-2H-benzo[1,4] thiazinyl, 2-oxo-1H-pyrido[2,3-b][1,4]oxazinyl, dihydro-1H-pyrido[2,3-b][1,4]oxazinyl, 1H-pyrrolo[2,3-b]pyridyl, benzo [1,3]dioxolyl, benzooxazolyl, 2-oxobenzooxazolyl, 2-oxo-1,3-dihydroindolyl, 2,3-dihydroindolyl, indazolyl, benzofuranyl, dioxolanyl, dioxanyl, dithiolanyl, dithianyl, pyrrolidinyl, piperidinyl, piperazinyl, 4-methylpiperazinyl, morpholinyl, thiomorpholinyl, 2-hydroxymethylpyrrolidinyl, 3-hydroxypyrrolidinyl, 3,4-dihydroxypyrrolidinyl, 4-hydroxypiperidinyl, 4-oxopiperidinyl, 3,5-dimethylmorpholinyl, 4,4dioxothio -morpholinyl, 4-oxothiomorpholinyl, 2,6-dimethylmorpholinyl, tetrahydropyranyl, 2-oxoimidazolidinyl, 2-oxooxazolidinyl, 2-oxopiperidinyl, 2-oxopyrrolidinyl, 2-oxo[1,3]oxazinyl, 2-oxoazepanyl, or 2-oxotetrahydropyrimidinyl;

or a prodrug thereof, or a salt thereof.

2. The compound according to claim 1, in which R$^2$ is $C_1$-$C_8$-alkyl, $C_3$-$C_8$-cycloalkyl, $C_1$-$C_8$-alkylsulphonyl, $C_3$-$C_8$-cycloalkylsulphonyl, aryl-$C_0$-$C_8$-alkylsulphonyl, $C_3$-$C_{12}$-cycloalkyl-$C_1$-$C_8$-alkanoyl, $C_3$-$C_{12}$-cycloalkyl-$C_3$-$C_8$-cycloalkanoyl, aryl-$C_1$-$C_8$-alkanoyl, heterocyclyl-$C_1$-$C_8$-alkanoyl, or $C_1$-$C_8$alkanoyl, which radicals may be substituted by 1-4 $C_1$-$C_8$-alkyl, $C_3$-$C_8$-cycloalkyl, $C_3$-$C_8$-cycloalkoxy, $C_0$-$C_6$-alkylcarbonylamino, halogen, cyano, hydroxyl, oxide, trifluoromethyl, $C_1$-$C_8$-alkoxy or optionally N-mono- or N,N- di-$C_1$-$C_8$-alkylated carbamoyl.

3. The compound according to claim 1, in which $R^1$ a) is hydrogen; or b) is $C_1$-$C_8$-alkyl or $C_3$-$C_8$-cycloalkyl;

$R^2$ a) is $C_1$-$C_8$-alkyl, $C_3$-$C_8$-cycloalkyl, $C_1$-$C_8$-alkanoyl, heterocyclyl-$C_1$-$C_8$-alkanoyl, $C_3$-$C_{12}$-cycloalkyl-$C_1$-$C_8$-alkanoyl or aryl-$C_1$-$C_8$-alkanoyl, which radicals may be substituted by 1-4 $C_1$-$C_8$-alkyl, $C_{1-6}$-alkylamino, cyano, halogen, hydroxyl, $C_1$-$C_6$-alkanoylamino, $C_1$-$C_8$-alkoxy, oxide, oxo, trifluoromethyl or aryl; or b) together with $R^1$ and the nitrogen atom to which they are bonded, is a saturated or partly unsaturated, 4-8-membered heterocyclic ring which may contain an additional nitrogen or oxygen atom, in which case the additional nitrogen atom may optionally be substituted by $C_1$-$C_8$-alkyl or $C_1$-$C_8$-alkanoyl, in which case this heterocyclic ring may be part of a bicyclic or tricyclic ring system having a total of up to 16 ring members and the second ring may also contain a nitrogen or oxygen atom, and the nitrogen atom of the second ring may optionally be substituted by $C_1$-$C_8$-alkyl or $C_1$-$C_8$-alkanoyl, and all ring systems mentioned may be substituted by 1-4 $C_1$-$C_8$-alkyl, hydroxyl, oxide, oxo, $C_1$-$C_8$alkoxy, $C_1$-$C_8$-alkoxy-$C_1$-$C_8$alkoxy, $C_1$-$C_8$-alkanoylamino or aryloxy-$C_0$-$C_4$-alkyl-$C_1$-$C_8$-alkoxy.

4. The compound according to claim 1, in which X is methylene;

$R^1$ a) is hydrogen; or b) is $C_1$-$C_8$-alkyl or $C_3$-$C_8$-cycloalkyl;

$R^2$ a) is $C_1$-$C_8$-alkyl, $C_3$-$C_8$-cycloalkyl, $C_1$-$C_8$-alkanoyl, heterocyclyl-$C_1$-$C_8$-alkanoyl, $C_3$-$C_{12}$-cycloalkyl-$C_1$-$C_8$alkanoyl or aryl-$C_1$-$C_8$-alkanoyl, which radicals may be substituted by 1-4 $C_1$-$C_8$-alkyl, $C_1$-$C_6$-alkylamino, cyano, halogen, hydroxyl, $C_1$-$C_6$-alkanoylamino, $C_1$-$C_8$-alkoxy, oxide, oxo, trifluoromethyl or aryl; or b) together with $R^1$ and the nitrogen atom to which they are bonded, is a saturated or partly unsaturated, 4-8-membered heterocyclic ring which may contain an additional nitrogen or oxygen atom, in which case the additional nitrogen atom may optionally be substituted by $C_1$-$C_8$-alkyl or $C_1$-$C_8$-alkanoyl, in which case this heterocyclic ring may be part of a bicyclic or tricyclic ring system having a total of up to 16 ring members and the second ring may also contain a nitrogen or oxygen atom, and the nitrogen atom of the second ring may optionally be substituted by $C_1$-$C_8$-alkyl or $C_1$-$C_8$-alkanoyl, and all ring systems mentioned may be substituted by 1-4 $C_1$-$C_8$-alkyl, hydroxyl, oxide, oxo, $C_1$-$C_8$-alkoxy, $C_1$-$C_8$-alkoxy-$C_1$-$C_8$-alkoxy, $C_1$-$C_8$-alkanoylamino or aryloxy-$C_0$-$C_4$-alkyl-$C_1$-$C_8$-alkoxy;

$R^3$ is hydrogen;

$R^4$ is hydrogen;

$R^5$ is hydrogen or $C_1$-$C_8$-alkyl; and $R^6$ is as defined in claim 1.

5. The compound according to claim 1, in which the $R^6$ radical is selected from the group consisting of furyl, thienyl, pyridyl, pyrimidyl, indolyl, quinolinyl, benzoimidazolyl, di-$C_{1-6}$-alkoxypyrimidinyl, 2- and 5-benzo[b]thienyl, 6- and 7-isoquinolyl, 6-and 7-tetrahydroquinolyl, 6- and 7-tetrahydroisoquinolyl, 6-quinoxalinyl, 6- and 7-quinazolinyl, dihydro-3H-benzo[1,4]oxazinyl, 3,4-dihydro-2H-benzo[1,4]oxazinyl, 3-oxo-4H-benzo[1,4]oxazinyl, 2-oxobenzooxazolyl, 2-oxo-1,3-dihydroindolyl, 2,3-dihydroindolyl, indazolyl or benzofuranyl; and 6- and 7-quinolyl, 6- and 7-isoquinolyl, 6- and 7-tetrahydroquinolyl, oxotetrahydroquinolyl, 6-and 7-tetrahydroisoquinolyl, 6-quinoxalinyl, 6- and 7-quinazolinyl, indolyl, dihydro-3H-benzo[1,4]oxazinyl, 3,4-dihydro-2H-benzo[1,4]oxazinyl, 3-oxo-3,4-dihydro-2H-benzo[1,4]oxazinyl, 3-oxo-4H-benzo[1,4]oxazinyl, 2-oxobenzooxazolyl, 2-oxo-2,3-dihydrobenzooxazolyl, 2-oxo-1,3-dihydroindolyl, 2,3-dihydroindolyl, indazolyl, benzofuranyl, 2,3-dihydrobenzothiazinyl, imidazolyl, benzoimidazolyl, pyridinyl, pyrrolo[2,3-b]pyridinyl, pyrrolo[3,2-c]pyridinyl, pyrrolo[2,3-c]pyridinyl, pyrrolo[3,2-b]pyridinyl, [1,2,3]triazolo[1,5-a]pyridinyl, [1,2,4]triazolo[4,3-a]pyridinyl, imidazo[1,2-a]pyrimidinyl, imidazo[1,5-a]pyridinyl or naphthyl or cyclohexenophenyl, each of which is substituted by from one to four radicals selected from $C_{1-6}$-alkyl, cyano, oxo, oxide, trifluoromethyl, hydroxyl, halogen, carbamoyl, carboxy, $C_{1-6}$-alkoxy, hydroxy-$C_{2-7}$-alkoxy, $C_{1-6}$-alkoxy-$C_{1-6}$-alkoxy, di-$C_{1-6}$-alkylamino, 2,3-dihydroxypropoxy, 2,3-dihydroxypropoxy-$C_{1-6}$-alkoxy, 2,3-dimethoxypropoxy, methoxybenzyloxy, hydroxybenzyloxy, phenethyloxy, methylenedioxybenzyloxy, dioxolanyl-$C_{1-6}$-alkoxy, cyclopropyl-$C_{1-6}$-alkoxy, pyridylcarbamoyloxy-$C_{1-6}$-alkoxy, 3-morpholino-2-hydroxypropoxy, benzyloxy-$C_{1-6}$-alkoxy, picolyloxy, $C_{1-6}$-alkoxycarbonyl, $C_{1-6}$-alkoxy-$C_{1-6}$-alkoxy-$C_{1-6}$-alkyl, $C_{1-6}$-alkylcarbonylamino, $C_{1-6}$-alkylcarbonylamino-$C_{1-6}$-alkyl, $C_{1-6}$-alkylcarbonylamino-$C_{1-6}$-alkoxy, (N-$C_{1-6}$-alkyl)-$C_{1-6}$-alkylcarbonylamino-$C_{1-6}$-alkyl, (N-$C_{1-6}$-alkyl)-$C_{1-6}$-alkylcarbonylamino-$C_{1-6}$-alkoxy, $C_{3-6}$-cycloalkylcarbonylamino-$C_{1-6}$-alkyl, $C_{3-6}$-cycloalkylcarbonylamino-$C_{1-6}$-alkoxy, $C_{1-6}$-alkoxy-$C_{1-6}$-alkyl, hydroxy-$C_{1-6}$-alkyl, hydroxy-$C_{2-7}$-alkoxy-$C_{1-6}$-alkyl, hydroxy-$C_{2-7}$-alkoxy-$C_{1-6}$-alkoxy, $C_{1-6}$-alkoxycarbonylamino-$C_{1-6}$-alkyl, $C_{1-6}$-alkoxycarbonylamino-$C_{2-7}$-alkoxy, $C_{1-6}$-alkylaminocarbonylamino-$C_{1-6}$-alkyl, $C_{1-6}$-alkylaminocarbonylamino-$C_{2-7}$-alkoxy, $C_{1-6}$-alkylaminocarbonyl-$C_{1-6}$-alkyl, $C_{1-6}$-alkylaminocarbonyl-$C_{1-6}$-alkoxy, $C_{1-6}$-alkylaminocarbonyl-$C_{1-6}$-alkoxy-$C_{1-6}$-alkyl, di-$C_{1-6}$-alkylaminocarbonyl-$C_{1-6}$-alkyl, di-$C_{1-6}$alkylaminocarbonyl-$C_{1-6}$-alkoxy, $C_{1-6}$alkylcarbonyloxy-$C_{1-6}$-alkyl, $C_{1-6}$-alkylcarbonyloxy-$C_{1-6}$-alkoxy, cyano-$C_{1-6}$-alkyl, cyano-$C_{1-6}$-alkoxy, 2-oxooxazolidinyl-$C_{1-6}$-alkyl, 2-oxooxazolidinyl-$C_{1-6}$-alkoxy, $C_{1-6}$-alkoxycarbonyl-$C_{1-6}$-alkyl, $C_{1-6}$-alkoxycarbonyl-$C_{1-6}$-alkoxy, $C_{1-6}$-alkylsulphonylamino-$C_{1-6}$-alkyl, $C_{1-6}$-alkylsulphonylamino-$C_{2-7}$-alkoxy, (N-$C_{1-6}$-alkyl)-$C_{1-6}$-alkylsulphonylamino-$C_{1-6}$-alkyl, (N-$C_{1-6}$-alkyl)-$C_{1-6}$-alkylsulphonylamino-$C_{1-6}$-alkoxy, $C_{1-6}$-alkylamino-$C_{1-6}$-alkyl, $C_{1-6}$-alkylamino-$C_{2-7}$-alkoxy, di-$C_{1-6}$-alkylamino-$C_{1-6}$-alkyl, Di-$C_{1-6}$-alkylamino-$C_{2-7}$-alkoxy, $C_{1-6}$-alkylsulphonyl-$C_{1-6}$-alkyl, $C_{1-6}$-alkylsulphonyl-$C_{1-6}$-alkoxy, carboxy-$C_{1-6}$-alkyl, carboxy-$C_{1-6}$-alkoxy, carboxy-$C_{1-6}$-alkoxy-$C_{1-6}$-alkyl, $C_{1-6}$-alkoxy-$C_{1-6}$-alkylcarbonyl, acyl-$C_{1-6}$-alkoxy-$C_{1-6}$-alkyl, (N-$C_{1-6}$-alkyl)-$C_{1-6}$alkoxy-carbonylamino, (N-hydroxy)-$C_{1-6}$-alkylaminocarbonyl-$C_{1-6}$-alkyl, (N-hydroxy)-$C_{1-6}$-alkylaminocarbonyl-$C_{1-6}$-alkoxy, (N-hydroxy) aminocarbonyl-$C_{1-6}$-alkyl, (N-hydroxy) aminocarbonyl-$C_{1-6}$-alkoxy, $C_{1-6}$-alkoxyaminocarbonyl-$C_{1-6}$-alkyl, 6-alkoxy-aminocarbonyl-$C_{1-6}$-alkoxy, (N-$C_{1-6}$-alkoxy)-$C_{1-6}$-alkylaminocarbonyl-$C_{1-6}$-alkyl, (N-$C_{1-6}$-alkoxy)-$C_{1-6}$-alkylaminocarbonyl-$C_{1-6}$-alkoxy, (N-acyl)-$C_{1-6}$-alkoxy-$C_{1-6}$-alkylamino, $C_{1-6}$-alkoxy-$C_{1-6}$-alkylcarbamoyl, (N-$C_{1-6}$-alkyl)-$C_{1-6}$-alkoxy-$C_{1-6}$-alkylcarbamoyl, $C_{1-6}$-alkoxy-$C_{1-6}$- alkylcarbonyl, $C_{1-6}$-alkoxy-$C_{1-6}$-alkylcarbonylamino, (N-$C_{1-6}$-alkyl)-$C_{1-6}$-alkoxy-$C_{1-6}$-alkylcarbonylamino, 1-$C_{1-6}$-alkoxy-$C_{1-6}$-alkylimidazol-2-yl, 1-$C_{1-6}$-alkoxy-$C_{1-6}$-alkyltetrazol-5-yl, 5-$C_{1-6}$-alkoxy-$C_{1-6}$-alkyltetrazol-1-yl, 2-$C_{1-6}$-alkoxy-$C_{1-6}$-alkyl-4-oxoimidazol-1-yl, carbamoyl -$C_{1-6}$-alkyl, carbamoyl-$C_{1-6}$-alkoxy, $C_{1-6}$-alkylcarbamoyl, di-$C_{1-6}$-alkylcarbamoyl, $C_{1-6}$-alkylsulphonyl, piperidinoalkyl, piperidinoalkoxy, piperidinoalkoxyalkyl, morpholinoalkyl, morpholinoalkoxy, morpholinoalkoxyalkyl, piperazinoalkyl, piperazinoalkoxy, piperazinoalkoxyalkyl, [1,2,4]-triazol-1-ylalkyl, [1,2,4]-triazol-1-ylalkoxy, [1,2,4]-triazol-4-ylalkyl, [1,2,4]-triazol-4-ylalkoxy, [1,2,4]-oxadiazol-5-ylalkyl, [1,2,4]-oxadiazol-5-ylalkoxy, 3-methyl-[1,2,4]-oxadiazol-5-ylalkyl, 3-methyl-[1,2,4]-oxadiazol -5-ylalkoxy, 5-methyl-[1,2,4]-oxadiazol-3-ylalkyl, 5methyl-[1,2,4]-oxadiazol-3-ylalkoxy, tetrazol-1-ylalkyl, tetrazol-1-ylalkoxy, tetrazol-2-ylalkyl, tetrazol-2-ylalkoxy, tetrazol-5-ylalkyl, tetrazol-5-ylalkoxy, 5-methyltetrazol-1-ylalkyl, 5-methyltetrazol-1-ylalkoxy, thiazol-4-ylalkyl, thiazol-4-ylalkoxy, oxazol- 4-ylalkyl, oxazol-4-ylalkoxy, 2-oxopyrrolidinylalkyl, 2-oxopyrrolidinylalkoxy, imidazolylalkyl, imidazolylalkoxy, 2-methylimidazolylalkyl, 2-methylimidazolylalkoxy, N-methylpiperazinoalkyl, N-methylpiperazinoalkoxy, N-methylpiperazinoalkoxyalkyl, pyrrolidinyl, piperidinyl, piperazinyl, pyrrolyl, 4-methylpiperazinyl, morpholinyl, thiomorpholinyl, 2-hydroxymethylpyrrolidinyl, 3-hydroxypyrrolidinyl, 3,4-dihydroxypyrrolidinyl, 3-acetamidomethylpyrrolidinyl, 3-$C_{1-6}$alkoxy -$C_{1-6}$-alkyl-pyrrolidinyl, 4-hydroxypiperidinyl, 4-oxopiperidinyl, 3,5-dimethylmorpholinyl, 4,4-dioxothiomorpholinyl, 4-oxothiomorpholinyl, 2,6-dimethylmorpholinyl, 2-oxoimidazolidinyl, 2-oxooxazolidinyl, 2-oxopyrrolidinyl, 2-oxo[1,3]oxazinyl and 2-oxotetrahydropyrimidinyl.

6. A compound of the formula

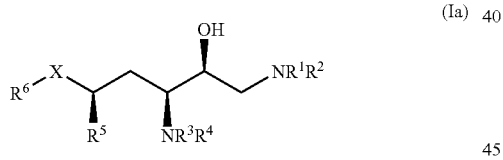

(Ia)

where

X is methylene or hydroxymethylene;

$R^1$ a) is hydrogen; or b) is $C_1$-$C_8$-alkyl, $C_3$-$C_8$-cycloalkyl, $C_1$-$C_8$-alkanoyl, $C_1$-$C_8$-alkoxycarbonyl, or heterocyclyl-$C_0$-$C_4$-alkyl, which radicals may be substituted by 1-4 $C_1$-$C_8$-alkyl, halogen, cyano, oxide, oxo, trifluoromethyl, $C_1$-$C_8$-alkoxy, $C_1$-$C_8$-alkoxycarbonyl, aryl or heterocyclyl;

$R^2$ a) is $C_1$-$C_8$-alkyl, $C_3$-$C_8$-cycloalkyl, $C_1$-$C_8$-alkylsulphonyl, $C_3$-$C_8$-cycloalkylsulphonyl, aryl -$C_0$-$C_8$-alkylsulphonyl, heterocyclylsulphonyl, $C_3$-$C_{12}$-cycloalkyl-$C_1$-$C_8$-alkanoyl, $C_3$-$C_{12}$-cycloalkyl-$C_3$-$C_8$-cycloalkanoyl, aryl-$C_1$-$C_8$-alkanoyl, heterocyclyl-$C_1$-$C_8$-alkanoyl, aryl-$C_3$-$C_8$-cycloalkanoyl, $C_1$-$C_8$-alkanoyl, $C_1$-$C_8$-alkoxycarbonyl, optionally N-mono or N, N-di-$C_1$-$C_8$-alkylated carbamoyl-$C_0$-$C_8$-alkyl, or heterocyclyl-$C_0$-$C_4$-alkyl, which radicals may be substituted by 1-4 $C_1$-$C_8$-alkyl, $C_3$-$C_8$-cycloalkyl, $C_3$-$C_8$-cycloalkoxy, amino, $C_{1-6}$-alkylamino, di-$C_{1-6}$-alkylamino, $C_0$-$C_6$-alkylcarbonylamino, halogen, cyano, hydroxyl, oxide, oxo, trifluoromethyl, $C_1$-$C_8$-alkoxy, optionally N-mono or N, N-di-$C_1$-$C_8$-alkylated carbamoyl, $C_1$-$C_8$-alkoxycarbonyl, $C_{1-6}$-alkylenedioxy, aryl or heterocyclyl; or b) together with $R_1$ and the nitrogen atom to which they are bonded, is a saturated or partly unsaturated 4-8-membered heterocyclic ring which may contain an additional nitrogen, oxygen or sulphur atom or an —SO - or —SO2-group, and the additional nitrogen atom may optionally be substituted by $C_1$-$C_8$-alkyl, $C_1$-$C_8$-alkanoyl, $C_1$-$C_8$-alkoxycarbonyl, aryl or heterocyclyl radicals, in which case this heterocyclic ring may be part of a bicyclic or tricyclic ring system having a total of up to 16 members and the second ring may also contain a nitrogen, oxygen or sulphur atom or an —SO - or —SO2-group, and the nitrogen atom of the second ring may optionally be substituted by $C_1$-$C_8$-alkyl, $C_1$-$C_8$-alkanoyl, $C_1$-$C_8$-alkoxycarbonyi, aryl or heterocyclyl radicals, and all ring systems mentioned may be substituted by 1-4 $C_1$-$C_8$-alkyl, halogen, hydroxyl, oxide, oxo, trifluoromethyl, $C_1$-$C_8$-alkoxy, $C_1$-$C_8$-alkoxy-$C_1$-$C_8$-alkyl, $C_1$-$C_8$-alkoxy-$C_1$-$C_8$-alkoxyl, $C_1$-$C_8$-alkoxycarbonylamino, $C_1$-$C_8$-alkylcarbonylamino, $C_1$-$C_8$-alkylamino, N,N-di-$C_1$-$C_8$-alkylamino, aryl-$C_0$-$C_4$-alkyl, arylxoxy-$C_0$-$C_4$-alkyl, aryl-$C_0$-$C_4$-alkyl-$C_1$-$C_8$-alkoxy, arylxoxy-$C^0$-$C_4$-alkyl-$C_1$-$C_8$-alkoxy, heterocyclyl-$C_0$-$C_4$-alkyl, heterocyclytoxy-$C_0$-$C_4$-alkyl, heterocyclyl-$C_0$-$C_4$-alkyl-$C_1$-$C_8$-alkoxy or heterocyclyloxy-$C_0$-$C_4$-alkyl-$C_1$-$C_8$-alkoxy;

$R^3$ is hydrogen, $C_1$-$C_4$-alkyl, $C_1$-$C_8$-alkoxycarbonyl or $C_1$-$C_8$-alkanoyl;

$R^4$ is hydrogen, $C_1$-$C_4$-alkyl, $C_1$-$C_8$-alkoxycarbonyl or $C_1$-$C_8$-alkanoyl;

$R^5$ is hydrogen, or $C_1$-$C_8$-alkyl;

$R^6$ is an unsubstituted polycyclic, unsaturated hydrocarbon radical excluding naphthyl, or a polycyclic, unsaturated hydrocarbon radical excluding naphthyl, which is substituted by from one to four radicals selected from $C_1$-$C_6$-alkyl, $C_{3-8}$-cycloalkyl, $C_{3-8}$-cycloalkoxy, $C_{3-8}$-cycloalkoxy-$C_{1-6}$-alkyl, $C_{3-8}$cycloalkoxy -$C_{1-6}$-alkoxy, $C_1$-$C_6$-alkylamino, di-$C_1$-$C_6$-alkylamino, amino-$C_{1-6}$-alkyl, amino-$C_{2-7}$-alkoxy, polyhalo-$C_{1-6}$-alkyl, polyhalo-$C_{2-7}$-alkoxy, nitro, amino, $C_2$-$C_6$-alkenyl, $C_1$-$C_6$-alkoxy, $C_1$-$C_6$-alkanoyloxy, hydroxyl, halogen, oxide, oxo, cyano, carbamoyl, carboxy, $C_1$-$C_6$-alkylenedioxy, phenyl, phenoxy, phenylthio, phenyl-$C_1$-$C_6$-alkyl or phenyl-$C_1$-$C_6$-alkoxy, each of which are optionally substituted by halogen, $C_1$-$C_6$-alkyl, $C_{1-6}$-alkoxy, hydroxyl, $C_1$-$C_6$-alkylamino, di-$C_1$-$C_6$-alkylamino, $C_{1-6}$-alkoxycarbonyl, hydroxy-$C_{1-6}$-alkyl or trifluoromethyl, pyridylcarbonylamino-$C_{1-6}$-alkyl, $C_{2-7}$-alkenyloxy, $C_{1-6}$-alkoxy-$C_{1-6}$-alkoxy, $C_{1-6}$-alkoxy-$C_{1-6}$-alkoxy-$C_{1-6}$-alkyl, methoxybenzyloxy, hydroxybenzyloxy, methylenedioxybenzytoxy, dioxolanyl-$C_{1-6}$-alkoxy, $C_{3-8}$-cycloalkyl-$C_{1-6}$-alkyl, $C_{3-8}$-cycloalkyl-$C_{1-6}$-alkoxy, hydroxy-$C_{2-7}$-alkoxy, carbamoyloxy-$C_{2-7}$-alkoxy, pyridylcarbamoyloxy-$C_{2-7}$-alkoxy, benzoyloxy-$C_{2-7}$-alkoxy, $C_{1-6}$-alkoxycarbonyl, $C_{1-6}$-alkylcarbonylamino, $C_{1-6}$-alkylcarbonylamino-$C_{1-6}$-alkyl, $C_{1-6}$-alkylcarbonylamino-$C_{2-7}$-alkoxy, (N-$C_{1-6}$-alkyl)-$C_{1-6}$-alkylcarbonylamino-$C_{1-6}$-alkyl, (N-$C_{1-6}$-alkyl)-$C_{1-6}$ -alkylcarbonylamino-$C_{2-7}$-alkoxy, $C_{3-8}$-cycloalkylcarbonylamino-$C_{1-6}$-alkyl, $C_{3-8}$-cycloalkylcarbonylamino-$C_{2-7}$-alkoxy, $C_{1-6}$-alkoxy-$C_{1-6}$-alkyl, hydroxy-$C_{1-6}$-alkyl, hydroxy -$C_{2-7}$-alkoxy-$C_{1-6}$-alkyl, hydroxy-$C_{2-7}$-alkoxy-$C_{1-6}$-alkoxy, $C_{1-6}$-alkoxycarbonylamino-$C_{1-6}$-alkyl, $C_{1-6}$-alkoxycarbonylamino-$C_{2-7}$-alkoxy, $C_{1-6}$-alkylaminocarbonylamino- $C_{1-6}$-alkyl, $C_{1-6}$-carbonylamino-$C_{2-7}$-alkoxy, $C_{1-6}$-alkylaminocarbonyl-$C_{1-6}$-alkyl, $C_{1-6}$-alkylaminocarbonyl-$C_{1-6}$-alkoxy, $C_{1-6}$-alkylaminocarbonyl-$C_{1-6}$-alkoxy-$C_{1-6}$-alkyl,di-$C_{1-6}$-alkylaminocarbonyl-$C_{1-6}$-alkyl, di-$C_{1-6}$-alkylaminocarbonyl-$C_{1-6}$-alkoxy, $C_{1-6}$-alkylcarbonyloxy-$C_{1-6}$-alkyl, $C_{1-6}$-alkylcarbonyloxy-$C_{2-6}$-alkoxy, cyano-$C_{1-6}$-alkyl, cyano -$C_{1-6}$-alkoxy, 2-oxooxazolidinyl-$C_{1-6}$-alkyl, 2-oxo-oxazolidinyl-$C_{1-6}$-alkoxy, $C_{1-6}$-alkoxycarbonyl-$C_{1-6}$-alkyl, $C_{1-6}$-alkoxycarbonyl-$C_{1-6}$-alkoxy, $C_{1-6}$-alkylsulphonylamino-$C_{1-6}$-alkyl, $C_{1-6}$-alkylsulphonylamino-$C_{2-7}$-alkoxy, (N-$C_{1-6}$-alkyl)-$C_{1-6}$-alkylsulphonylamino-$C_{1-6}$-alkyl, (N-$C_{1-6}$-alkyl)-$C_{1-6}$-alkylsulphonylamino-$C_{2-7}$-alkoxy, $C_{1-6}$-alkylamino-$C_{1-6}$-alkyl, $C_{1-6}$-alkylamino-$C_{2-7}$-alkoxy, di-$C_{1-6}$-alkylamino-$C_{1-6}$-alkyl, di-$C_{1-6}$-alkylamino-$C_{2-7}$-alkoxy, $C_{1-6}$-alkylsulphonyl-$C_{1-6}$-alkyl, $C_{1-6}$-alkylsulphonyl-$C_{1-6}$-alkoxy, carboxy-$C_{1-6}$-alkyl, carboxy-$C_{1-6}$-alkoxy, carboxy-$C_{1-6}$-alkoxy-$C_{1-6}$-alkyl, $C_{1-6}$-alkoxy-$C_{1-6}$-alkylcarbonyl, acyl -$C_{1-6}$-alkoxy-$C_{1-6}$-alkyl, (N-$C_{1-6}$-alkyl)-$C_{1-6}$-alkoxycarbonylamino, (N-hydroxy)-$C_{1-6}$-alkylaminocarbonyl-$C_{1-6}$-alkyl, (N-hydroxy)-$C_{1-6}$-alkylaminocarbonyl-$C_{1-6}$-alkoxy, (N-hydroxy)aminocarbonyl-$C_{1-6}$-alkyl, (N-hydroxy)aminocarbonyl-$C_{1-6}$-alkoxy, $C_{1-6}$alkoxy -aminocarbonyl-$C_{1-6}$-alkyl, 6-alkoxyaminocarbonyl-$C_{1-6}$-alkoxy, (N-$C_{1-6}$ alkoxy)-$C_{1-6}$-alkylaminocarbonyl-$C_{1-6}$-alkyl, (N-$C_{1-6}$ alkoxy)-$C_{1-6}$-alkylaminocarbonyl-$C_{1-6}$-alkoxy, (N-acyl) -$C_{1-6}$-alkoxy-$C_{1-6}$-alkylamino, $C_{1-6}$-alkoxy-$C_{1-6}$-alkylcarbamoyl, (N-$C_{1-6}$alkyl)-$C_{1-6}$-alkoxy-$C_{1-6}$-alkylcarbamoyl, $C_{1-6}$-alkoxy-$C_{1-6}$-alkylcarbonyl, $C_{1-6}$alkoxy-$C_{1-6}$-alkylcarbonylamino, (N-$C_{1-6}$-alkyl)-$C_{1-6}$-alkoxy-$C_{1-6}$-alkylcarbonylamino, 1-$C_{1-6}$alkoxy-$C_{1-6}$-alkylimidazol-2-yl, 1-$C_{1-6}$-alkoxy-$C_{1-6}$-alkyltetrazol-5-yl, 5-$C_{1-6}$-alkoxy-$C_{1-6}$-alkyltetrazol-1-yl, 2-$C_{1-6}$-alkoxy-$C_{1-6}$-alkyl-4-oxoimidazol-1-yl, carbamoyl-$C_{1-6}$-alkyl, carbamoyl-$C_{1-6}$-alkoxy, $C_{1-6}$-alkylcarbamoyl, di-$C_{1-6}$-alkylcarbamoyl, $C_{1-6}$-alkylsulphonyl, $C_{1-6}$-alkylamidinyl, acetamidinyl-$C_{1-6}$-alkyl, O-methyloximyl-$C_{1-6}$-alkyl, O,N -dimethylhydroxylamino-$C_{1-6}$-alkyl, $C_{3-6}$-cycloalkyl-$C_{1-6}$-alkanoyl, aryl-$C_{1-6}$-alkanoyl or heterocyclyl-$C_{1-6}$-alkanoyl, or else pyridyl, pyridyloxy, pyridylthio, pyridylamino, pyridyl -$C_{1-6}$-alkyl, pyridyl-$C_{1-6}$-alkoxy, pyrimidinyl, pyrimidinyloxy, pyrimidinylthio, pyrimidinylamino, pyrimidinyl-$C_{1-6}$-alkyl, pyrimidinyl-$C_{1-6}$-alkoxy, thienyl, thienyl-$C_{1-6}$-alkyl, thienyl-$C_{1-6}$-alkoxy, furyl, furyl-$C_{1-6}$-alkyl or furyl-$C_{1-6}$-alkoxy, each of which is optionally substituted by halogen, $C_{1-6}$-alkyl, $C_{1-6}$-alkoxy or dihydroxy-$C_{1-6}$-alkylaminocarbonyl, piperidinoalkyl, piperidinoalkoxy, piperidinoalkoxyalkyl, morpholinoalkyl, morpholinoalkoxy, morpholinoalkoxyalkyl, piperazinoalkyl, piperazinoalkoxy, piperazinoalkoxyalkyl, [1,2,4]-triazol-1-ylalkyl, [1,2,4]-triazol-1-ylalkoxy, [1,2,4]-triazol-4-ylalkyl, [1,2,4]-triazol-4-ylalkoxy, [1,2,4]-oxadiazol-5-ylalkyl, [1,2,4]-oxadiazol-5-ylalkoxy, 3-methyl-[1,2,4]-oxadiazol-5-ylalkyl, 3-methyl-[1,2,4]- -oxadiazol-5-ylalkoxy, 5-methyl-[1,2,4]-oxadiazol-3-ylalkyl, 5-methyl-[1,2,4]-oxadiazol-3- ylalkoxy, tetrazol-1-ylalkyl, tetrazol-1-ylalkoxy, tetrazol-2-ylalkyl, tetrazol-2-ylalkoxy, tetrazol-5-ylalkyl, tetrazol-5-ylalkoxy, 5-methyl-tetrazol-1-ylalkyl, 5-methyl-tetrazol-1-ylalkoxy, thiazol-4-ylalkyl, thiazol-4-ylalkoxy, oxazol-4-ylalkyl, oxazol-4-ylalkoxy, 2oxo -pyrrolidinylalkyl, 2-oxo-pyrrolidinylalkoxy, imidazolylalkyl, imidazolylalkoxy, 2methyl- imidazolylalkyl, 2-methyl-imidazolylalkoxy, N-methylpiperazinoalkyl, N-methylpiperazinoalkoxy, N-methylpiperazinoalkoxyalkyl, dioxolanyl, dioxanyl, dithiolanyl, dithianyl, pyrrolidinyl, piperidinyl, piperazinyl, pyrrolyl, 4-methylpiperazinyl, morpholinyl, thiomorpholinyl, 2-hydroxymethylpyrrolidinyl, 3-hydroxypyrrolidinyl, 3,4-dihydroxypyrrolidinyl, 3-acetamidomethylpyrrolidinyl, 3-$C_{1-6}$-alkoxy-$C_{1-6}$alkyl -pyrrolidinyl, 4-hydroxypiperidinyl, 4-oxopiperidinyl, 3,5-dimethylmorpholinyl, 4,4-dioxothiomorpholinyl, 4-oxothiomorpholinyl, 2,6-dimethylmorpholinyl, 2-oxo -imidazolidinyl, 2-oxooxazolidinyl, 2-oxopyrrolidinyl, 2-oxo[1,3]oxazinyl, 2oxo -tetrahydropyrimidinyl and the —O—CH$_2$CH(OH)CH$_2$NR$_x$ radical where NR$_x$ is a mono- or di-$C_{1-6}$-alkylamino, piperidino, morpholino, piperazino or N-methylpiperazino radical;

or a prodrug thereof, or a salt thereof.

7. A pharmaceutical preparation comprising, as an active pharmaceutical ingredient, a compound according to claim 1 or 6 in free form or as a pharmaceutically usable salt.

8. A process for preparing a medicament for the treatment of hypertension, heart failure, glaucoma, myocardial infarction, kidney failure or restenoses, which comprises blending a compound according to claim 1 or 6 with a pharmaceutically inert, inorganic or organic excipient.

9. A process according to claim 8, characterized in that the preparation is effected additionally with one or more agents having cardiovascular action, for example α and β-blockers such as phentolamine, phenoxybenzamine, prazosin, terazosin, tolazine, atenolol, metoprolol, nadolol, propranolol, timolol, carteolol etc.; vasodilators such as hydralazine, minoxidil, diazoxide, nitroprusside, flosequinan etc.; calcium antagonists such as amrinone, bencyclan, diltiazem, fendiline, flunarizine, nicardipine, nimodipine, perhexilene, verapamil, gallopamil, nifedipine etc.; ACE inhibitors such as cilazapril, captopril, enalapril, lisinopril etc.; potassium activators such as pinacidil; anti-serotoninergics such as ketanserin; thromboxane-synthetase inhibitors; neutral endopeptidase inhibitors (NEP inhibitors); angiotensin II antagonists; and also diuretics such as hydrochlorothiazide, chlorothiazide, acetazolamide, amiloride, bumetanide, benzthiazide, ethacrynic acid, furosemide, indacrinone, metolazone, spironolactone, triamteren, chlorthalidone etc.; sympatholytics such as methyldopa, clonidine, guanabenz, reserpine; and other agents which are suitable for the treatment of hypertension, heart failure or vascular diseases in humans and animals which are associated with diabetes or renal disorders such as acute or chronic renal failure.

10. A method for the treatment of hypertension, heart failure, myocardial infarction, kidney failure or restenoses, characterized in that the human or animal body is treated with an effective amount of a compound according to claim 1 or 6.

* * * * *

UNITED STATES PATENT AND TRADEMARK OFFICE
CERTIFICATE OF CORRECTION

| | | Page 1 of 1 |
|---|---|---|
| PATENT NO. | : 7,868,036 B2 | |
| APPLICATION NO. | : 10/593461 | |
| DATED | : January 11, 2011 | |
| INVENTOR(S) | : Herold et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 169 days.

Signed and Sealed this
Twenty-eighth Day of June, 2011

David J. Kappos
*Director of the United States Patent and Trademark Office*